(12) United States Patent
Rodrigues et al.

(10) Patent No.: US 7,838,259 B2
(45) Date of Patent: Nov. 23, 2010

(54) **GENES OF *PORPHYROMONAS GINGIVALIS* W83 INVOLVED IN INVASION OF HUMAN CELLS**

(75) Inventors: Paulo Henrique Rodrigues, Gainesville, FL (US); Ann Progulske-Fox, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 52 days.

(21) Appl. No.: 11/814,942

(22) PCT Filed: Feb. 1, 2006

(86) PCT No.: PCT/US2006/003841

§ 371 (c)(1), (2), (4) Date: Jun. 10, 2008

(87) PCT Pub. No.: WO2006/084129

PCT Pub. Date: Aug. 10, 2006

(65) Prior Publication Data

US 2008/0311596 A1 Dec. 18, 2008

Related U.S. Application Data

(60) Provisional application No. 60/648,765, filed on Feb. 1, 2005.

(51) Int. Cl.
*G01N 33/569* (2006.01)
*G01N 33/566* (2006.01)
*G01N 33/53* (2006.01)
*C07K 16/18* (2006.01)

(52) U.S. Cl. ............... 435/7.32; 435/7.1; 435/7.92; 435/252.1; 530/350; 530/387.1; 530/387.3; 530/387.9

(58) Field of Classification Search ............... None
See application file for complete search history.

(56) References Cited

U.S. PATENT DOCUMENTS 7,416,852 B2 * 8/2008 Progulske-Fox et al. ... 435/7.32

FOREIGN PATENT DOCUMENTS

WO  WO 97/36923  10/1997
WO  WO 01/83530 A1  11/2001

OTHER PUBLICATIONS

Nelson et al, Journal of Bacteriology, Sep. 2003, p. 5591-5601, vol. 185, No. 18.*
Q9XCA2 dated Nov. 1, 1999.*
Beck, et al., "Periodontal Disease and Cardiovascular Disease", J. Periodontol. 67:1123-1137 (1996).
Deshpande, et al., "Invasion of Aortic and Heart Endothelial Cells by *Porphyromonas gingivalis*", Infection and Immunity, vol. 66, No. 11, p. 5337-5343 (1998).
Dorn, et al., "Invasion of Human Coronary Artery Cells by Periodontal Pathogens", Infection and Immunity, vol. 67, No. 11, p. 5792-5798 (1999).
Haraszthy, et al., "Identification of Perodontal Pathogens in Atheromatous Plaques", J. Periodontol. 71:1554-1560 (2000).
Haverkate, et al., "Prodution of C-reactive protein and risk of coronary events in stable and unstable angina", The Lancet, 349:462-466 (1997).
Lamont, et al., "Interaction of *Porphyromonas gingivalis* with gingival epithelial cells maintained in culture", Oral Microbiol. Immunol. 1992: 7:364-367.
Leaverton, et al., "Representativeness of the Framingham risk model for coronary heart disease mortality: a comparison with a national cohort study", J. Chron. Dis. vol. 40, No. 8, p. 775-784 (1987).
Mattila, et al., "Role of Infection as a Risk Factor for Atherosclerosis, Myocardial Infarction, and Stroke", Clinical Infectious Diseases, 26:719-734 (1998).
Nelson, et al., "Complete Genome Sequence of the Oral Pathogenic Bacterium *Porphyromonas gingivalis* Strain W83", Journal of Bacteriology, vol. 185, No. 18, p. 5591-5601 (2003).
Rudney, et al., "Intracellular *Actinobacillus actinomycetemcomitans* and *Porphyromonas gingivalis* in Buccal Epithelial Cells Collected from Human Subjects", Infection and Immunity, vol. 69, No. 4, p. 2700-2707 (2001).
Papapanou, et al., "*Porphyromonas gingivalis* invades oral epithelial cells in vitro", J. Periodont. Res. 28:219-226 (1993).
Silver, et al., "Experimental transient bacteraemias in human subject with varying degrees of plaque accumulation and gingival inflammation", Journal of Clinical Periodontology, 4:90-99 (1977).
Socransky, et al., "The Bacterial Etiology of Destructive Periodontal Disease: Current Concepts", J. Periodontol. 63:322-331 (1992).
Sconyers, et al., "Relationship of baceremia to toothbrushing in patients with periodontitis", J. Am. Dent. Assoc. 87:616-622 (1973).
U.S. Appl. No. 60/648,765, filed Feb. 1, 2005.

* cited by examiner

*Primary Examiner*—Robert B Mondesi
*Assistant Examiner*—Padma V Baskar
(74) *Attorney, Agent, or Firm*—McDonnell Boehnen Hulbert & Berghoff LLP

(57) ABSTRACT

Compositions and methods are provided for detection and treatment of *Porphyromonas gingivalis* infection.

12 Claims, 23 Drawing Sheets

FIGURE 7

SEQ ID NO:1
PG 0242

ATGGAAGGACGTTTGACAGTCGTGCCGACTCCTATCGGCAATTTGGAGGATATTACCTTGAGAGC
CTTGAAGGTACTGCGCGAAGCAGACCTGATTTTGGCAGAGGACACGCGTACCAGCAGTGTATTGC
TCCACCATTACGACATTCACTGTCCGCTCCAGAGCCATCATAAATTCAACGAACATCGTACGGCC
AAGTCATTGGCCGAACGGATATCCGGAGGTGAACGCATAGCTTTGATCTCCGACGCCGGAACTCC
CGGGATCAGCGACCCCGGTTTTTTGCTTGTCAGAGCATGTGCCGAGTTGGGTGTAGTGGTAGAAT
GTCTGCCCGGACCCACAGCATTGATTCCGGCTTTGGTAGCAAGCGGACTCCCTGCCGACAGGTTT
GTTTTCGAAGGTTTTCTGCCTGTCAAGAAAGGCCGCCAAACTCGAATGAAAGAATTGGCCGAAGA
GCTCCGGACGATGATATTTATGAGTCGCCCCATCGGGTGCTCAGGACTCTGACCCAATTTGTGG
AGACTTTCGGTCTCGATCGACCAGCTGCTGCATGCCGGGAGCTGAGCAAACTCCACGAAGAGGTG
ATCCGCGGAACACTCGCGGAATTACTGGCTCACTTCGAAAACCACCCTCCAAGGGGAGAATTCGT
TCTCATCGTGGGTGGAGCCGCCCCGAAAGGGAGAAAAGAAGAGAAGCAA

SEQ ID NO:2
Protein:

MEGRLTVVPTPIGNLEDITLRALKVLREADLILAEDTRTSSVLLHHYDIHCPLQSHHKFN
EHRTAKSLAERISGGERIALISDAGTPGISDPGFLLVRACAELGVVVECLPGPTALIPAL
VASGLPADRFVFEGFLPVKKGRQTRMKELAEELRTMIFYESPHRVLRTLTQFVETFGLDR
PAAACRELSKLHEEVIRGTLAELLAHFENHPPRGEFVLIVGGAAPKGRKEEKQ

SEQ ID NO:3
PG 0686

ATGCAGGTCATAAAAACAAATGAAACTTTTGACAGCCTCGACAAAAGTAAGTTGGAGCGTATGCT
CGACATCAAAGAGGCTCATCGCGAAGGTCATCTGACACTTGAAGAGGCCAAGGAGCGTATGAAAA
AAGAAGTGGGTTCCATCTCGCCCGAAGAGTTTGCCGCAGCAGAGCAACTCTTCAAAGAACGTGAT
CAGGACGAATGCCAAAACGAAGACGTACGACAATGCTACAGCTGTTCGAAGGCCTGATAAATCC
CATTCGTCCCGATTTACCTTTCGGACACCCCATCGATGCCTATCTGCGCGAAAACGATAAGGCCA
AAGAACTACTCGATCAGGCGGATGCCCTACTGGAGCGCACTTTTATCCCCAATCCATGGATAGAA
CTGATGGAGACGCTTATGGGATATAAGCTACACTTTGCTCGCAAACAAAACCAACTCTATTCGAC
ACTGGAGCAGAAAGGATTCGACCGCCCCTCCACTACGATGTGGACTTATGACGATCATATCCGCG
ACGAGATGAACAAAGCCATGAGCCTACTGCGCGAAAAAGACTACGACTCCTTCCCTGCAGCATAC
AAAGAGATGGCTATCGTTCTGCGTGACCTGATGGAAAAGAAGAGCTTATCCTTTATCCAACCTC
TCTGAAGCTCATTTCCGACAAAGAGTTCGAAGAAATGAAACATGGCGATCGGGAATAGGCTTCT
TCCTTATCGACATGCCGGAATTAGATGCACCGGCCAAGCAATCAAAAGAAGCCCACGGCCAATCA
TTTATGGCAGAACTGGGAGCCTTACTTGCCAAACATGGTATGGGGACAGGCGGACAAGACGACAA
GGCGATACTGGATGTAGCCGAAGGAAAGCTGACTTTGGAGCAGATCAATCTGCTTTTCCGTCATC
TCCCTGTGGATATTTCGTTCGTGGACGAAAACGAGCTGGTTTGTTTCTATACGGACACAAAGCAC
AGAGTATTCCCCAGAAGCAAGGGGGTGATCGGCCGAGAAGTACGCAACTGCCATCCGCCCAAGAG
CGTTCATATAGTAGAGGAGATAATCGATAAGTTCCGACGTGGCGAACAGGATCGCGCAGAATTCT
GGATCAATAAGCCCGGAGTCTTCATCTACATTGTCTATGTGGCCATCAGAGACGCCGACGGGCGT
TTCCGCGGTGTGATGGAAATGATGCAAGACTGCACACGGATCCGTAGTCTTGAAGGCTCGCGTAC
ACTTCTTACTTGGGACGAAGAGCAAAGTCCGGCACAAGGATCGAAAGAAAGCGAATCCGATACTG
CCGGAGAAGACGGCATTCGGCCGGACACGAAGCTGAAGAGTCTCTTGCAGCGGTATCCGCAACTG
ATGGATGATTTGCCAACGATCAGTTCCAAGTTCACCCTCCTTCGTTCTCCGATGGCCAAAGTAAT

TCTTCCTGTTGCCACCATTAAAATGATGAGCGAACGCGCCGACATTCCGTCGGATATGCTCATCG
GCAAACTGGAATCGCTCATCGCTTCGTACAATAAACCGGATCGATCGGAAGAGAAA

SEQ ID NO:4
Protein:

MQVIKTNETFDSLDKSKLERMLDIKEAHREGHLTLEEAKERMKKEVGSISPEEFAAAEQL
FKERDQDECQNEDVRTMLQLFEGLINPIRPDLPFGHPIDAYLRENDKAKELLDQADALLE
RTFIPNPWIELMETLMGYKLHFARKQNQLYSTLEQKGFDRPSTTMWTYDDHIRDEMNKAM
SLLREKDYDSFPAAYKEMAIVLRDLMEKEELILYPTSLKLISDKEFEEMKHGDREIGFFL
IDMPELDAPAKQSKEAHGQSFMAELGALLAKHGMGTGGQDDKAILDVAEGKLTLEQINLL
FRHLPVDISFVDENELVCFYTDTKHRVFPRSKGVIGREVRNCHPPKSVHIVEEIIDKFRR
GEQDRAEFWINKPGVFIYIVYVAIRDADGRFRGVMEMMQDCTRIRSLEGSRTLLTWDEEQ
SPAQGSKESESDTAGEDGIRPDTKLKSLLQRYPQLMDDLPTISSKFTLLRSPMAKVILPV
ATIKMMSERADIPSDMLIGKLESLIASYNKPDRSEEK

SEQ ID NO:5
PG 0717

ATGAAAGTATTCAAGTTTTTAGCATCGATGGTGCTGTTTGCAGGCTTATTTGCTGCATGCAACAA
GGAAGACAACGATCTCATCAATTCGACTTCGGATGAAGCGGCAACTTTGGCTACGATGTATCCCA
ATGCTCAGAATGTAAGATGGGAGCAAGAAGGTGAATTCCGTGTGGCAGAATTCATGAACGAAGGC
GTTAAGTCTGAAGCATGGTTCTTGCAAGCATCTGGCAATACACGGAGATAGACATTCCCTACAG
CGCCCTGCCTAAAGCAGTCCGAGCTGCTTTTGAGGCAAGTGAATATGCCAAGTGGAAAATAGAAG
ACATAGATAAGGTAGAACGTAACGGTACCGAAATATTCTATGTCATAGAAGTAGAAAAGGGAGAC
CAGGAAGTCGACTTGTTCTACATGCCCAATGGCAAGCTGATCAAAACCGTGAAAAAACCTCACAA
CGGATCAGCAGGTCAATATGCCAATCCGGTGATTCCGGCAGGAGTAATGAATACCATCAAGGCTT
ACATCGCTTCCAACTATCCTAATGCAACCATTCTGGAGTACGAGATCGAAGATGGCTACATAGAG
GTGGACATTTTGGATGGTACGGTACATCGAGTTCTTATTTTCACACTCCAAGGCGAGTGGGTAAA
TAGTCATGTGGATGATGGAGATGACGATTATGACTACGATGATGATGCATACGAAAACAACATTC
CGGCCAACATCAAGGCTCTGATCATCAGCTATGTCAATCAGAATTACCCGGGAGCTGTCATTCAC
AGTATCGAGCGTAACTCCAATGGTACTTATGACGTAGAAATTTACTACAACAATAGGGAGTACGA
CTTGCTGTTCGATGCACAGGGCAACCTCATCAGCGGAAACGTAGACGATCAGGATGATGACGACA
ACATTCCTGCTCACATCAAGGCTAAGATCATCAATTACGTCAACCGGAACTACCCCGGTGCATTT
ATCAAGGACATCGAAAGAAAGTCCAACGGCACATACAAGGCGGAAATCGTGTACAACAACAAGGA
GTATGATTTGCTGTTCGATGCACAGGGCAATTTCATCAGTGCGAGCCTGGATGACAAAAAA

SEQ ID NO:6
Protein:

MKVFKFLASMVLFAGLFAACNKEDNDLINSTSDEAATLATMYPNAQNVRWEQEGEFRVAE
FMNEGVKSEAWFLRSIWQYTEIDIPYSALPKAVRAAFEASEYAKWKIEDIDKVERNGTEI
FYVIEVEKGDQEVDLFYMPNGKLIKTVKKPHNGSAGQYANPVIPAGVMNTIKAYIASNYP
NATILEYEIEDGYIEVDILDGTVHRVLIFTLQGEWVNSHVDDGDDDYDYDDDAYENNIPA
NIKALIISYVNQNYPGAVIHSIERNSNGTYDVEIYYNNREYDLLFDAQGNLISGNVDDQD
DDDNIPAHIKAKIINYVNRNYPGAFIKDIERKSNGTYKAEIVYNNKEYDLLFDAQGNFIS
ASLDDKK

SEQ ID NO:7
PG 1286

ATGAAAATAAGCGAAAACGTAACTAAAGCGATCAATGACCAAATCAAGGCCGAAATGTGGTCTTC
AAACCTCTATTTGTCCATGTCTGTGCATTTTGCGCAGGTAGGGTACAACGGCTTTGCTCATTGGC
TCAAAAAGCAGAGCCTCGAGGAAATGGAACATGCCTACGATATGATGGACTACCTCCTGAAGCGT
GGCGGCGAGGTGAAGATAGAAGCTATCGATGCCGTGCCCCAGAAGTTCGGCTCTGTATTGGAGGT
ATTCCAACAGGTGTACGAACACGAGTGCAAAGTGACCGAAATGATCGAGGCTGTCGTAAGGGCTG
CTTCCGAAGCCGGAGATATGGCATCACAGGACTTCTTCTGGAAGTATATCCGCGAGCAGGTAGAA
GAGGAAGCCACTGCTGCCGAAATCGTCGAAACGATCCGTCTCTCTCAGGAGCAGAATCTGATCTT
CATCGATCATCAGCTCGCCCGGAGA

SEQ ID NO:8
Protein:

MKISENVTKAINDQIKAEMWSSNLYLSMSVHFAQVGYNGFAHWLKKQSLEEMEHAYDMMD
YLLKRGGEVKIEAIDAVPQKFGSVLEVFQQVYEHECKVTEMIEAVVRAASEAGDMASQDF
FWKYIREQVEEEATAAEIVETIRLSQEQNLIFIDHQLARR

SEQ ID NO:9
PG 1683

ATGAAACATATCTGCTTATACTTCCAAATACATCAGCCGTTTCGTCTGAAACGATACCGATTTTT
CGACATCGGGAACGACCATTACTACTACGACGACTTCCGCAATGAAGAAATCATGCGACGGATCA
CACAGAAGTGCTATCTGCCGGCCAATCTGCTTTTGAAGGAAATCATTGCCGAACATCCCGAGTTT
CGAGTAGCATTTTCTATTTCCGGTACTGCTTTGGAACAGCTGGAGTCCTATTCGCCGGAGGCCTT
GGACACCTTCAGAGATTTGGCCGAAACGGGCTGTGTAGAGTTTCTGGCCGAAACCTACGCTCATT
CCCTCTCGTCGCTCTATGATCCCGAAGAATTTTACAATCAGACGATGATCCATAGTCGTCGGATG
GAAGAGCTGTTCGGTGTAAAACCCCGAGTGCTGCGCAATACAGAGTTGATCTTCTCCGACAACAT
TGCCACCCAAGTGGCAGAAATGGGTTTTCAAGGGATGCTCACGGAAGGAGCCAAACACATACTCG
GATGGAAGAGTCCGAACTATCTGTACAAAGCCGGATCCGCTCCGGAGTTGTCCCTCTTGCTCCGC
AATCCGAGGCTGAGCGATGCCATCAGTGCCATGTTCACCCGCTACGATTGGAACGAATATCCCCT
GACGGCAGACAAGATGATCCGTTGGATCGAAGAGACTCCCGAAGAGGAGCAGATATTCAATCTCT
TCATGAACTACGAAGTCTTGGGATCGCTCCATCCGCAGGAGTCGGGTATTTTCGATTTCTTTCGT
GCACTCCCTTCTTTGGCGAAAAAGAGCGAAGGTGTCAAATTCGCTACGCCATCGGAGTTGATAGA
GTCCTCCAGCCCCGTAGCCAAGTTCTCCTCCATCTACCCCATAAGCTGGGTAGGAGAAGAAAAAG
ATACCGGTACGTGGCTGGGCAATGTGCTGCAACAAGGAGCATGCGACAAACTCGAACAATGGGC
GAACGTGTACGTATGATCGACGATCAGCGTATGCTACAGGACTGGCTCTATCTACAGAGCGCCGA
CCACTTCTACTATATGAAACCCGTGGCGGAGACGCCGGCAACTTCAGCCCGTACGAAACGCCTT
ACGATGCTTTCAACAACTATATGAATGTGCTCAGCGACTTCCTGCTTCGCGTAGAAGCCCGCTAC
CCTTCTACGATAGAAAATGAAGAACTGAAAGCCTTGCTGACTACAATCAGAAATCAGGATAAACA
AATCAAAAAATTAGAAGAGACAATCAAACGTCAAAAAACGAAAACAACA

SEQ ID NO:10
Protein:

MKHICLYFQIHQPFRLKRYRFFDIGNDHYYYDDFRNEEIMRRITQKCYLPANLLLKEIIA
EHPEFRVAFSISGTALEQLESYSPEALDTFRDLAETGCVEFLAETYAHSLSSLYDPEEFY
NQTMIHSRRMEELFGVKPRVLRNTELIFSDNIATQVAEMGFQGMLTEGAKHILGWKSPNY
LYKAGSAPELSLLLRNPRLSDAISAMFTRYDWNEYPLTADKMIRWIEETPEEEQIFNLFM
NYEVLGSLHPQESGIFDFFRALPSLAKKSEGVKFATPSELIESSSPVAKFSSIYPISWVG
EEKDTGTWLGNVLQQGACDKLEQWGERVRMIDDQRMLQDWLYLQSADHFYYMKTRGGDAG
NFSPYETPYDAFNNYMNVLSDFLLRVEARYPSTIENEELKALLTTIRNQDKQIKKLEETI
KRQKTKTT

Figure 8

SEQ ID NO:11
PG0520
1    makeikfdme srdllkkgvd alanavkvtl gpkgrnvils ktygaphitk dgvsvakeie
61   lecpfenmga qlvkevaskt nddagdgttt atilaqsiig vglknvtaga npmdlkrgid
121  kavkavvthi agmakevgdd fqkiehvaki sangdenigs liaeamrkvk kegvitveea
181  kgtdttvevv egmqfdrgyi spyfvtntdk mevqmenpfi liydkkisvl kemlpileqt
241  vqtgkpllii aedidseala tlvvnrlrgs lkicavkapg fgdrrkamle diailtggtv
301  iseetglkle natmdmlgta ekvtvdkdnt tivngagnke giasritqik aqienttsdy
361  dreklqerla klaggvavly vgaasevemk ekkdrvedal satraaieeg tvpgggtayi
421  raiaaleglk genedettgi eivkraieep lrqivanagk egavvvqkvk egkddfgyna
481  rtdvfenlyt tgvidpakvt rvalenaasi agmflttecv iadkkednpa apampggmgg
541  mggm SEQ ID NO:12
PG0593
1    mldkdtlaqv gsyfaqlkks ytlrlnahts hpsyneakem ldglasvsdh vraeynaadd
61   fridllvdga dsgigfrgip gghefsslll ailnndgigr nipdegvqdr irringpiel
121  ktyvslsctn cpdvvqtlnm iailnptinh tmvdgsffpd eveslgiasv ptvmagdevi
181  hvgrgdmaal lnkieakygs vpaesadktl rpfdllvvgg gpagsaaaiy sarkglkvai
241  vaervggqvn etvgienlis vpyttgsela snlnshikan tislfeartv ssitqqegis
301  rvevtsgevf tapalimatg aswrklgvpg ekeytgngva ycahcdgpff kgkrvavvgg
361  gnsgleaaid lagicehvtv vefldvlrad evlqkkaret anidillsta tkeimgngqk
421  vegilltdrn tgeekqials gvfvqiglaa ntslvkdlve tnsrgevlid tscrtntpgi
481  yaagdcttvp ykqiviamge gakaalsafe drirg SEQ ID NO:13
PG0619
1    mldkdtlaqv gsyfaqlkks ytlrlnahts hpsyneakem ldglasvsdh vraeynaadd
61   fridllvdga dsgigfrgip gghefsslll ailnndgigr nipdegvqdr irringpiel
121  ktyvslsctn cpdvvqtlnm iailnptinh tmvdgsffpd eveslgiasv ptvmagdevi
181  hvgrgdmaal lnkieakygs vpaesadktl rpfdllvvgg gpagsaaaiy sarkglkvai
241  vaervggqvn etvgienlis vpyttgsela snlnshikan tislfeartv ssitqqegis
301  rvevtsgevf tapalimatg aswrklgvpg ekeytgngva ycahcdgpff kgkrvavvgg
361  gnsgleaaid lagicehvtv vefldvlrad evlqkkaret anidillsta tkeimgngqk
421  vegilltdrn tgeekqials gvfvqiglaa ntslvkdlve tnsrgevlid tscrtntpgi
481  yaagdcttvp ykqiviamge gakaalsafe drirg SEQ ID NO:14
PG1118
1    mninnytiks qealqqavel trrhgqqaie pqhllkavmd qgesltdflf akmglnkgsi
61   atavdkliek lphvsggepy lshetnqvlq aaedaahrmk dkyvslehiv lailttrcea
121  stllkdagat eqllqsaiee lrkgrnvtsq saeeqynale kyavnlcqra rdgkldpvig
181  rddeirrvlq ilsrrtknnp iligepgvgk taiaeglayr ivrgdvpenl rnkqifsldm
241  galiagakyk gefeerlkav vnevtgaege iilfideiht lvgagksega mdaanilkpa
301  largelraig attldeyrky fekdkalerr fqmvmvdepd elsssisilrg lkekyenhhk
361  vrikddaiia avklshryit erflpdkaid lmdeaaarlr mevdslpeel deisrrikql
421  eiereaikre ndeekvqfld reiaelkeke asekaqwqne kdrinqiqql kidieelkfq
481  adraereqdy grvaeirygl ikqketeidt iqqqlhelqr ggsmikeeve addiadivsr
541  wtgipvsrml qserdkllhl edelhkrvig qdeairavad avrrsraglq dpkrpigsfi
601  flgttgvgkt elaralaell fddesmltri dmseyqekfs atrligappg yvgydeggql
661  teairrkpys vvlfdeieka hpdvfnvllq vlddgrltdn kghvvnfknt liimtsnlgs
721  diirermqnl taenrrslta rtadevmqll khtirpefln ridetivftp ltekeiyeiv
781  rlqldgivrq ladndvvlhy teavvtfaar egydpqfgar pvkrvlqrfv lnelskalla
841  dtvdstrpvl idcidgsivf rne

SEQ ID NO:15

```
PG1208
  1  mgkiigidlg  ttnscvsvle  gnepivitns  egkrttpsvv  afvdggerkv  gdpakrqait
 61  nptktiysik  rfmgetydqv  srevervpfk  vvrgdnntpr  vdidgrlytp  qeisamilqk
121  mkktaedylg  qevteavitv  payfndaqrq  atkeageiag  lkvrrivnep  taaslaygld
181  ksnkdmkiav  fdlgggtfdi  silelgdgvf  evkstngdth  lggddfdhvi  idwlaeefks
241  qegvdlrqdp  mamqrlkeaa  ekakielsst  ssteinlpyi  mpvngipkhl  vmtltrakfe
301  qladrliqac  vapcetalkd  aqmsrgdide  vilvggstri  paiqeiveki  fgkapskgvn
361  pdevvavgaa  iqggvltgev  kdvllldvtp  lslgietmgg  vmtrlidant  tiptkkseif
421  ttavdnqpsv  eihvlqgers  lakdnksigr  fnldgiapap  rqtpqievtf  didangilnv
481  tahdkatgkk  qnirieassg  lsddeikrmk  eeaqanaead  kkekeridki  nqadsmifqt
541  ekqlkelgdk  fpadkkapid  taldklkeah  kaqdvaaidt  amaelqtals  aageelykna
601  gaaqggaqpg  pdfggaqgps  agdqpsddkn  vtdvdfeevk SEQ ID NO:16
PG0985
  1  mntiafkeif  lpirpsirav  chaflrddee  aedatqevyl  rlwearmrld  gldnprayai
 61  riarnyclnl  irkasnspyp  tsleaaevqe  vsethggead  lllseqigrl  rqwlrgvsel
121  yrtvfamshf  rrlsngeiae  rlgltegnvr  vilcrlrrea  kevmkdda SEQ ID NO:17
PG1798
  1  mkkttiisli  vfgaffaavg  qtkdnssykp  fskediaggv  yslptqnraq  kdnaewllta
 61  tvstnqsadt  hfifdennry  iardikangv  rkstdsiyyd  angrishvdl  yisfsggepa
121  ldtrfkytyd  degkmtvrev  fmlvmdpntp  isrleyhyda  qgrlthwisf  afgaesqknt
181  yhynekgllv  sevlsnamgt  tysdtgktey  syddadnmvk  aeyfvvqqgk  awqvlkreey
241  tyedniciqy  laingtdtkv  ykrdiesdks  isanvidips  mpeqtwpnmy  gfnakrlket
301  yssyegdvat  pifdyiytyk  altsmatpst  eaqvavylnp  stdrlvilan  githlsmydl
361  qgklirdcal  sgdkvemgvg  sltkgtyllk  vntdqgafvr  kvvir SEQ ID NO:18
PG0538
  1  mnrfsnhwpc  ilvgfvlwfv  sasrtvaqna  settvsydtd  tavlseadvl  rialsenatv
 61  kvadmdvrkq  eyarraarad  lfpkvdlngv  yshtlkkqvl  yidmpgfsss  egiemgrthn
121  tqggvnvsmp  lvsaqlwksi  amtgeqldla  lekarssrid  lvaevkkayl  svllaedsyg
181  vfkrsydnal  anyknisdkf  drglvaeydk  iranvqvrni  epnllqaqns  valalwqlkv
241  lmsmevetpi  rlsgslsdyk  eqvytgyfaa  dtlisnnssl  rqldiqrrla  vsadklnkys
301  flptlnlgqq  ytyslnsndi  kfwgegqrwt  pfstislsly  ipifnggkrl  ynvkqsalsi
361  rqidlqrrhi  eqsirmgikn  qndrlrtcmq  rfvaseeavr  saekgyqiae  kryqtgegtl
421  velndadval  lqarlnynqa  ifdfmtakae  ldkmngmgip  eq SEQ ID NO:19
PG0611
  1  mktnikmrkt  iifclllalf  gcswaqervd  ekvfsagtsi  frgilekvka  plmygdrevw
 61  gmarasedff  filpvtddlt  pvlfynrltn  epcfvsdqgi  teyfkfaqeg  dyievegssv
121  fmanllyyrf  fptritsyna  piegvvsktg  npaftipmlp  gvsdcieisn  nrkvfltnql
181  gvvnitdgme  ppiiagvsas  ygssvrvygh  vsqrwdiigh  cyldiyptnc  yplstkpvag
241  ddevfvkqqg  rqieidsnsp  ivqvvvydle  gksvfrkrmt  enaytlsfra  pmlgfmtimi
301  etqnsiinkk  lnvtql SEQ ID NO:20
PG0614
  1  mpkqyhnkne  hkmkqtilgi  qlsqwtkcfl  sffliagctg  alsgqspsqs  rgyattgile
 61  pvmlpdtvpv  dyhsawgmvc  daqlnafdkp  iafrapfsyq  gkgyyyptay  ygglrefcpy
121  aklgdmlite  grfhefdayy  elmctritlp  nrtfegvvte  ipmpqftype  vtativcvkd
181  dsgfeiaikd  degnfissen  gevmiagnsy  plqtrvrveg  divqdyqlky  piifystvak
241  schttdsqtv  vpssndinvy  iqgttigika  ekliksvyiy  dmagrmlfat  sqtqgrefci
301  dlktkghilv  tvlfadntqt  skniil
```

```
SEQ ID NO:21
PG1795
  1  mkkalligaa llgavsfasa qslstikvqn nsvqqpreea tiqvcgelae qvdcigtgns
 61  aiiaaaakfe sddlesyvgw eimsvdffpg ykackytsav waddmtilgq sedsdpemqt
121  innlalktsv kieagknyiv gyiantaggh pigcdqgpav dgygdlvsis edggatfppf
181  eslhqavptl nyniyvvvhl kkgegveavl tndkanayvq ngviyvagan grqvslfdmn
241  gkvvytgvse tiaapqkgmy ilrvgaksik lai SEQ ID NO:22
PG1102
  1  mgydphvrew klplngkarg ksievsfpyf yradqslkrr ripmphhlls ltsllrcrlh
 61  hfflyiiiiv sagysataqt vikglvlaad neapvsyasi yvaetksgvv adesgrfilr
121  lhpgryrlai rsmgytplet ellvgeksee ktfrlssviy dlkevevigk rpkedpaypi
181  mreliartpv yehmvksyqa kvytkgsmrl dklpfwlryk kadgisakdl ekkrfviesq
241  aslefrhpnk ynkqvramrs sipddlksdt tdymqiistn iyakefsldg ivnmaspirt
301  gvlesytykl egtsrekerk vyhisfkgrr damrgelwvi dsiwclqalk leikaydmir
361  ykvdislnpl ekdvylptty aigmemqsmg lkleyqyfss lvydsleidr kllstarrae
421  glrfrtnrev nrhlrmlesr ldtlgyhlpd kymlpdtelq akvrfdslaf drdssywdav
481  vtapltdeea qsyanrdslm qafekkrrfg ggregertgr tsilgailgg hdykmgegtt
541  lgfngllirgs lydyrytdgf wlgqsfffrq kfskgvdltl rpilyytthr rklywdvrad
601  fryaplsggl lslsagrqsa dltgpfantd wriqtflttl vdgrghlmly dkkylrlsnq
661  idllpglqlf lfaegrhssp laenrvwgif kkpiknklig giasspdsll ysmpdhrslt
721  vggsirynpa pyyrldkdgr krydgvgtra plfgltyrqa iplgrehdsd yiylsgsvrq
781  nlrlnplhsl yyhftvgsyf rrhtvhldeq rylkadnalf qiggtlhdsf qtlppysytd
841  qnflilqtrw sfpslitnpl gilfasfqsn lhlntywgch kdrmpffeig ysrgtiaqig
901  ifcgaynfhk dyglmlryti nfptl SEQ ID NO:23
PG2225
  1  mselrlaims vlmsveeadf lylkevtgat sgnisvqldk lstagyieie kgyngkrprt
 61  tcratdagre afsahfealk sylptdsth SEQ ID NO:24
PG1664
  1  mfdldnlhel gatlrknmlr taltgfavaw gvlllillls agrgfqhgir hnveqfgmgt
 61  saisfstwrt skeyggypkd ryieltpadc dylvklnpdl ikgaayytnq wsydvqyedr
121  thstptkavs geygnmvkth liegrflsts ddamkrkviv lceqtadvlf gesispigky
181  vnlsqipflv vgvckgeqgq fspnyipfat ysgifakgfs ldctlfmncp svrteenver
241  lkvllnrqla frkgydptdm evpyvdapvt dikmmdkifn qmdvflwiig lstlvigiig
301  vanimqvtvn erqreigirk algakpraii nmilteavvv tlfsgligly agvglmefvs
361  hwvqttgvgs rqvegitltl frdpsidlst allalivmvv sgaiagyqpa rkavripave
421  amrn SEQ ID NO:25
PG2224
  1  miekmleqtr krlirgagip sliwgyvtfa tsllilfvyp higyranylw mlipivgggl
 61  tiicnrkrqk eahartqidr fidttwitig lnvtalsila yrfplailpl vliligiata
121  itgfshkvtl lkyssifgil vgymllvvpm sgklmvlifg ltfflmhcvp ghylcylerk
181  ilrda SEQ ID NO:26
PG1724
  1  mkkdiiilgi esscddtsaa vvrnetmlsn viagqavhka yggvvpelas rahqqnivpv
 61  vseaikragi rkeeidaiaf trgpgllgsl lvgtsfakgl slslgipmle vnhlhahvla
121  nflrepgees qhpsfpflcl lvsggnsqii lvrspydmev igqtiddaag eafdkcakvm
181  glgypggpiv nklasegnpd afrfarphvs gydysfsglk tsflytlrdk laedpdfiek
```

```
241 nkadlcaslq htvidilmkk lrqaakdhsi kqvalaggvs antglrdafh dharrygwtv
301 fipkfayttd naamvaisgy ykylqgdfcp idavpfsrit v SEQ ID NO:27
PG0900
1   mnldalvsws raqfaltamy hwlfvpltlg lgvimaivet iyyrngkpew kryaqfwqkl
61  fginfaigva tgiilefefg tnwsnyslfv gdifgaplai egilaffmea tfiavmffgw
121 nkvskgfhls atwltiigas lsavwilian awmqepvgmt fnpdtmrnem tdfwalvfss
181 tainkfwhti sscwtlgsvf algvcgiyll rkddkhkdfa lknikiiapf glaaslitaf
241 tgdtsaynva qkqpmklaam ealydsgqtd kdgltadgkg lplslfgiln paketpqddk
301 eaflfnvsvp rvlsvlgtrn psgyvpginn ileggyvkad gttaipvdsm mqrgrraima
361 lndyskakqa gdmeaalqhk svidenfpyf gysyiqhknd ivppvgltyy sfrimvglgm
421 lfillflmaw llsfkpekfs kmrwfhmiai vcmplawvas qsgwivaevg rqpwtiqdll
481 pvqaavskle agsviitffv flvlfsallv aelnimrkai kkgpete SEQ ID NO:28
PG1279
1   mtkvlvatek pfakvavdgi kriieeagle fallekytdk kqlldavkda naiiirsdqi
61  daevldaake lkivvragag ydnvdlaaat ahnvcvmntp gqnsnavael vmgmlvfmyr
121 nlfngasgse lmgkklgila ygnvgrnvar iakgfgmeiy aydqfvsaad iekegvkava
181 srdalfetcd ivslhipktp etvksinael lskmpkgacl intarqevid eegickfmae
241 rtdfkyatdi kptndaemak fegryfttpk kmgaqtaean inaglaaarq ivdfikngne
301 kfrvnk SEQ ID NO:29
PG1280
1   maiikpfkgv rppkelveqv asrpydvlns eearkeakgn ekslyhiirp eidfpvgkde
61  hdadvyekaa enfrmfqekg wlvqdtkeny yvyaqtmngk tqyglvvgay vedymngvik
121 kheltrrdke edrmkhvrvn daniepvffa ypenkeldai vkkyaarpae ydfvaefdgf
181 ghhfwvidee adikritelf aampalyiad ghhrsaaaal vgaekaknnp nhrgdeeyny
241 fmavcfpadq ltiidynrvv kdlnglsdee flqklsrhfe veckgteeyr psklhnfsly
301 lggkwyslta kagtyddndp igvldvtiss nlildeilgi kdlrsdkrid fvggirglge
361 lkkrvdsgem rvalalypvs mkqlmdiads gnimppkttw fepklrsgli ihkls
```

Figure 9

PG0120 - Putative identification: UDP-N-acetylglucosamine 2-epimerase

SEQ ID NO: 30

ATGAAAAAAGTGATGTTGGTCTTCGGGACGAGACCCGAAGCGATCAAGATG
GCTCCGCTGGTGAAGGAATTTCAAGCGAGAGCAAGTGAGTTTGATACCATT
GTCTGTGTGACGGGTCAGCATAGAGAGATGCTCAAGCAAGTGCTGGAGCTA
TTTGATATCAAGCCCGATTATGACTTGGAGATCATGAAGGAGGGGCAGGAT
CTCTATGACGTAACTACACGTGTGCTGTTGGGTATGCGTGAAGTACTCAAGA
AGACAAAGCCCGATGTAGTACTCGTACACGGCGATACGACTACAAGTACTG
CCGCTGCATTGGCTGCTTTCTATCAACAGATTCCGGTAGGACATGTGGAGG
CAGGGCTTCGCACGCACAACATTTACAGCCCATGGCCGGAAGAGATGAACC
GTCAGCTCACCGGTAGGATGGCTACCTATCACTTTGCTCCTACGGAATTGA
GTCGGGACAATTTACTTGCAGAAGGGATTGCTACAGATCGTATATTTATTAC
AGGAAATACAGTAATCGATGCTCTACAACAAGTCGTTACACGAGTTAAGGGT
AATGCCGATTTGCGAAATCAAGTGTCTCGAAAGCTACTTCAATTTGGATATG
ATGTGAATCGTTTAGAGGCTGGGCGTAGACTTGTTCTTATCACAGGGCATC
GCAGAGAAAACTTTGGCGAAGGATTCCTTAATATCTGCCGTGCTATTCAAAC
TCTTAGCAAGCGTTTCCCGGAGGTAGACTTTGTTTATCCCATGCACCTTAAC
CCCAATGTGCGTAAGCCTATTCGCGAGATCTTCGGCGATAACCTTGGAGGC
TTGGATAATCTCTTTTTTATTGAGCCGCTGGAGTATTTGCAGTTTGTTACGCT
CATGGATCGTTCGTCCATTGTTCTGACTGATAGTGGAGGTATTCAGGAAGAA
GCTCCAGGGTTAGGCAAACCTGTATTGGTAATGCGAGATACTACGGAGCGT
CCCGAAGCGGTGAAAGCAGGAACCGTGAAACTTGTAGGGACAGATTATAAT
CAAATCGTCGACAATGTCGAAAAACTACTGACAGACAACGCCGCATATGCC
GAAATGAGCAGAGCCAATAATCCGTACGGTGACGGAAAGCATGCTCATAT
ATAGCGGATGCTCTTACTCGATGCATTTAG

SEQ ID NO:31

MKKVMLVFGTRPEAIKMAPLVKEFQARASEFDTIVCVTGQHREMLKQVLELFDI
KPDYDLEIMKEGQDLYDVTTRVLLGMREVLKKTKPDVVLVHGDTTTSTAAALAA
FYQQIPVGHVEAGLRTHNIYSPWPEEMNRQLTGRMATYHFAPTELSRDNLLAE
GIATDRIFITGNTVIDALQQVVTRVKGNADLRNQVSRKLLQFGYDVNRLEAGRRL
VLITGHRRENFGEGFLNICRAIQTLSKRFPEVDFVYPMHLNPNVRKPIREIFGDN
LGGLDNLFFIEPLEYLQFVTLMDRSSIVLTDSGGIQEEAPGLGKPVLVMRDTTER
PEAVKAGTVKLVGTDYNQIVDNVEKLLTDNAAYAEMSRANNPYGDGKACSYIA
DALTRCI

PG0186 - Putative identification: lipoprotein RagB

SEQ ID NO:32

ATGAAAAAAATAATTTATTGGGTTGCGACAGTTTTCTTAGCAGCGAGCGTAT
CCTCTTGCGAGCTTGACCGCGACCCCGAAGGAAAAGATTTCCAACAGCCAT
ATACTTCTTTCGTGCAGACGAAACAAAACAGAGATGGTCTTTACGCACTTTT
GCGTAATACTGAAATCCACGAATGCATTTTATCAGGAACTTCAATCCGAT
ATGTATTGCACTACCATTACTGATGGTAACTCCTTAGCTCCGTTCGTGAATT
GGGATTTAGGCATACTTAACGACCATGGACGTGCTGATGAGGACGAAGTCT
CCGGTATAGCTGGCTACTATTTCGTATACAATCGACTAAATCAGCAAGCGAA
TGCTTTTGTTAACAATACGGAAGCTGCTTGCAGAATCAAGTGTATAAAAAT
TCCACCGAGATCGCCAATGCTAAGAGCTTTTGGCGGAAGGAAAAGTTTTA
CAAGCATTGGCTATTTGGCGACTGATGGATCGTTTTAGCTTCCATGAAAGCG
TGACAGAAGTTAATTCCGGTGCGAAAGATCTTGGCGTTATTCTGTTGAAAGA
ATATAATCCTGGTTATATCGGTCCCCGTGCAACGAAGGCACAATGTTATGAT
TACATTTTGTCACGTTTGTCTGAGGCTATTGAAGTTTTGCCCGAAAACAGGG
AAAGCGTTCTTTATGTGAGCCGTGATTACGCCTATGCCCTCCGAGCAAGAAT
TTACCTCGCGTTGGGTGAATATGGAAAAGCTGCAGCAGATGCTAAGATGGT
TGTTGATAAGTATCCTTTGATTGGTGCAGCAGATGCTTCTGAGTTTGAGAAT
ATTTATCGATCAGATGCTAATAATCCCGAAATTATTTTCGTGGTTTTGCTTC
TGCGACTCTTGGCTCGTTTACTGCTACGACACTAAATGGTGCTGCGCCAGC
AGGTAAGGATATAAAATATAATCCGAGCGCAGTCCCTTTCCAATGGGTAGTG
GATCTTTATGAAAACGAAGATTTCCGCAAATCCGTATATATCGCGAAAGTTG
TGAAAAAGGATAAGGGGTATTTAGTAAATAAATTCCTTGAGGACAAGGCTTA
TCGTGATGTTCAGGATAAGCCAAACCTTAAAGTCGGAGCTCGTTATTTTAGC
GTTGCTGAGGTCTACTTAATTTTGGTAGAGTCTGCTCTTCAGACTGGAGATA
CCCCAACAGCCGAAAAATATCTCAAGGCTTTGAGTAAAGCTCGTGGAGCAG
AAGTTTCAGTCGTTAATATGGAAGCACTGCAAGCAGAGCGTACGCGTGAGC
TTATAGGTGAGGGTAGTCGTTTGCGTGATATGGTCCGCTGGAGTATCCCTA
ATAATCATGATGCTTTTGAGACTCAGCCTGGTTTAGAAGGTTTTGCAAATACT
ACTCCTTTGAAAGCTCAAGCTCCTGTAGGCTTTTATGCATATACTTGGGAGT
TCCCACAGCGAGATCGACAAACTAATCCGCAGTTAATAAAGAACTGGCCGA
TATAA

SEQ ID NO:33

MKKIIYWVATVFLAASVSSCELDRDPEGKDFQQPYTSFVQTKQNRDGLYALLR
NTENPRMHFYQELQSDMYCTTITDGNSLAPFVNWDLGILNDHGRADEDEVSGI
AGYYFVYNRLNQQANAFVNNTEAALQNQVYKNSTEIANAKSFLAEGKVLQALAI
WRLMDRFSFHESVTEVNSGAKDLGVILLKEYNPGYIGPRATKAQCYDYILSRLS
EAIEVLPENRESVLYVSRDYAYALRARIYLALGEYGKAAADAKMVVDKYPLIGAA
DASEFENIYRSDANNPEIIFRGFASATLGSFTATTLNGAAPAGKDIKYNPSAVPF
QWVVDLYENEDFRKSVYIAKVVKKDKGYLVNKFLEDKAYRDVQDKPNLKVGAR

YFSVAEVYLILVESALQTGDTPTAEKYLKALSKARGAEVSVVNMEALQAERTRE
LIGEGSRLRDMVRWSIPNNHDAFETQPGLEGFANTTPLKAQAPVGFYAYTWEF
PQRDRQTNPQLIKNWPI

PG0280 - Putative identification: ABC transporter, permease protein, putative

SEQ ID NO:34

ATGCTACATCATATTATCAAGATCATCCGCGCCGAACGTCGTGCCAACCTCT
GGATATGGCTGGAGATGCTCGTCGTATGTGGCCTGCTTTGGTTCGTCACGG
ACTATGCCGTGACAGCTCTGCGTGCTTGGACACGCCCATTGAACTACGATA
TAGAACACGTGTACCGCATCACGCTGGCAACCGTACAAAAGATAAGGATG
GAAAATGGAAAGAGAGGTCTGCGGATCAGGGAAAAACCATGATGCAAACCC
TCGATCTGATCGCTGCATATCCCGGAGTGGAAGCGGCTTGTCTCCAACAGT
GGGGCGGTCATTATTCCTCTTCGTCAAGTAACAGTAGCTTTCAACTGGACAC
CGTATCACTCATAAACGTTGAGGATCGAATGGTTTCGCCGGATTATTTCCGT
GTATTTCGTGTCTATGGAGCCGATGGTTCTTCGCCGGAAGAGATGGCGGAA
CGATTCGGCAAACTTCACATGAACGATCTCCAACGGGACTACTATCTCTCGC
GCAATGCCCTCGACTATGTGGAGAAAGTCAATGGCGAAGGACGAGAAAGC
GACCGCCGCTACATAGGCATGTCGGATAGCATCAACTACAATATGGTATCC
GTTGTCGATGGCGTCCAAAGCGAAAAGAGTATCCGATACAATCAGACACTG
CGAGGACTCATACCGGATCAGCCCAAAAACGAAGCCGAAAGTACCGGCTAT
ATCAGCCTAAAGCCCATCACCGAGGAGTACATTTCGCAAAACGAACTCATAT
CTTACTCCGTCTATCTGCGTGTCTCTCCCGAAGCGGATACGCCGGACTTCA
AAGAGCAGTTCGTGAAAAGGATGAAAGCCGTGACCAAGGACGATACCTATC
CTGTACTGACGATGAATGCTGTCAGTGAAGACCGGGCAGGGATATTGGCCG
ATCCTGTCCGGCAGATCAATAATCATCTGGCCATCGGTTTCTTCCTTCTGCT
CAATATATTCCTCGGTATCGTCGGCACCTTCTGGGTGCGAACCGAGCAGCG
ACGCGCCGAAGTAGGAATCCGCCGTGTAGTGGGATCCACGAACAGGAGCG
TATTCTCGCTCATGTTCGGCGAGGGGATTATACTGATGACACTGGCTTTCCT
GCCTGCGGCCGTAGCCGCATGGTACGTCATGTTCCATACCGATCTTTGCGA
CATCAAGGTGTTTCCTCTCGGCCGGGGACGTCTTTTGCTCGGATTGGGGTG
TACTTATTTGCAGATGCTGCTGATGGTTTTTCTCGGTACTTTCATTCCCGTAC
TGCGTGCTTTGCGTGTGCCTCCGACCGAAGCTATCCGCAGCGAGTAG

SEQ ID NO:35

MLHHIIKIIRAERRANLWIWLEMLVVCGLLWFVTDYAVTALRAWTRPLNYDIEHV
YRITLATVQKDKDGKWKERSADQGKTMMQTLDLIAAYPGVEAACLQQWGGHY
SSSSSNSSFQLDTVSLINVEDRMVSPDYFRVFRVYGADGSSPEEMAERFGKLH
MNDLQRDYYLSRNALDYVEKVNGEGRESDRRYIGMSDSINYNMVSVVDGVQS
EKSIRYNQTLRGLIPDQPKNEAESTGYISLKPITEEYISQNELISYSVYLRVSPEAD
TPDFKEQFVKRMKAVTKDDTYPVLTMNAVSEDRAGILADPVRQINNHLAIGFFLL

LNIFLGIVGTFWVRTEQRRAEVGIRRVVGSTNRSVFSLMFGEGIILMTLAFLPAA
VAAWYVMFHTDLCDIKVFPLGRGRLLLGLGCTYLQMLLMVFLGTFIPVLRALRV
PPTEAIRSE

PG1321 -- Putative identification: formate--tetrahydrofolate ligase

SEQ ID NO:36

ATGAAATCGGACATTCAGATTGCACGTGACATCGAACTGCAAAGAATCGAAC
AGATAGCAGAGTCAATCGACTTGCCTGTCGAACAATTAGAACCATACGGAAT
ACACGGCCAAAGTGCCGCTAAGCTGTATCGACGAAGAGAAAGTAAAAAAGG
GAAATCTGATTCTGGTGACAGCCATTACGCCGAACAAGGCCGGTGTGGGAA
AAACCACTGTCTCCATCGGATTGGCTCTGGGACTCAACCATATCGGGAAGT
CGTAGCCTTGCGCGAACCTTCGCTCGGACCTTGCTTCGGTATGAAAGGGGG
GGCTGCCGGAGGTGGCTATGCACAGGTACTGCCCATGGAGAACATCAACC
TCCACTTCACCGGTGATTTCCATGCTGTCACTTCGGCTCACAACATGATTAC
GGCTCTTTTGGAGAACTATATTTATCAGAACCGCAATACTTGCGACGGCCTC
TCCGAAATACTTTGGAAGCGTGTACTGGACGTTAACGACCGCTCTTTGCGC
AATGCCGTTACGGGGTTGGGTACCATCTCGGACGGAATACCTCGCCAGACC
GGTTTTGACATTACGCCGGCTTCCGAGATCATGGCTATCCTCTGTCTGGCC
AAAGACTTTGAAGACCTCCGCAGCCGTCTTGAAATATTCTTCTCGGCTATA
CCAAAGAAGGTGCTCCCTTTACGGTCAAAGACCTCGGCATAGCAGGATCCA
TTGCCGTCTTGCTCAAGATGCCATAAAGCCTAATCTGGTACAGACCACAGA
GCACACTCCGGCATTTGTACATGGAGGCCCCTTTGCCAATATCGCACATGG
CTGTAACTCCATCTTGGCCACAAAGATGGCTCTCTCTTTCGGCGAATATGCC
GTCACCGAGGCCGGTTTCGGTGCAGATCTGGGTGCAGAAAAATTCCTTGAC
ATCAAATGTCGGGAAATGGGTGTCGCACCCAAGCTTACCGTCCTCGTGGCC
ACGCTGCGCGCGCTCAAATTGCATGGCGGCGTTGCCGAAACGGAAATCAA
GGCACCCAATGCCGAAGCTCTCAGAAGAGGTTTGTCCAATCTGGATCGCCA
CATATACAATCTGAAAAAATTCGGTCAGCAAGTAATCGTTGCATTCAACCGC
TTCGACACCGACGAAGAAGAAGAGATCAGCATCGTTCGTGAGCATTGTATC
GGGCAAAATGTCGGCTTCGCTGTGAACAACGCCTTTGCAGAAGGCGGAAAA
GGTGCGGAAGAACTGGCAAAACTTGTTGTGGAAATGGTAGAGAATAAACCC
TCCAGCCTCTGAAATATGCCTATGAGCCGGAGAATCCCGTGAAAATGAAG
ATCGAGAAGATCGCCAAGGAAATATACAGCGCAGGGAGTGTAGTGTATAGC
TCCAAAGCAGACGGCAAGCTCAAAAAGATTGCCATGCAATCGCTGGATCAT
CTCCCCGTTTGTATTGCCAAGACGCAGTACTCTTTCTCATCCGACCCCAAAG
CCAAGGGAGATGTCAGAGGGTTTGAGCTCAAAGTATCCGACATCATCATCA
ACCGTGGAGCAGGCATGCTGGTCGTTATCATCGGAGAGATCATGCGTATGC
CCGGACTCCCCAAAGAACCGCAAGCTGTACATATAGATATAGTAGACGGTT
TCATCGAAGGCCTTAGCTGA

SEQ ID NO:37

MKSDIQIARDIELQRIEQIAESIDLPVEQLEPYGRYTAKVPLSCIDEEKVKKGNLIL
VTAITPNKAGVGKTTVSIGLALGLNHIGKKAIVALREPSLGPCFGMKGGAAGGG
YAQVLPMENINLHFTGDFHAVTSAHNMITALLENYIYQNRNTCDGLSEILWKRVL
DVNDRSLRNAVTGLGTISDGIPRQTGFDITPASEIMAILCLAKDFEDLRSRLENIL
LGYTKEGAPFTVKDLGIAGSIAVLLKDAIKPNLVQTTEHTPAFVHGGPFANIAHG
CNSILATKMALSFGEYAVTEAGFGADLGAEKFLDIKCREMGVAPKLTVLVATLR
ALKLHGGVAETEIKAPNAEALRRGLSNLDRHIYNLKKFGQQVIVAFNRFDTDEEE
EISIVREHCIGQNVGFAVNNAFAEGGKGAEELAKLVVEMVENKPSQPLKYAYEP
ENPVKMKIEKIAKEIYSAGSVVYSSKADGKLKKIAMQSLDHLPVCIAKTQYSFSS
DPKAKGDVRGFELKVSDIIINRGAGMLVVIIGEIMRMPGLPKEPQAVHIDIVDGFI
EGLS

GENES OF *PORPHYROMONAS GINGIVALIS* W83 INVOLVED IN INVASION OF HUMAN CELLS

PRIORITY

This application claims the benefit of U.S. Appl. Ser. No. 60/648,765, filed Feb. 1, 2005, which is incorporated herein by reference in its entirety.

GOVERNMENT INTERESTS

This invention was made with Government support under Grant Number DE13545 awarded by the National Institute of Dental and Craniofacial Research. The Government has certain rights in the invention.

BACKGROUND OF THE INVENTION

Cardiovascular disease (CVD) is the leading cause of death in the United States, however, the classic risk factors do not explain all of its clinical and epidemiological features (Leaverton et al., *J. Chronic. Dis.* 40:775-784 (1987)). An increasing body of evidence suggests that bacterial infections also play a role. Low-grade infections have been associated with CVD and studies indicate that chronic infections, including those of the oral cavity, increase the risk of CVD. (Haverkate et al., *Lancet* 349: 462-466 (1997); Mattila et al., *Clin. Infect. Dis.* 26:719-734 (1998); Beck et al., *J. Periodontol.* 67:1123-1137 (1996)). It has been proposed that some risk factors are shared by periodontal disease and heart disease indicating a possible common etiologic pathway.

In a recent report, Haraszthy et al., (*J. Periodontol.* 71:1554-1560 (2000)) suggested that certain species of periodontal pathogenic bacteria may be involved in CVD. Additionally, *Porphyromonas gingivalis, Prevotella intermedia, Actinobacillus actinomycetemcomitans* and *Bacteroides forsythus* were detected within atheromatous plaques. *P. gingivalis* (Pg) is one of the major pathogens associated with adult periodontitis (Socransky et al., *J. Periodontol.* 63:322-331 (1992)) and, due to transient bacteremias, have a route to the circulatory system in periodontitis patients (Sconyers et al., *J. Am. Dent. Assoc.* 87:616-622 (1973); Silver et al., (*J. Clin. Periodontol.* 4:92-99 (1977)). Some studies have demonstrated that Pg internalizes within gingival epithelial cells in vitro and in vivo as well as within coronary endothelial cells in vitro (Lamont et al., *Oral Microbiol. Immunol.* 7:364-367 (1992); Sandros et al., *J. Periodontal Res.* 28:19-226 (1993); Rudney et al., *Infect. Immun.* 69:2700-2707 (2001); Deshpande et al., *Infect. Immum.* 66:5337-5343 (1998); Dorn et al., *Infect. Immun.* 67:5792-5798 (1999)). Thus, the inflammatory response of atherosclerosis may be a result of invasion by Pg within endothelial cells. Identification of polynucleotides and polypeptides in the invasive mechanism of Pg is needed. Mutational analyses are currently in progress to understand the role of genes in invasion ability of Pg. The knowledge of the role of these genes may offer insight into disease mechanisms and the interactions between bacteria and host. Thus, potential therapeutic interventions may be developed.

SUMMARY OF THE INVENTION

One embodiment of the invention provides an antigenic composition comprising at least one purified recombinant polypeptide that specifically binds to an antibody or fragment thereof, wherein the antibody or fragment thereof specifically binds to a polypeptide consisting essentially of SEQ ID NOs: 2, 4, 6, 8, 10, 11-29, 31, 33, 35, 37 or a combination thereof and an adjuvant.

Another embodiment of the invention provides a method for determining the presence or absence of an antibody or fragment thereof, in a test sample, where in the antibody or fragment thereof specifically binds to a polypeptide comprising SEQ ID NOs: 2, 4, 6, 8, 10, 11-29, 31, 33, 35, or 37. The method comprises contacting the test sample with a purified polypeptide comprising SEQ ID NOs: 2, 4, 6, 8, 10, 11-29, 31, 33, 35, or 37 under conditions suitable for specific binding of the purified polypeptide to the antibody or fragment thereof and detecting the presence or absence of specific binding. The presence of specific binding indicates the presence of the antibody or fragment thereof, and the absence of specific binding indicates the absence the antibody or fragment thereof. The method can further comprise detecting the amount of specific binding. The test sample can be a serum, blood, saliva, or plaque sample. The purified polypeptide can be immobilized to a solid support. The purified polypeptide can be labeled. The detection can be by radioimmunoassay, enzyme-linked immunosorbent assay, immunohistochemical or immumoenzyme-assay.

Even another embodiment of the invention provides a method for determining the presence or absence of a polypeptide comprising SEQ ID NOs:2, 4, 6, 8, 10, 11-29, 31, 33, 35, or 37 in a test sample. The method comprises contacting the test sample with an antibody or fragment thereof that specifically binds a polypeptide consisting essentially of SEQ ID NOs: 2, 4, 6, 8, 10, 11-29, 31, 33, 35, or 37 under conditions suitable for specific binding of the polypeptide to the antibody or fragment thereof and detecting the presence or absence of specific binding. The presence of specific binding indicates the presence of the polypeptide and the absence of specific binding indicates the absence of the polypeptide. The method can further comprise detecting the amount of specific binding. The test sample can be serum, blood, saliva, or plaque. The antibody or fragment thereof can be immobilized to a solid support and can be labeled. The detection can be by radioimmunoassay, enzyme-linked immunosorbent assay, or enzyme-assay.

Yet another embodiment of the invention provides an isolated recombinant *Porphyromonas gingivalis* organism, wherein the recombinant *Porphyromonas gingivalis* organism is genetically engineered to remove one or more of the polynucleotide sequences encoding a polypeptide consisting essentially of SEQ ID NOs:2, 4, 6, 8, 10, 11-29, 31, 33, 35, or 37.

Still another embodiment of the invention provides an antibody or fragment thereof that specifically binds a polypeptide consisting essentially of SEQ ID NOs: 2, 4, 6, 8, 10, 11-29, 31, 33, 35, or 37. The antibody can be a single chain antibody, a monoclonal antibody, or a polyclonal antibody.

Another embodiment of the invention provides a method for detecting the presence or absence of an invasive *Porphyromonas gingivalis* infection in an animal comprising contacting a test sample from the animal with a purified polypeptide comprising SEQ ID NOs:2, 4, 6, 8, 10, 31, 33, 35, or 37 under conditions suitable for specific binding of the purified polypeptide to an antibody or fragment thereof in the test sample, and detecting the presence or absence of specific binding. The presence of specific binding of the purified polypeptide and the antibody or fragment thereof indicates the presence of invasive *Porphyromonas gingivalis* and the absence of specific binding indicates the absence of invasive *Porphyromonas gingivalis*. The method can further comprise detecting the amount of specific binding. The test sample is can be serum, blood, saliva, or plaque. The polypeptide can be immobilized to a solid support and can be labeled. The detection can be by radioimmunoassay, enzyme-linked immunosorbent assay, or enzyme-assay.

Even another embodiment of the invention provides a method for detecting an invasive *Porphyromonas gingivalis* polypeptide comprising contacting a test sample with an antibody or fragment thereof that specifically binds a polypeptide consisting essentially of SEQ ID NOs:2, 4, 6, 8, 10, 31, 33, 35, or 37 under conditions suitable for specific binding of the antibody or fragment thereof to the invasive *Porphyromonas gingivalis* polypeptide and detecting the presence or absence of specific binding. The presence of specific binding indicates the presence of the invasive *Porphyromonas gingivalis* polypeptide and the absence of specific binding indicates that the absence of the invasive *Porphyromonas gingivalis* polypeptide. The method can further comprise detecting the amount of specific binding. The test sample can be serum, blood, saliva, or plaque. The antibody or fragment thereof can be immobilized to a solid support and can be labeled. The detection can be by radioimmunoassay, enzyme-linked immunosorbent assay, or enzyme-assay.

BRIEF DESCRIPTION OF THE DRAWINGS

FIG. 7 shows Pg polypeptides and polynucleotides of the invention.

FIG. 8 shows Pg polypeptides of the invention. Polynucleotides encoding the polypeptides are publicly available at, inter alia, The Institute of Genomic Research TIGR database.

FIG. 9 shows Pg polypeptides and polynucleotides of the invention.

DETAILED DESCRIPTION OF THE INVENTION

Polypeptides

Figure 1:
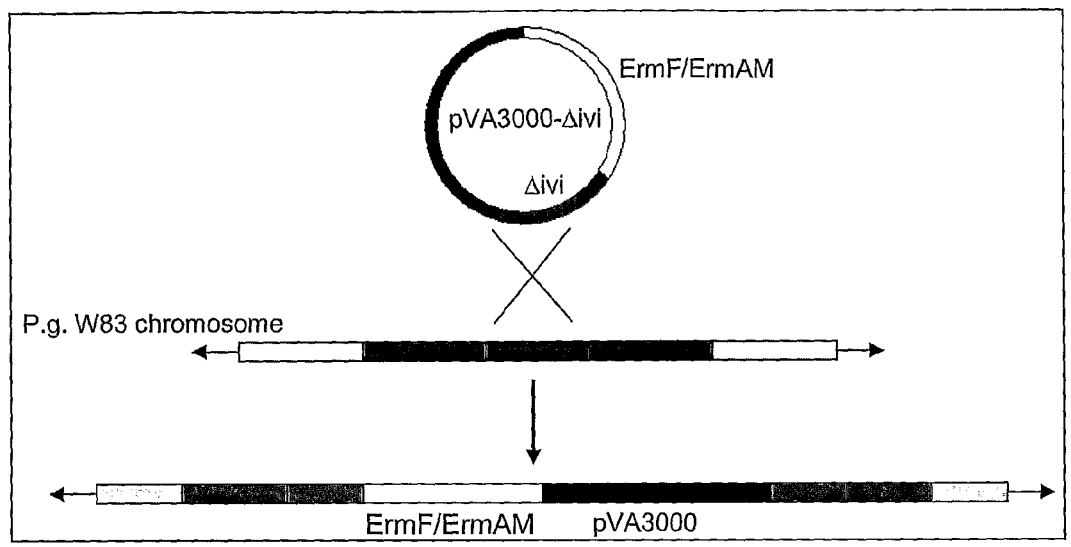
FIG. 1 shows homologous recombination of pVA3000 containing a cloned internal fragment into the W83 chromosome.
Figure 2:
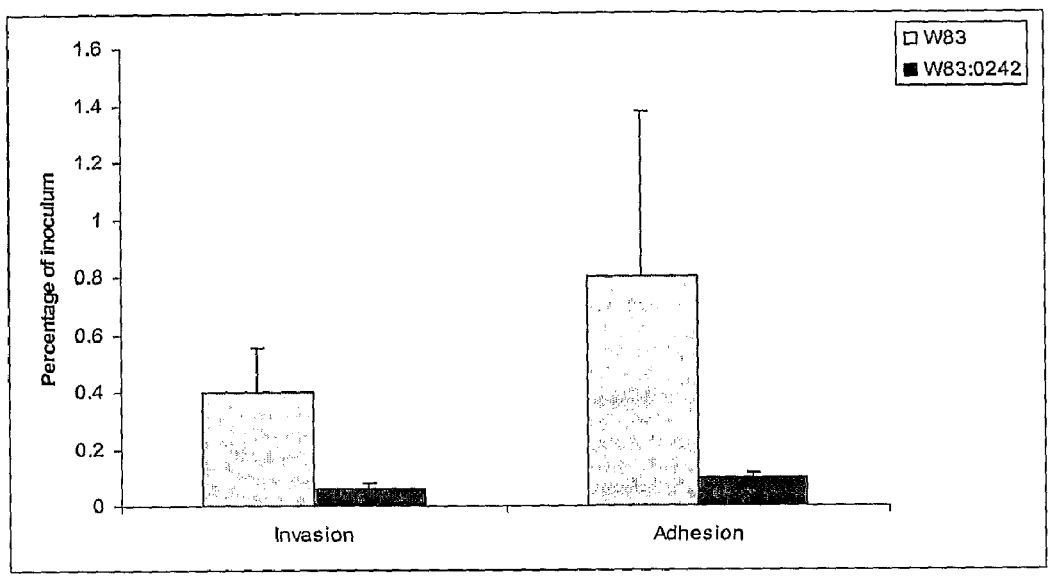
FIG. 2 shows invasion ability of the *P. gingivalis* mutant W83:0242 expressed as the percentage of inoculum. Mutant W83:0242 invades 6.1 fold less than wild type and adheres 11.7 fold less (p<0.01).
Figure 3:
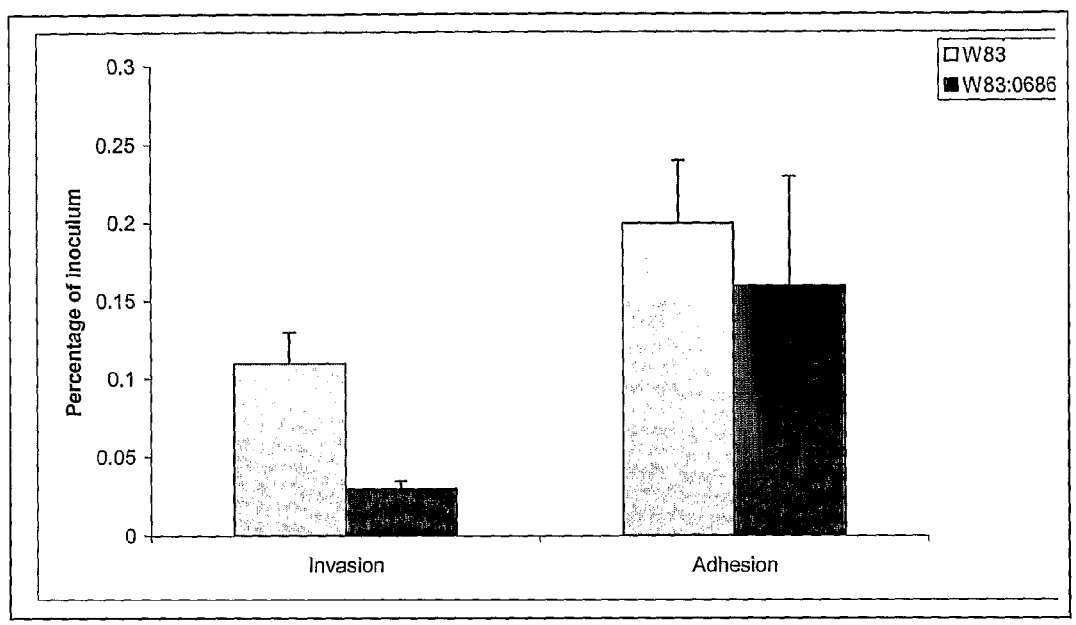
FIG. 3 shows invasion ability of the *P. gingivalis* mutant W83:0686 expressed as the percentage of inoculum. Mutant W83:0686 invades 3.0 fold less (p<0.02) than wild type, but there is no difference in adherence.
Figure 4:
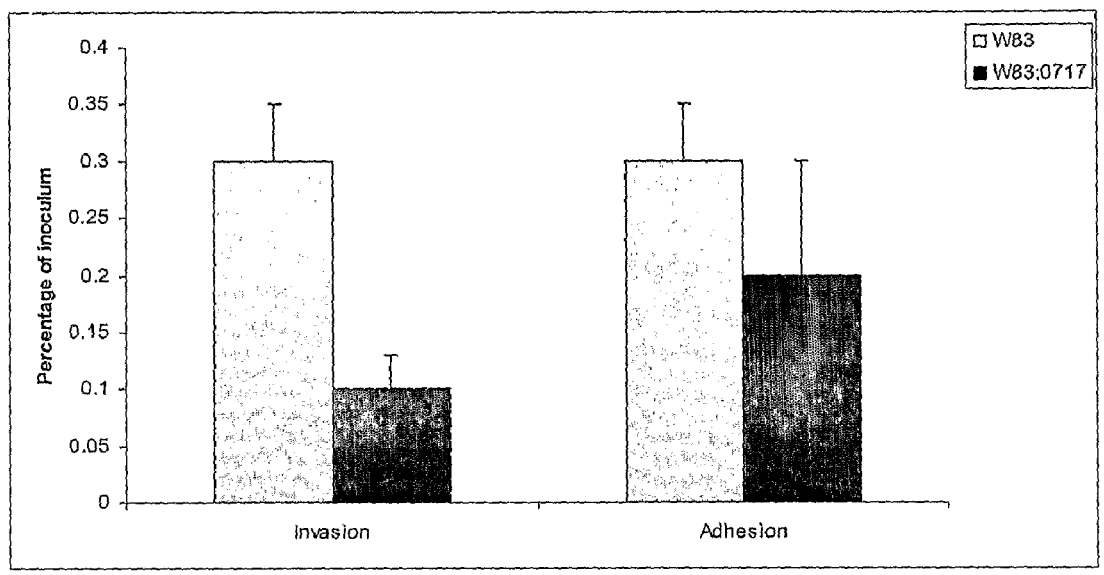
FIG. 4 shows invasion ability of the *P. gingivalis* mutant W83:0717 expressed as the percentage of inoculum. Mutant W83:0717 invades 2.7 fold less (p<0.01) than wild type, but there is no difference in adherence.
Figure 5:
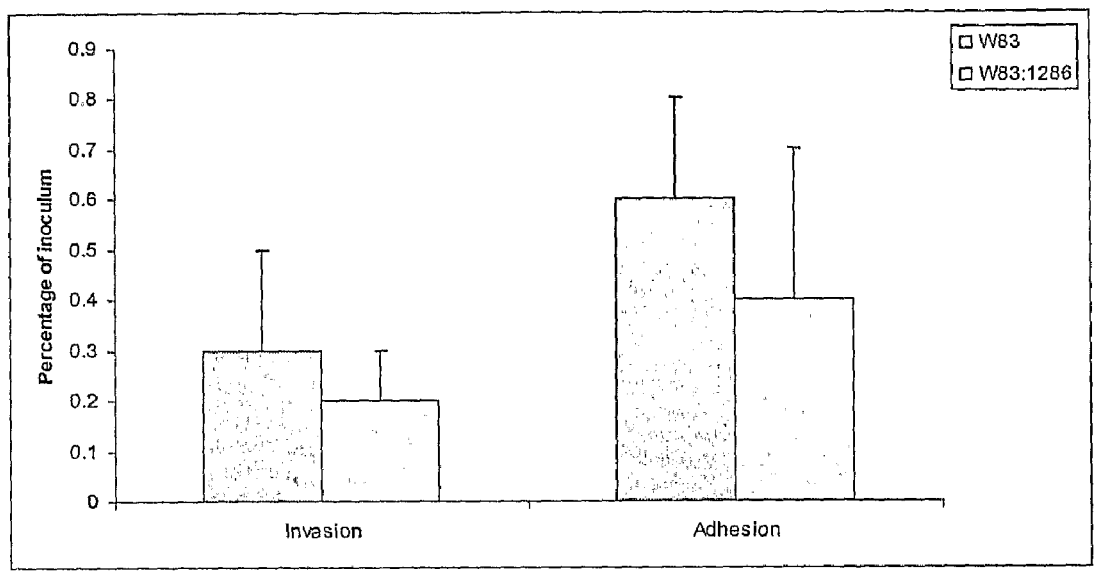
FIG. 5 shows invasion ability of the *P. gingivalis* mutant W83:1286 expressed as the percentage of inoculum. Mutant W83:1286 invades 1.7 fold less (p<0.04) than wild type, but there is no difference in adherence.
Figure 6:
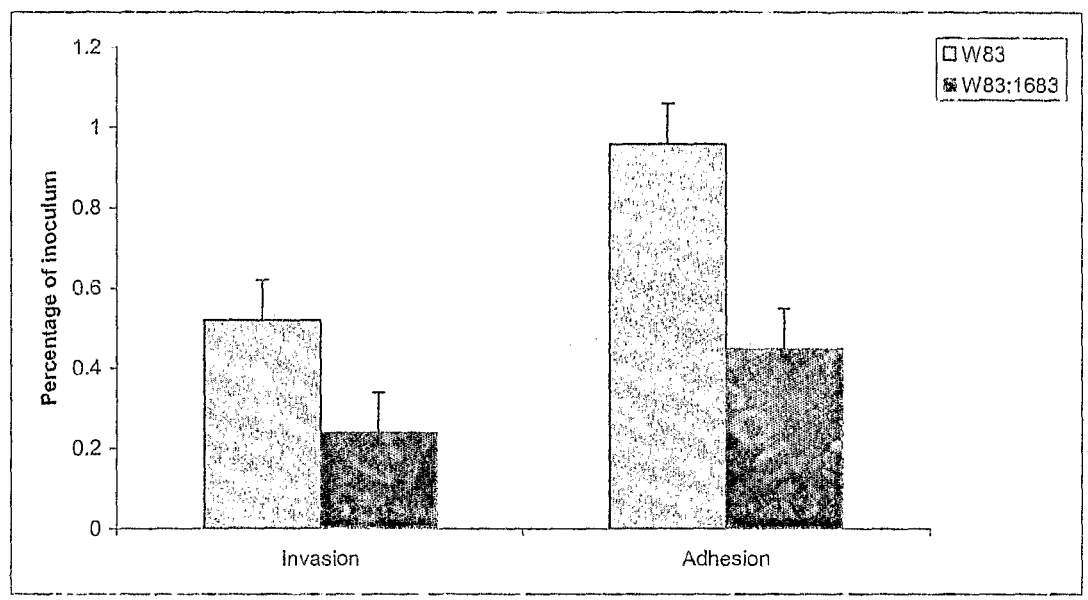
FIG. 6 shows invasion ability of the *P. gingivalis* mutant W83:1683 expressed as the percentage of inoculum. Mutant W83:1683 invades 1.8 fold less (p<0.04) than wild type and adheres 2.1 fold less (p<0.02).

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, or 5% of other polypeptides, culture medium, chemical precursors, and other chemicals used in synthesis. Therefore, a purified polypeptide is about 70%, 80%, 90%, 95%, 99% or more pure.

Purified polypeptides of the invention can either be full-length polypeptides or fragments of polypeptides. For example, fragments of polypeptides of the invention can comprise about 5, 10, 25, 50, 100, 200, 300, 400, 500 or more amino acids of polypeptides of the invention. Examples of polypeptides of the invention include those shown in SEQ ID NO:2, 4, 6, 8, 10, 11-29, 31, 33, 35, and 37. Variant polypeptides are at least about 90, 96, 98, or 99% identical to the polypeptide sequences shown in the polypeptide SEQ IDs are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 5, 10, 25, or 50 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. More than one polypeptide of the invention can be present in a fusion protein. Fragments of polypeptides of the invention can be present in a fusion protein of the invention. A fusion protein of the invention can comprise one or more of SEQ ID NOs:2, 4, 6, 8, 10-29, 31, 33, 35, 37 or fragments thereof, or combinations thereof.

Polypeptides of the invention can be in a multimeric form. That is, a polypeptide can comprise one or more copies of SEQ ID NOs:2, 4, 6, 8, 10-29, 31, 33, 35, 37 or a combination thereof. A multimeric polypeptide can be a multiple antigen peptide (MAP). See e.g., Tam, J. Immunol. Methods, 196:17-32 (1996).

The basic and novel characteristics of a polypeptide of the invention is that it specifically binds an antibody, wherein the antibody is specific for a Pg antigenic determinant; and the polypeptide is necessary to retain wild type levels of Pg adherence and invasive activity in a Pg organism.

Polypeptides of the invention can comprise an antigen that is recognized by an antibody reactive against Pg. The antigen can comprise one or more epitopes (or antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay a Pg polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from Pg cells.

An immunogenic polypeptide of the invention can comprise the amino acid sequence shown in SEQ ID NOs:2, 4, 6, 8, 10, 11-29, 31, 33, 35, or 37. An immunogenic polypeptide can elicit antibodies or other immune responses (e.g., T-cell responses of the immune system) that recognize epitopes of polypeptides having SEQ ID NOs:2, 4, 6, 8, 10, 11-29, 31, 33, 35, or 37. An immunogenic polypeptide of the invention can also be a fragment of a polypeptide that has an amino acid sequence shown in SEQ ID NOs: 2, 4, 6, 8, 10, 11-29, 31, 33, 35, or 37. An immunogenic polypeptide of the invention can be about 10, 20, 30, 40, 50 or more amino acids in length.

Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode polypeptides shown in SEQ ID NOs:2, 4, 6, 8, 10, 11-29, 31, 33, 35, 37 or combinations thereof. In one example, the polynucleotides comprise SEQ ID NOs:1, 3, 5, 7, 9, 30, 32, 34, and 36. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid existing among hundreds to millions of other nucleic acid molecules within, for example, cDNA or genomic libraries, or gel slices containing a genomic DNA restriction digest are not to be considered an isolated polynucleotide.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the sequence given in the polynucleotide SEQ IDs, due to the degeneracy of the genetic code. Complementary DNA (cDNA) molecules, species homologs, and variants of Pg polynucleotides that encode biologically functional Pg polypeptides also are Pg polynucleotides. A polynucleotide of the invention can comprise about 21, 24, 27, 30, 40, 50, 100, 200, 300, 400, 500, 1,000 or more nucleotides of a polynucleic acid sequence of the invention.

Polynucleotides of the invention can be isolated from nucleic acid sequences present in, for example, a biological sample, such as plaque, blood, serum, saliva, or tissue, from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to one or more expression control elements, which direct transcription and/or translation of the polynucleotide.

Polynucleotides of the invention can be used, for example, as probes or primers, for example PCR primers, to detect the presence of Pg polynucleotides in a sample, such as a biological sample. The ability of such probes and primers to specifically hybridize to Pg polynucleotide sequences will enable them to be of use in detecting the presence of complementary sequences in a given sample. Polynucleotide probes and primers of the invention can hybridize to complementary sequences in a sample such as a biological sample, including plaque, saliva, crevicular fluid, sputum, blood, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging form about 20° C. to about 55° C. The presence of a hybridized complex comprising the probe or primer and a complementary polynucleotide from the test sample indicates the presence of Pg or a Pg polynucleotide sequence in the sample.

Antibodies

Antibodies of the invention are antibody molecules that specifically and stably bind to a Pg polypeptide of the invention or fragment thereof. An antibody of the invention can be a polyclonal antibody, a monoclonal antibody, a single chain antibody (scFv), or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., a polypeptide, recognizes and binds to an antibody of the invention with greater affinity than to other, non-specific molecules. A non-specific molecule is an antigen that shares no common epitope with the first antigen. For example, an antibody raised against an antigen (e.g., a polypeptide) to which it binds more efficiently than to a non-specific antigen can be described as specifically binding to the antigen. In a preferred embodiment, an antibody or antigen-binding portion thereof specifically binds to a polypeptide consisting of SEQ ID NOs:2, 4, 6, 8, 10, 11-29, 31, 33, 35, or 37 when it binds with a binding affinity $K_a$ of about $10^7$ l/mol or more. Specific binding can be tested using, for example, an enzyme-linked immunosorbant assay (ELISA), a radioimmunoassay (RIA), or a western blot assay using methodology well known in the art.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing Pg-specific antibodies can be identified using RIA or ELISA and isolated by cloning in semi-solid agar or by limiting dilution. Clones producing Pg-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind Pg antigens (e.g., Pg polypeptides), are particularly useful for detecting the presence of Pg or Pg antigens in a sample, such as a serum, blood, plaque or saliva sample from an Pg-infected animal such as a human. An immunoassay for Pg or an Pg antigen can utilize one antibody or several antibodies. An immunoassay for Pg or an Pg antigen can use, for example, a monoclonal antibody directed towards an Pg epitope, a combination of monoclonal antibodies directed towards epitopes of one Pg polypeptide, monoclonal antibodies directed towards epitopes of different Pg polypeptides, polyclonal antibodies directed towards the same Pg antigen, polyclonal antibodies directed towards different Pg antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of Pg or a Pg antigen. Supports include, for example, glass, polystyrene, polypropylene, polyethylene, dextran, nylon, amylases, natural and modified celluloses, polyacrylamides, agaroses and magletite.

Polyclonal or monoclonal antibodies of the invention can further be used to isolate Pg organisms or Pg antigens by immunoaffinity columns. The antibodies can be affixed to a solid support by, for example, adsorption or by covalent linkage so that the antibodies retain their immunoselective activity. Optionally, spacer groups can be included so that the antigen binding site of the antibody remains accessible. The immobilized antibodies can then be used to bind Pg organisms or Pg antigens from a sample, such as a biological sample including saliva, plaque, crevicular fluid, serum, sputum, blood, urine, feces, cerebrospinal fluid, amniotic fluid, wound exudate, or tissue. The bound Pg organisms or Pg antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by Pg. By measuring the increase or decrease of Pg antibodies to Pg antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

An antibody of the invention can be used in a method of the diagnosis of Pg infection by obtaining a test sample from an animal suspected of having an Pg infection. The test sample is contacted with an antibody of the invention under conditions enabling the formation of an antibody-antigen complex (i.e., an immunocomplex). The amount of antibody-antigen complexes can be determined by methodology known in the art. A level that is higher than that formed in a control sample indicates a Pg infection. Alternatively, a polypeptide of the invention can be contacted with a test sample. Pg antibodies in a positive body sample will form an antigen-antibody complex under suitable conditions. The amount of antibody-antigen complexes can be determined by methods known in the art.

Methods of Detection of Pg

The methods of the invention can be used to detect antibodies or antibody fragments specific for Pg in a test sample, such as a biological sample, an environmental sample, or a laboratory sample. A biological sample can include, for example, sera, blood, cells, blood, saliva, plaque, or tissue from an animal or human. The test sample can be untreated, precipitated, fractionated, separated, diluted, concentrated, or purified before combining with a polypeptide of the invention.

The methods comprise contacting a polypeptide of the invention with a test sample under conditions that allow a polypeptide/antibody complex, i.e., an immunocomplex, to form. That is, a polypeptide of the invention specifically binds to an antibody specific for Pg located in the sample. One of skill in the art is familiar with assays and conditions that are used to detect antibody/polypeptide complex binding. The formation of a complex between polypeptides and anti-Pg antibodies in the sample are detected.

An antibody of the invention can be used in a method of the diagnosis Pg infection by obtaining a test sample from a human or animal suspected of having a Pg infection. The test sample is contacted with an antibody of the invention under conditions enabling the formation of an antibody-antigen complex (i.e., an immunocomplex). The amount of antibody-antigen complexes can be determined by methodology known in the art. A level that is higher than that formed in a control sample indicates a Pg infection. Alternatively, a polypeptide of the invention can be contacted with a test sample. Pg antibodies in a positive body sample will form an antigen-antibody complex under suitable conditions. The amount of antibody-antigen complexes can be determined by methods known in the art.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, antibodies of the invention are attached to a solid phase or substrate. A test sample potentially comprising a protein comprising a polypeptide of the invention is added to the substrate. Antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise and indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), and fluorescence polarization immunoassay (FPIA).

Assays can use solid phases or substrates or can be performed by immunoprecipitation or any other methods that do not utilize solid phases. Where a solid phase or substrate is used, a polypeptide of the invention is directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing an anti-Pg antibody or fragment thereof is incubated with an indicator reagent comprising a signal generating compound conjugated to an antibody or antibody fragment specific for Pg for a time and under conditions sufficient to form antigen/antibody complexes of either antibodies of the test sample to the polypeptides of the solid phase or the indicator reagent compound conjugated to an antibody specific for Pg to the polypeptides of the solid phase. The reduction in binding of the indicator reagent conjugated to a Pg antibody to the solid phase can be quantitatively measured. A measurable reduction in the signal compared to the signal generated from a confirmed negative Pg test sample indicates the presence of anti-Pg antibody in the test sample. This type of assay can quantitate the amount of anti-Pg antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If Pg antibodies are present in the test sample they will bind the polypeptide conjugated to an indicator reagent and to the polypeptide immobilized on the support. The polypeptide/antibody/indicator complex can then be detected. This type of assay can quantitate the amount of anti-Pg antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If Pg antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-Pg antibodies in a test sample.

The formation of a polypeptide/antibody complex or a polypeptide/antibody/indicator complex can be detected by radiometric, colormetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-Pg antibodies in a test sample. Therefore, the methods of the invention can be used to diagnose Pg infection in a patient.

The methods of the invention can also indicate the amount or quantity of anti-Pg antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrate specimens such as urine, in order to determine the presence and/or amount of antibody present.

The invention further comprises assay kits (e.g., articles of manufacture) for detecting anti-Pg antibodies or antibody fragments, Pg, or Pg polypeptides in a sample. A kit comprises one or more polypeptides of the invention and means for determining binding of the polypeptide to anti-Pg antibodies or antibody fragments in the sample. A kit or article of manufacture can also comprise one or more antibodies or antibody fragments of the invention and means for determining binding of the antibodies or antibody fragments to Pg or Pg polypeptides in the sample. A kit can comprise a device containing one or more polypeptides or antibodies of the invention and instructions for use of the one or more polypeptides or antibodies for, e.g., the identification of a Pg infection in a mammal. The kit can also comprise packaging material comprising a label that indicates that the one or more polypeptides or antibodies of the kit can be used for the identification of Pg infection. Other components such as buffers, controls, and the like, known to those of ordinary skill in art, can be included in such test kits. The polypeptides, antibodies, assays, and kits of the invention are useful, for example, in the diagnosis of individual cases of Pg infection in a patient, as well as epidemiological studies of Pg.

Polypeptides and assays of the invention can be combined with other polypeptides or assays to detect the presence of Pg along with other organisms. For example, polypeptides and assays of the invention can be combined with reagents that detect *Actinobacillus actinomycetemcomitans*.

Methods of Treatment, Amelioration, or Prevention of a Disease Caused by Pg

Polypeptides, polynucleotides, and antibodies of the invention can be used to treat, ameliorate, or prevent a disease caused by Pg, such rapidly progressive or refractory adult periodontitis, endocarditis, thyroid gland abscesses, urinary tract infections, brain abscesses, and vertebral osteomyelitis, and cardiovascular disease.

For example, an antibody, such as a monoclonal antibody of the invention or fragments thereof, can be administered to an animal, such as a human. In one embodiment of the invention an antibody or fragment thereof is administered to an animal in a pharmaceutical composition comprising a pharmaceutically acceptable carrier. A pharmaceutical composition comprises a therapeutically effective amount of an antibody or fragments thereof. A therapeutically effective amount is an amount effective in alleviating the symptoms of Pg infection or in reducing the amount of Pg organisms in a subject.

Polypeptides or polynucleotides of the invention can be present in an immunogenic composition and used to elicit an immune response in a host. An immunogenic composition is capable of inducing an immune response in an animal. An immunogenic polypeptide or polynucleotide composition of the invention is particularly useful in sensitizing an immune system of an animal such that, as one result, an immune response is produced that ameliorates or prevents the effect of Pg infection. The elicitation of an immune response in animal model can be useful to determine, for example, optimal doses or administration routes. Elicitation of an immune response can also be used to treat, prevent, or ameliorate a disease or infection caused by Pg. An immune response includes humoral immune responses or cell mediated immune responses, or a combination thereof. An immune response can also comprise the promotion of a generalized host response, e.g., by promoting the production of defensins.

The generation of an antibody titer by an animal against Pg can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to Pg can be identified by eliciting antibodies directed against Pg polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $AlK(SO_4)_2$; $AlNa(SO_4)_2$, $AlNH_4(SO_4)$, Silica, Alum, $Al(OH)_3$, and $Ca_3(PO_4)_2$), poly-nucleotides (i.e. Polyic and Poly AU acids), and certain natural substances (e.g. wax D from *Mycobacterium tuberculosis*, as well as substances found in *Corynebacterium parvum*, *Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a large mammal, such as a baboon, chimpanzee, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a large mammal, such as a human, at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with Pg or can be administered to an Pg-infected animal. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

Additionally, a *Porphyromonas gingivalis* organism can be genetically engineered to remove one or more of the polynucleotide sequences encoding a polypeptide consisting essentially of SEQ ID NOs:2, 4, 6, 8, 10, 11-29, 31, 33, 35, or 37. The organism can be useful in, for example, replacement therapy.

The materials for use in a method of the invention can be present in a kit. A kit can comprise one or more elements used in the method. For example, a kit can contain an antibody of the invention in a container and Pg polypeptides in another container. The kit and containers are labeled with their contents and the kit includes instructions for use of the elements in the containers. The constituents of the kit can be present in, for example, liquid or lypholized form.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Figure 10:
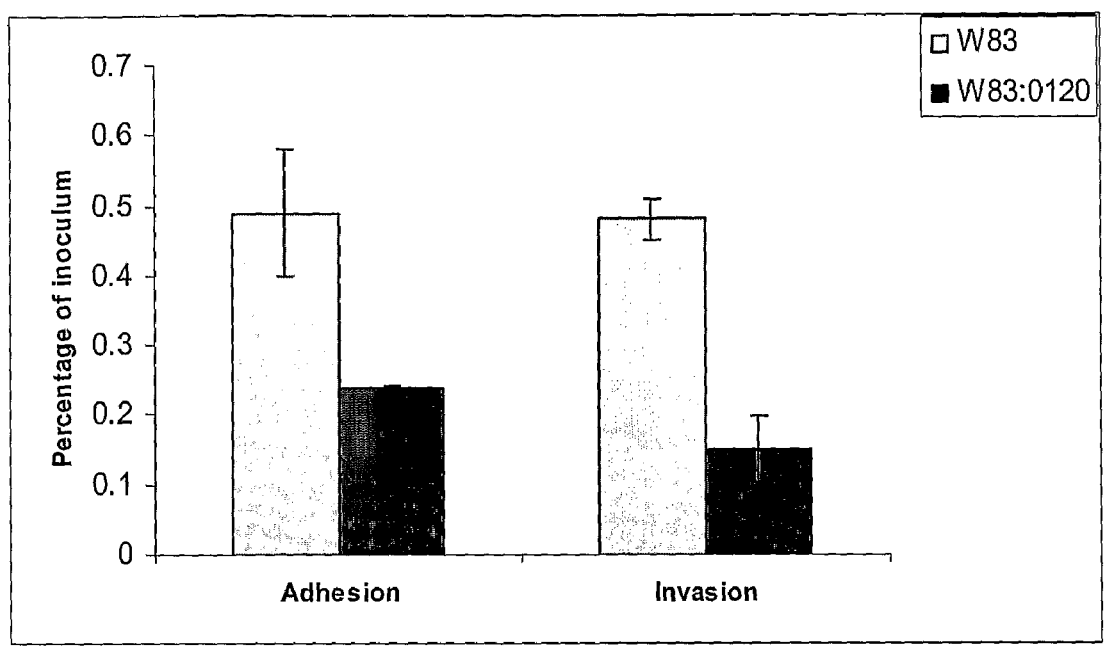
FIG. 10 shows invasion ability of the *P. gingivalis* mutant W83:0120 expressed as the percentage of inoculum. Mutant W83:0120 invades 3.2 fold less (p<0.03) than wild type, and adheres 2.3 fold less (p<0.03) than wild type. The lower invasion is probably due to the lower adhesion.

The roles of nine Pg genes that are differentially regulated in the invasive mechanism of *P. gingivalis* were identified. Four of these genes encode hypothetical proteins (PG0242, PG0686, PG0717 and PG1683) and five genes encode: a protein ferritin (PG1286); a putative UDP-N-acetylglucosamine 2-epimerase (PG0120); a putative lipoprotein RagB (PG0186); a putative ABC transporter, permease protein (PG0280); and a putative formate—tetrahydrofolate ligase (PG1321). See FIGS. 7 and 10. To construct isogenic mutants in these genes, an internal fragment of each gene was amplified and cloned into a *P. gingivalis* suicide vector, pVA3000, containing an ErmF/AM cassette. *E. coli* strain S17-1 cells were transformed by electroporation and the plasmids were then transformed into *P. gingivalis* W83 cells by conjugation. The conjugation mixture was spread onto blood-agar plates containing 30 µg/ml of gentamycin and 5 µg/ml of clindamycin to select for mutants. Mutational insertions were confirmed by southern blot. Homologous recombination of the vector into the chromosome resulted in a truncated gene (FIG. 1).

The plasmids were then transformed into *P. gingivalis* W83 cells by conjugation and mutants were isolated on blood agar plates containing clindamycin. Mutational insertions were confirmed by southern blot analysis. Mutants (W83:0242, W83:0686, W83:0717, W83:1286 and W83:1683, W83:0120, W83:0186, W83:0280; W83:1321) and strain W83 (control) were challenged to invade HCAE cells for at least 2.5 h.

The results indicated that all mutants had a decreased invasive activity, compared to wild-type strain W83. Four mutants showed an altered ability to adhere to HCAE cells: W83:0242 adhered 7.7 fold less p<0.002); W83:1683 adhered 3.2 fold less (p<0.001); W83:0120 adhered 2.3 fold less (p<0.03); W38:0186 adhered 1.8 fold less (p<0.03). W83:0280 and W83:1321 were not tested for adherence. The mutant W83:0242 showed the lowest invasive ability at 2.5 hours (8.1 fold, p<0.001). These data suggest that selected genes have a role in *P. gingivalis* invasion. The low invasion efficiencies of mutants W83:0242, W83:1683, W83:0120, and W38:0186 are likely due to their altered ability to adhere to the human cells; therefore genes PG0242, PG1683, PG0120, and PG0186 may be important for the adherence of *P. gingivalis* to HCAE cells. Mutants W83:686, W83:717 and W83:1286 showed no difference in their ability to adhere when compared with strain W83, suggesting these genes may be important for *P. gingivalis* survival inside of HCAE cells.

Example 2

Invasion of HCAEC. Invasion of *P. gingivalis* strain W83 and mutants in HCAE cells were assayed. Late log phase cultures of strain W83 and mutant strains were used to inoculate in EBM-2 complete antibiotic-free medium at a final concentration of 107 bacteria per ml. Bacterial suspensions were added to confluent HCAEC monolayers (105 cells) in 24 well-plates and incubated at 37° C. for 1.5 h. After this time, unattached bacteria were removed by washing the monolayers 3 times with PBS. Then, EBM-2 medium with 300 µg/ml of gentamycin and 200 µg/ml of metronidazole was added to each well to kill extracellular bacteria for 1.0 h at 37° C. To determine the number of internalized bacteria, HCAE cells were ruptured with 1 ml of sterile distilled water at 37° C. for 20 minutes. Cell lysates were serially diluted, plated on blood-agar plates and incubated anaerobically at 37° C. for 10 days to count the colonies.

Figure 11:
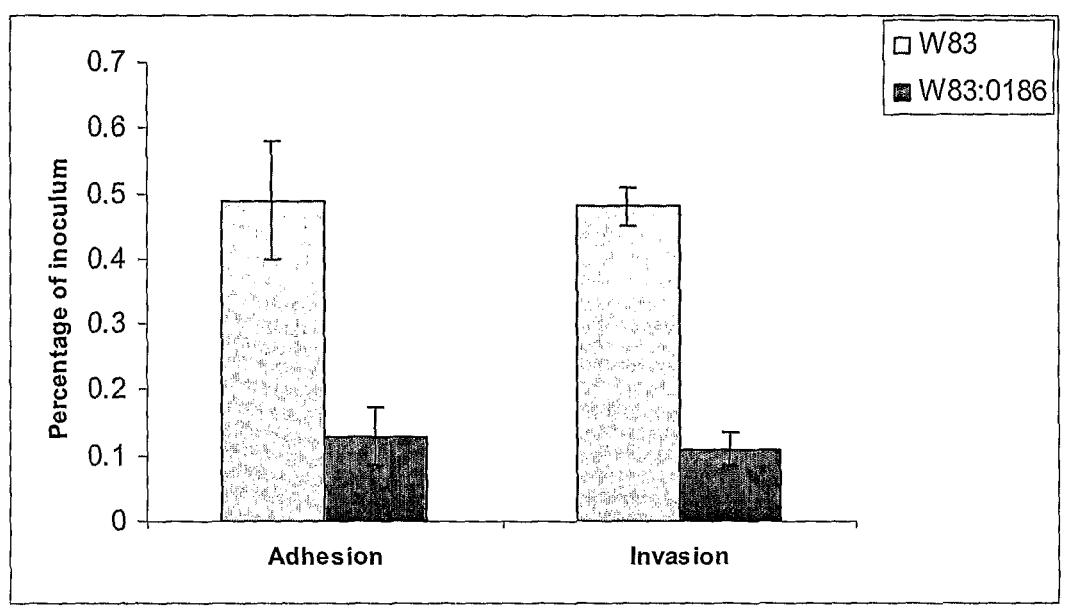
FIG. 11 shows invasion ability of the *P. gingivalis* mutant W83:0186 expressed as the percentage of inoculum. Mutant W83:0186 invades 2.6 fold less (p<0.03) than wild type, and adheres 1.8 fold less (p<0.03) than wild type. The lower invasion is probably due to the lower adhesion.
Figure 12:
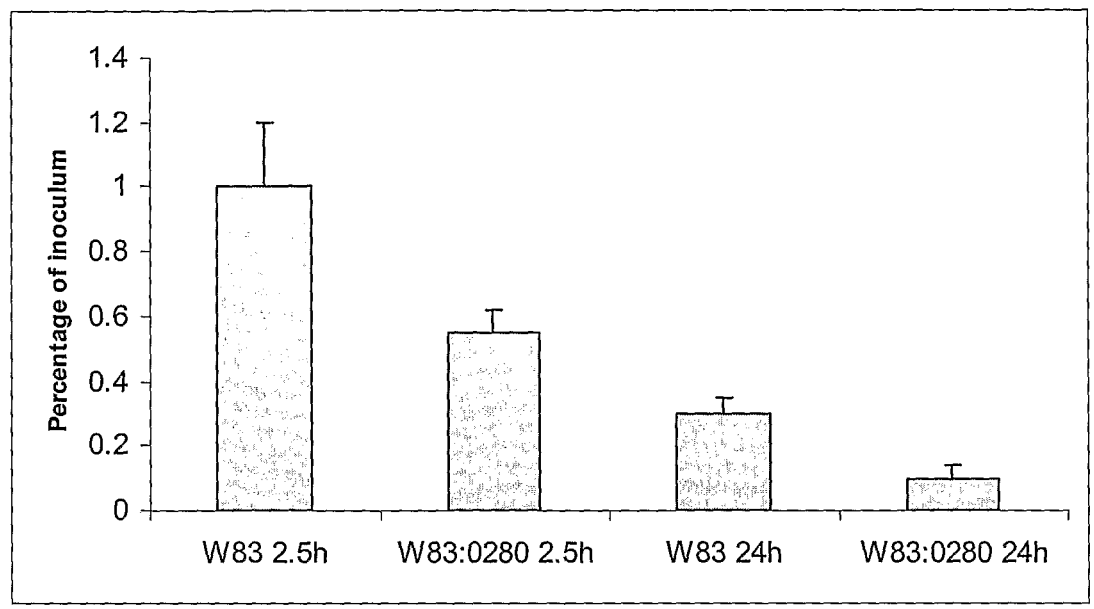
FIG. 12 shows invasion ability of the *P. gingivalis* mutant W83:0280 expressed as the percentage of inoculum. Adherence was not tested. Mutant W83:0280 invades 1.8 fold less (p<0.03) than wild type at 2.5 hours and invades 3.0 fold less (p<0.03) than wild type at 24 hours. Therefore, there is lower invasion than wild type at 2.5 hours and this difference increases with time.
Figure 13:
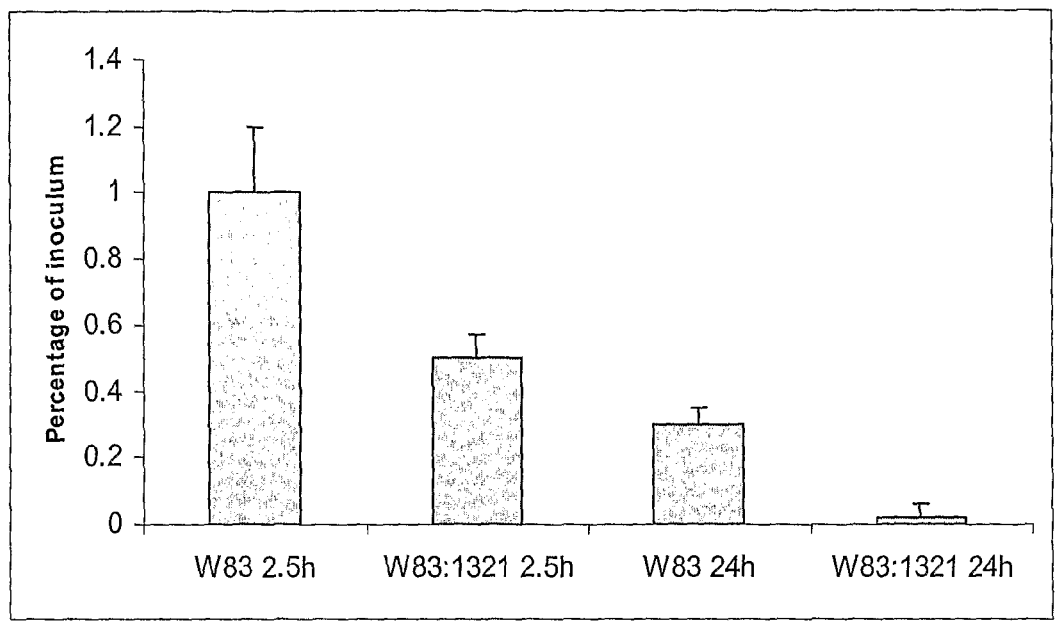
FIG. 13 shows invasion ability of the *P. gingivalis* mutant W83:1321 expressed as the percentage of inoculum. Adherence was not tested. Mutant W83:1321 invades 2.0 fold less (p<0.03) than wild type at 2.5 hours and invades 15.4 fold less (p<0.03) than wild type at 24 hours. Therefore, there is lower invasion than wild type at 2.5 hours and this difference increases with time.

The results indicated that all mutants had a decreased invasive activity, compared to wild-type strain W83 (FIGS. 2-6 and 10-13). Two mutants showed an altered ability to adhere to HCAE cells: W83:0242 adhered 11.7 fold less (p<0.01) (FIG. 2), W83:1683 adhered 2.1 fold less (p<0.02) (FIG. 6) W83:0120 adhered 2.3 fold less (p<0.03) (FIG. 10), W83:0186 adhered 1.8 fold less (p<0.03) (FIG. 11). The mutant W83:0242 showed the lowest invasive ability at 2.5 hours (6.1 fold, p<0.03).

The low invasion efficiencies of mutants W83:0242, W83:1683, W83:0120, and W83:0186 are likely due to their altered ability to adhere to the human cells; therefore genes PG0242, PG1683, PG0120, and PG0186 may be important for the adherence of *P. gingivalis* to HCAE cells. Mutants W83:0686, W83:0717 and W83:1286 showed no difference in their ability to adhere when compared with strain W83, however they invaded less then wild type, suggesting these genes might be important for *P. gingivalis* invasiveness and/or survival inside of HCAE cells.

Therefore polypeptides shown in SEQ ID NOs: 2, 4, 6, 8, 10, 11-29, 31, 33, 35, and/or 37 can be useful in, inter alia, detecting invasive Pg infection in an animal.

Example 3

RNA Extraction, cDNA Probe Generation, and Microarray Experiments

*P. gingivalis* W83 and the luxS mutant, LY2001, were cultured in TSB, then samples were collected at mid-exponential growth phase. The samples were immediately mixed with 2 volumes of RNA Protect bacterial reagent (Qiagen, Valencia, Calif.) and vortexed for 5 s. The mixtures were centrifuged at room temperature for 10 min at 5,000×g and the supernatant was discarded. The RNA extraction was done using the RNeasy® Mini Kit (Qiagen) following the manufacturer's protocol. During the RNA extraction, DNase was used to remove any DNA contamination (Rnase-free Dnase Set, Qiagen).

cDNA was generated using random primers for reverse transcription (Invitrogen Life Technologies, Carlsbad, Calif.). The primers were annealed at 70° C. for 10 min, followed by snap-freezing in a dry ice/ethanol bath for 30 sec and then centrifugation for 1 min. The reaction mixture (Superscript II buffer, 0.1 M DTT, and aa-dNTP mix) was then incubated with Superscript II reverse transcriptase (Invitrogen) at 42° C. overnight. Residual RNA was removed by alkaline treatment followed by neutralization, and cDNA was purified with a QIAQUICK® PCR purification kit (Qiagen). Purified cDNAs from the W83 and LY2001 strains were each labeled with indocarbocyanine (Cy3)-dUTP and indodicarbocyanine (Cy5)-dUTP (Amersham Biosciences, Piscataway, N.J.) and were processed using a dye-swapping design. A total of 6 slides were used. Wild type cDNA was labeled with cy3 for 3 slides and with cy5 for the remaining 3 slides. This strategy was used to avoid any differences caused by the labeling activity of cy3 versus that of cy5. The labeling mixtures were cleaned again using a QIAQUICK® PCR purification kit (Qiagen). Equal amounts of labeled cDNA from the W83 and LY2001 strains were used to hybridize the microarray slides. Hybridization was carried out at 42° C. for 18 hours in the dark. After hybridization, the slides were washed and scanned using a GENEPIX® scanner (Axon instruments Inc, Union City, Calif.) at 532 nm (Cy3 channel) and 635 nm (Cy5 channel), and the images were stored on discs.

Microarray Data Analysis.

Data from six individual experiments were normalized and then analyzed using the Spotfinder Software (The Institute of Genomic Research). The data points with a density below 100,000 were discarded for analysis according to the manufacturer's suggestion. A cutoff ratio of 1.5:1 was used on all the slides. SAM software (Significant Analysis of Microarray, version 1.15, Stanford University, CA) was used to test statistically significant results from the microarray experiments. This statistical analysis involved factoring the change in expression of each gene relative to the standard deviation of all replicates for that gene. Therefore, genes with a small change were not discounted if the ratios were consistent among repeats, thus effectively reducing false-negatives. False-positives were also avoided when genes had poor reproducibility between replicates. Thus this method of statistical analysis maximized both the quantity of genes found and the reliability of the results. Spot intensities for all channels were input into SAM as paired, unlogged values. Delta values were chosen according to the lowest false discovery rate, which for this study was 4.7%. In this experiment, the genes with expression ratios of $\geq 1.5$ were considered biologically significant.

Real Time PCR Verification and Data Analysis.

Nine genes were selected for verification by RT-PCR. For each of the genes tested, primers (Table 1) were designed using Beacon Design software (Premier Biosoft International, Palo Alto, Calif.) to amplify products from 75 to 150 bp. A standard curve was created using serial dilutions of the gel purified DNA fragment of each gene and a *P. gingivalis* 16S rRNA gene fragment was used as an internal control. Reverse transcription using Superscript II reverse transcriptase (Invitrogen) was performed. The cDNA was used as a template for RT-PCR. In every run of RT-PCR, two standard curves were created, one for 16S rRNA and one for the target gene. The unknown cDNA samples from wild type W83 and mutant LY2001 were compared to the standard curve to calculate the starting quantity in each sample. The ratio from real time PCR for each target gene was calculated for both samples.

TABLE 1

| Gene name | Locus in genome | Average | SD | Function |
| --- | --- | --- | --- | --- |
| Genes upregulated in luxS mutant genes related with stress response | | | | |
| chaperonin, 60 kDa, GroEL | PG0520 | 2.26 | 0.23 | Chaperonin; 60 kDa; GroEL |
| HtrA protein | PG0593 | 2.01 | 0.36 | HtrA Protein |
| alkyl hydroperoxide reductase, F subunit | PG0619 | 1.85 | 0.35 | alkyl hydroperoxide reductase, F subunit |
| clpB protein | PG1118 | 6.06 | 1.65 | clpB protein |
| dnaK protein | PG1208 | 4.54 | 0.72 | dnaK protein |
| genes related with regulation | | | | |
| RNA polymerase sigma-70 factor, ECF subfamily | PG0985 | 2 | 0.41 | RNA polymerase sigma-70 factor, ECF subfamily |
| putative antigen | | | | |
| immunoreactive 46 kDa antigen PG99 | PG1798 | 1.65 | 0.17 | immunoreactive 46 kDa antigen PG99 |
| outer membrane efflux protein | PG0538 | 1.72 | 0.13 | outer membrane efflux protein, previously submitted to Genbank by Ross et al. as immunoreactive 52 kDa antigen PG41 |
| hypothetical proteins | | | | |
| hypothetical protein | PG0611 | 1.55 | 0.1 | hypothetical protein |
| hypothetical protein | PG0614 | 1.58 | 0.18 | hypothetical protein |
| hypothetical protein | PG1795 | 1.69 | 0.21 | hypothetical protein |
| hypothetical protein | PG1102 | 2.02 | 0.24 | hypothetical protein |
| conserved hypothetical protein | PG2225 | 1.71 | 0.26 | conserved hypothetical protein |
| Genes with other functions | | | | |
| ABC transporter, permease protein, putative | PG1664 | 1.85 | 0.29 | ABC transporter, permease protein, putative, Transport |

TABLE 1-continued

| Gene name | Locus in genome | Average | SD | Function |
|---|---|---|---|---|
| | | | | and binding proteins: Unknown substrate |
| putative epithelial cell attachment protein | PG2224 | 2.4 | 0.5 | putative epithelial cell attachment protein |
| O-sialoglycoprotein endopeptidase | PG1724 | 1.63 | 0.24 | O-sialoglycoprotein endopeptidase |
| cytochrome d ubiquinol oxidase, subunit I | PG0900 | 1.83 | 0.31 | cytochrome d ubiquinol oxidase, subunit I |
| Genes downregulated in luxS mutant | | | | |
| D-isomer specific 2-hydroxyacid dehydrogenase family protein | PG1279 | 0.59 | 0.08 | D-isomer specific 2-hydroxyacid dehydrogenase family protein |
| conserved hypothetical protein | PG1280 | 0.58 | 0.07 | conserved hypothetical protein |

We claim:

1. A method for detecting the presence of an invasive *Porphyromonas gingivalis* infection in an animal comprising contacting a test sample from the animal with a purified polypeptide comprising the polypeptide sequence set forth as SEQ ID NO:17; and detecting immunocomplexes comprising the purified polypeptide comprising the polypeptide sequence set forth as SEQ ID NO:17 and an antibody or fragment thereof in the test sample, wherein detection of the immunocomplexes indicates the presence of invasive *Porphyromonas gingivalis* infection.

2. The method of claim 1, wherein the method further comprises detecting the amount of immunocomplexes.

3. The method of claim 1, wherein the test sample is serum, blood, saliva, or plaque.

4. The method of claim 1, wherein the polypeptide is immobilized to a solid support.

5. The method of claim 1, wherein the polypeptide is labeled.

6. The method of claim 2, wherein the detection is by radioimmunoassay, enzyme-linked immunosorbent assay, immunohistochemical assay or immunoenzyme-assay.

7. A method for detecting an invasive *Porphyromonas gingivalis* polypeptide in a test sample comprising contacting the test sample with an antibody or fragment thereof that specifically binds a polypeptide consisting of the polypeptide sequence set forth as SEQ ID NO:17, and detecting immunocomplexes comprising the invasive *P. gingivalis* polypeptide and the antibody or fragment thereof, wherein detection of the immunocomplexes indicates the presence of the invasive *Porphyromonas gingivalis* polypeptide.

8. The method of claim 7, wherein the method further comprises detecting the amount of immunocomplexes.

9. The method of claim 7, wherein the test sample is a serum, blood, saliva, or plaque.

10. The method of claim 7, wherein the antibody or fragment thereof is immobilized to a solid support.

11. The method of claim 7, wherein the antibody or fragment thereof is labeled.

12. The method of claim 7, wherein the detection is by radioimmunoassay, enzyme-linked immunosorbent assay, immunohistochemical, or immunoenzyme-assay.

\* \* \* \* \*

SEQUENCE LISTING

<160> NUMBER OF SEQ ID NOS: 37

<210> SEQ ID NO 1
<211> LENGTH: 699
<212> TYPE: DNA
<213> ORGANISM: Porphyromonas gingivalis

<400> SEQUENCE: 1

```
atggaaggac gtttgacagt cgtgccgact cctatcggca atttggagga tattaccttg      60
agagccttga aggtactgcg cgaagcagac ctgattttgg cagaggacac gcgtaccagc     120
agtgtattgc tccaccatta cgacattcac tgtccgctcc agagccatca taaattcaac     180
gaacatcgta cggccaagtc attggccgaa cggatatccg gaggtgaacg catagctttg     240
atctccgacg ccggaactcc cgggatcagc gaccccggtt ttttgcttgt cagagcatgt     300
gccgagttgg gtgtagtggt agaatgtctg cccggaccca cagcattgat tccggctttg     360
gtagcaagcg gactccctgc cgacaggttt gttttcgaag gttttctgcc tgtcaagaaa     420
ggccgccaaa ctcgaatgaa agaattggcc gaagagctcc ggacgatgat attttatgag     480
tcgccccatc gggtgctcag gactctgacc caatttgtgg agactttcgg tctcgatcga     540
ccagctgctg catgccggga gctgagcaaa ctccacgaag aggtgatccg cggaacactc     600
gcggaattac tggctcactt cgaaaaccac cctccaaggg gagaattcgt tctcatcgtg     660
ggtggagccg ccccgaaagg gagaaaagaa gagaagcaa                            699
```

<210> SEQ ID NO 2
<211> LENGTH: 233
<212> TYPE: PRT
<213> ORGANISM: Porphyromonas gingivalis

<400> SEQUENCE: 2

```
Met Glu Gly Arg Leu Thr Val Val Pro Thr Pro Ile Gly Asn Leu Glu
1               5                   10                  15

Asp Ile Thr Leu Arg Ala Leu Lys Val Leu Arg Glu Ala Asp Leu Ile
                20                  25                  30

Leu Ala Glu Asp Thr Arg Thr Ser Ser Val Leu Leu His His Tyr Asp
            35                  40                  45

Ile His Cys Pro Leu Gln Ser His His Lys Phe Asn Glu His Arg Thr
        50                  55                  60

Ala Lys Ser Leu Ala Glu Arg Ile Ser Gly Gly Glu Arg Ile Ala Leu
65                  70                  75                  80
```

```
Ile Ser Asp Ala Gly Thr Pro Gly Ile Ser Asp Pro Gly Phe Leu Leu
                85                  90                  95

Val Arg Ala Cys Ala Glu Leu Gly Val Val Glu Cys Leu Pro Gly
            100                 105                 110

Pro Thr Ala Leu Ile Pro Ala Leu Val Ala Ser Gly Leu Pro Ala Asp
            115                 120                 125

Arg Phe Val Phe Glu Gly Phe Leu Pro Val Lys Lys Gly Arg Gln Thr
            130                 135                 140

Arg Met Lys Glu Leu Ala Glu Leu Arg Thr Met Ile Phe Tyr Glu
145                 150                 155                 160

Ser Pro His Arg Val Leu Arg Thr Leu Thr Gln Phe Val Glu Thr Phe
                165                 170                 175

Gly Leu Asp Arg Pro Ala Ala Ala Cys Arg Glu Leu Ser Lys Leu His
            180                 185                 190

Glu Glu Val Ile Arg Gly Thr Leu Ala Glu Leu Leu Ala His Phe Glu
            195                 200                 205

Asn His Pro Pro Arg Gly Glu Phe Val Leu Ile Val Gly Gly Ala Ala
            210                 215                 220

Pro Lys Gly Arg Lys Glu Lys Gln
225                 230

<210> SEQ ID NO 3
<211> LENGTH: 1551
<212> TYPE: DNA
<213> ORGANISM: Porphyromonas gingivalis

<400> SEQUENCE: 3
atgcaggtca taaaaacaaa tgaaactttt gacagcctcg acaaaagtaa gttggagcgt      60
atgctcgaca tcaaagaggc tcatcgcgaa ggtcatctga cacttgaaga ggccaaggag     120
cgtatgaaaa agaagtgggt tccatctcg cccgaagagt ttgccgcagc agagcaactc      180
ttcaaagaac gtgatcagga cgaatgccaa aacgaagacg tacggacaat gctacagctg     240
ttcgaaggcc tgataaatcc cattcgtccc gatttacctt tcggacaccc catcgatgcc     300
tatctgcgcg aaaacgataa ggccaaagaa ctactcgatc aggcggatgc cctactggag     360 cgcacttta tccccaatcc atggatagaa ctgatggaga cgcttatggg atataagcta      420
cactttgctc gcaaacaaaa ccaactctat tcgacactgg agcagaaagg attcgaccgc     480
ccctccacta cgatgtggac ttatgacgat catatccgcg acgagatgaa caaagccatg     540
agcctactgc gcgaaaaaga ctacgactcc ttccctgcag catacaaaga gatggctatc     600
gttctgcgtg acctgatgga aaagaagag cttatccttt atccaacctc tctgaagctc      660
atttccgaca aagagttcga agaaatgaaa catggcgatc gggaaatagg cttcttcctt     720
atcgacatgc cggaattaga tgcaccggcc aagcaatcaa agaagcccca cggccaatca     780
tttatggcag aactgggagc cttacttgcc aaacatggta tggggacagg cggacaagac     840
gacaaggcga tactggatgt agccgaagga aagctgactt ggagcagat caatctgctt      900 ttccgtcatc tccctgtgga tatttcgttc gtggacgaaa acgagctggt ttgtttctat     960
acggacacaa agcacagagt attccccaga agcaagggg tgatcggccg agaagtacgc     1020
aactgccatc cgcccaagag cgttcatata gtagaggaga taatcgataa gttccgacgt    1080
ggcgaacagg atcgcgcaga attctggatc aataagcccg gagtcttcat ctacattgtc    1140
tatgtggcca tcagagacgc cgacgggcgt tccgcggtg tgatggaaat gatgcaagac     1200
tgcacacgga tccgtagtct tgaaggctcg cgtacacttc ttacttggga cgaagagcaa    1260
```

```
agtccggcac aaggatcgaa agaaagcgaa tccgatactg ccggagaaga cggcattcgg   1320
ccggacacga agctgaagag tctcttgcag cggtatccgc aactgatgga tgatttgcca   1380
acgatcagtt ccaagttcac cctccttcgt tctccgatgg ccaaagtaat tcttcctgtt   1440
gccaccatta aaatgatgag cgaacgcgcc gacattccgt cggatatgct catcggcaaa   1500
ctggaatcgc tcatcgcttc gtacaataaa ccggatcgat cggaagagaa a           1551
```

<210> SEQ ID NO 4
<211> LENGTH: 517
<212> TYPE: PRT
<213> ORGANISM: Porphyromonas gingivalis

<400> SEQUENCE: 4

```
Met Gln Val Ile Lys Thr Asn Glu Thr Phe Asp Ser Leu Asp Lys Ser
1               5                   10                  15

Lys Leu Glu Arg Met Leu Asp Ile Lys Glu Ala His Arg Glu Gly His
            20                  25                  30

Leu Thr Leu Glu Glu Ala Lys Glu Arg Met Lys Lys Glu Val Gly Ser
        35                  40                  45

Ile Ser Pro Glu Glu Phe Ala Ala Glu Gln Leu Phe Lys Glu Arg
    50                  55                  60

Asp Gln Asp Glu Cys Gln Asn Glu Asp Val Arg Thr Met Leu Gln Leu
65                  70                  75                  80

Phe Glu Gly Leu Ile Asn Pro Ile Arg Pro Asp Leu Pro Phe Gly His
                85                  90                  95

Pro Ile Asp Ala Tyr Leu Arg Glu Asn Asp Lys Ala Lys Glu Leu Leu
            100                 105                 110

Asp Gln Ala Asp Ala Leu Leu Glu Arg Thr Phe Ile Pro Asn Pro Trp
        115                 120                 125

Ile Glu Leu Met Glu Thr Leu Met Gly Tyr Lys Leu His Phe Ala Arg
    130                 135                 140

Lys Gln Asn Gln Leu Tyr Ser Thr Leu Glu Gln Lys Gly Phe Asp Arg
145                 150                 155                 160

Pro Ser Thr Thr Met Trp Thr Tyr Asp Asp His Ile Arg Asp Glu Met
                165                 170                 175

Asn Lys Ala Met Ser Leu Leu Arg Glu Lys Asp Tyr Asp Ser Phe Pro
            180                 185                 190

Ala Ala Tyr Lys Glu Met Ala Ile Val Leu Arg Asp Leu Met Glu Lys
        195                 200                 205

Glu Glu Leu Ile Leu Tyr Pro Thr Ser Leu Lys Leu Ile Ser Asp Lys
    210                 215                 220

Glu Phe Glu Glu Met Lys His Gly Asp Arg Glu Ile Gly Phe Phe Leu
225                 230                 235                 240

Ile Asp Met Pro Glu Leu Asp Ala Pro Ala Lys Gln Ser Lys Glu Ala
                245                 250                 255

His Gly Gln Ser Phe Met Ala Glu Leu Gly Ala Leu Leu Ala Lys His
            260                 265                 270

Gly Met Gly Thr Gly Gly Gln Asp Asp Lys Ala Ile Leu Asp Val Ala
        275                 280                 285

Glu Gly Lys Leu Thr Leu Glu Gln Ile Asn Leu Phe Arg His Leu
    290                 295                 300

Pro Val Asp Ile Ser Phe Val Asp Glu Asn Glu Leu Val Cys Phe Tyr
305                 310                 315                 320
```

```
Thr Asp Thr Lys His Arg Val Phe Pro Arg Ser Lys Gly Val Ile Gly
            325                 330                 335
Arg Glu Val Arg Asn Cys His Pro Pro Lys Ser Val His Ile Val Glu
        340                 345                 350
Glu Ile Ile Asp Lys Phe Arg Arg Gly Glu Gln Asp Arg Ala Glu Phe
    355                 360                 365
Trp Ile Asn Lys Pro Gly Val Phe Ile Tyr Val Tyr Val Ala Ile
370                 375                 380
Arg Asp Ala Asp Gly Arg Phe Arg Gly Val Met Glu Met Met Gln Asp
385                 390                 395                 400
Cys Thr Arg Ile Arg Ser Leu Glu Gly Ser Arg Thr Leu Leu Thr Trp
                405                 410                 415
Asp Glu Glu Gln Ser Pro Ala Gly Ser Lys Glu Ser Glu Ser Asp
            420                 425                 430
Thr Ala Gly Glu Asp Gly Ile Arg Pro Asp Thr Lys Leu Lys Ser Leu
        435                 440                 445
Leu Gln Arg Tyr Pro Gln Leu Met Asp Asp Leu Pro Thr Ile Ser Ser
    450                 455                 460
Lys Phe Thr Leu Leu Arg Ser Pro Met Ala Lys Val Ile Leu Pro Val
465                 470                 475                 480
Ala Thr Ile Lys Met Met Ser Glu Arg Ala Asp Ile Pro Ser Asp Met
                485                 490                 495
Leu Ile Gly Lys Leu Glu Ser Leu Ile Ala Ser Tyr Asn Lys Pro Asp
            500                 505                 510
Arg Ser Glu Glu Lys
        515

<210> SEQ ID NO 5
<211> LENGTH: 1101
<212> TYPE: DNA
<213> ORGANISM: Porphyromonas gingivalis

<400> SEQUENCE: 5
atgaaagtat tcaagttttt agcatcgatg gtgctgtttg caggcttatt tgctgcatgc    60
aacaaggaag acaacgatct catcaattcg acttcggatg aagcggcaac tttggctacg   120
atgtatccca tgctcagaa tgtaagatgg gagcaagaag gtgaattccg tgtggcagaa   180
ttcatgaacg aaggcgttaa gtctgaagca tggttcttgc gaagcatctg caatacacg   240
gagatagaca ttccctacag cgccctgcct aaagcagtcc gagctgcttt tgaggcaagt   300
gaatatgcca agtggaaaat agaagacata gataaggtag aacgtaacgg taccgaaata   360
ttctatgtca tagaagtaga aaagggagac caggaagtcg acttgttcta catgcccaat   420
ggcaagctga tcaaaaccgt gaaaaaacct cacaacggat cagcaggtca atatgccaat   480
ccggtgattc cggcaggagt aatgaatacc atcaaggctt acatcgcttc caactatcct   540
aatgcaacca ttctggagta cgagatcgaa gatggctaca tagaggtgga cattttggat   600
ggtacggtac atcgagttct tatttttcaca ctccaaggcg agtgggtaaa tagtcatgtg   660
gatgatggag atgacgatta tgactacgat gatgatgcat acgaaaacaa cattccggcc   720
aacatcaagg ctctgatcat cagctatgtc aatcagaatt acccgggagc tgtcattcac   780
agtatcgagc gtaactccaa tggtacttat gacgtagaaa tttactacaa caataggag   840
tacgacttgc tgttcgatgc acagggcaac ctcatcagcg aaacgtaga cgatcaggat   900
gatgacgaca acattcctgc tcacatcaag gctaagatca tcaattacgt caaccggaac   960
```

```
tacccccggtg catttatcaa ggacatcgaa agaaagtcca acggcacata caaggcggaa    1020
atcgtgtaca caacaagga gtatgatttg ctgttcgatg cacagggcaa tttcatcagt    1080
gcgagcctgg atgacaaaaa a                                              1101
```

<210> SEQ ID NO 6
<211> LENGTH: 367
<212> TYPE: PRT
<213> ORGANISM: Porphyromonas gingivalis

<400> SEQUENCE: 6

```
Met Lys Val Phe Lys Phe Leu Ala Ser Met Val Leu Phe Ala Gly Leu
1               5                   10                  15

Phe Ala Ala Cys Asn Lys Glu Asp Asn Asp Leu Ile Asn Ser Thr Ser
                20                  25                  30

Asp Glu Ala Ala Thr Leu Ala Thr Met Tyr Pro Asn Ala Gln Asn Val
            35                  40                  45

Arg Trp Glu Gln Glu Gly Glu Phe Arg Val Ala Glu Phe Met Asn Glu
        50                  55                  60

Gly Val Lys Ser Glu Ala Trp Phe Leu Arg Ser Ile Trp Gln Tyr Thr
65                  70                  75                  80

Glu Ile Asp Ile Pro Tyr Ser Ala Leu Pro Lys Ala Val Arg Ala Ala
                85                  90                  95

Phe Glu Ala Ser Glu Tyr Ala Lys Trp Lys Ile Glu Asp Ile Asp Lys
            100                 105                 110

Val Glu Arg Asn Gly Thr Glu Ile Phe Tyr Val Ile Glu Val Glu Lys
        115                 120                 125

Gly Asp Gln Glu Val Asp Leu Phe Tyr Met Pro Asn Gly Lys Leu Ile
130                 135                 140

Lys Thr Val Lys Lys Pro His Asn Gly Ser Ala Gly Gln Tyr Ala Asn
145                 150                 155                 160

Pro Val Ile Pro Ala Gly Val Met Asn Thr Ile Lys Ala Tyr Ile Ala
                165                 170                 175

Ser Asn Tyr Pro Asn Ala Thr Ile Leu Glu Tyr Glu Ile Glu Asp Gly
            180                 185                 190

Tyr Ile Glu Val Asp Ile Leu Asp Gly Thr Val His Arg Val Leu Ile
        195                 200                 205

Phe Thr Leu Gln Gly Glu Trp Val Asn Ser His Val Asp Asp Gly Asp
210                 215                 220

Asp Asp Tyr Asp Tyr Asp Asp Ala Tyr Glu Asn Asn Ile Pro Ala
225                 230                 235                 240

Asn Ile Lys Ala Leu Ile Ile Ser Tyr Val Asn Gln Asn Tyr Pro Gly
                245                 250                 255

Ala Val Ile His Ser Ile Glu Arg Asn Ser Asn Gly Thr Tyr Asp Val
            260                 265                 270

Glu Ile Tyr Tyr Asn Asn Arg Glu Tyr Asp Leu Leu Phe Asp Ala Gln
        275                 280                 285

Gly Asn Leu Ile Ser Gly Asn Val Asp Gln Asp Asp Asp Asn
290                 295                 300

Ile Pro Ala His Ile Lys Ala Lys Ile Ile Asn Tyr Val Asn Arg Asn
305                 310                 315                 320

Tyr Pro Gly Ala Phe Ile Lys Asp Ile Glu Arg Lys Ser Asn Gly Thr
                325                 330                 335

Tyr Lys Ala Glu Ile Val Tyr Asn Asn Lys Glu Tyr Asp Leu Leu Phe
            340                 345                 350
```

Asp Ala Gln Gly Asn Phe Ile Ser Ala Ser Leu Asp Asp Lys Lys
        355                 360                 365

<210> SEQ ID NO 7
<211> LENGTH: 480
<212> TYPE: DNA
<213> ORGANISM: Porphyromonas gingivalis

<400> SEQUENCE: 7
atgaaaataa gcgaaaacgt aactaaagcg atcaatgacc aaatcaaggc cgaaatgtgg      60
tcttcaaacc tctatttgtc catgtctgtg cattttgcgc aggtagggta caacggcttt     120
gctcattggc tcaaaaagca gagcctcgag gaaatggaac atgcctacga tatgatggac     180
tacctcctga gcgtggcgg cgaggtgaag atagaagcta tcgatgccgt gccccagaag     240
ttcggctctg tattggaggt attccaacag gtgtacgaac acgagtgcaa agtgaccgaa     300
atgatcgagc tgtcgtaag gctgcttcc gaagccggag atatggcatc acaggacttc     360
ttctggaagt atatccgcga gcaggtagaa gaggaagcca ctgctgccga atcgtcgaa     420 acgatccgtc tctctcagga gcagaatctg atcttcatcg atcatcagct cgcccggaga     480

<210> SEQ ID NO 8
<211> LENGTH: 160
<212> TYPE: PRT
<213> ORGANISM: Porphyromonas gingivalis

<400> SEQUENCE: 8

Met Lys Ile Ser Glu Asn Val Thr Lys Ala Ile Asn Asp Gln Ile Lys
1               5                   10                  15

Ala Glu Met Trp Ser Ser Asn Leu Tyr Leu Ser Met Ser Val His Phe
            20                  25                  30

Ala Gln Val Gly Tyr Asn Gly Phe Ala His Trp Leu Lys Lys Gln Ser
        35                  40                  45

Leu Glu Glu Met Glu His Ala Tyr Asp Met Met Asp Tyr Leu Leu Lys
    50                  55                  60

Arg Gly Gly Glu Val Lys Ile Glu Ala Ile Asp Ala Val Pro Gln Lys
65                  70                  75                  80

Phe Gly Ser Val Leu Glu Val Phe Gln Gln Val Tyr Glu His Glu Cys
                85                  90                  95

Lys Val Thr Glu Met Ile Glu Ala Val Val Arg Ala Ala Ser Glu Ala
            100                 105                 110

Gly Asp Met Ala Ser Gln Asp Phe Phe Trp Lys Tyr Ile Arg Glu Gln
        115                 120                 125

Val Glu Glu Glu Ala Thr Ala Ala Glu Ile Val Glu Thr Ile Arg Leu
    130                 135                 140

Ser Gln Glu Gln Asn Leu Ile Phe Ile Asp His Gln Leu Ala Arg Arg
145                 150                 155                 160

<210> SEQ ID NO 9
<211> LENGTH: 1284
<212> TYPE: DNA
<213> ORGANISM: Porphyromonas gingivalis

<400> SEQUENCE: 9
atgaaacata tctgcttata cttccaaata catcagccgt tcgtctgaa acgataccga      60 tttttcgaca tcgggaacga ccattactac tacgacgact ccgcaatga agaaatcatg     120 cgacggatca cacagaagtg ctatctgccg gccaatctgc ttttgaagga aatcattgcc     180

-continued

```
gaacatcccg agtttcgagt agcatttct atttccggta ctgctttgga acagctggag    240
tcctattcgc cggaggcctt ggacaccttc agagatttgg ccgaaacggg ctgtgtagag    300
tttctggccg aaacctacgc tcattccctc tcgtcgctct atgatcccga gaattttac     360 aatcagacga tgatccatag tcgtcggatg aagagctgt tcggtgtaaa accccgagtg     420
ctgcgcaata cagagttgat cttctccgac aacattgcca cccaagtggc agaaatgggt    480
tttcaaggga tgctcacgga aggagccaaa cacatactcg gatggaagag tccgaactat    540
ctgtacaaag ccggatccgc tccggagttg tccctcttgc tccgcaatcc gaggctgagc    600
gatgccatca gtgccatgtt cacccgctac gattggaacg aatatcccct gacggcagac    660
aagatgatcc gttggatcga agagactccc gaagaggagc agatattcaa tctcttcatg    720
aactacgaag tcttgggatc gctccatccg caggagtcgg gtattttcga tttctttcgt    780
gcactccctt ctttggcgaa aaagagcgaa ggtgtcaaat tcgctacgcc atcggagttg    840
atagagtcct ccagccccgt agccaagttc tcctccatct accccataag ctgggtagga    900
gaagaaaaag ataccggtac gtggctgggc aatgtgctgc aacaaggagc atgcgacaaa    960
ctcgaacaat ggggcgaacg tgtacgtatg atcgacgatc agcgtatgct acaggactgg   1020
ctctatctac agagcgccga ccacttctac tatatgaaaa cccgtggcgg agacgccggc   1080
aacttcagcc cgtacgaaac gccttacgat gctttcaaca actatatgaa tgtgctcagc   1140
gacttcctgc ttcgcgtaga agcccgctac ccttctacga tagaaaatga agaactgaaa   1200
gccttgctga ctacaatcag aaatcaggat aaacaaatca aaaattagag agacaatc    1260 aaacgtcaaa aacgaaaac aaca                                           1284
```

<210> SEQ ID NO 10
<211> LENGTH: 428
<212> TYPE: PRT
<213> ORGANISM: Porphyromonas gingivalis

<400> SEQUENCE: 10

```
Met Lys His Ile Cys Leu Tyr Phe Gln Ile His Gln Pro Phe Arg Leu
1               5                   10                  15

Lys Arg Tyr Arg Phe Asp Ile Gly Asn Asp His Tyr Tyr Tyr Asp
            20                  25                  30

Asp Phe Arg Asn Glu Glu Ile Met Arg Arg Ile Thr Gln Lys Cys Tyr
        35                  40                  45

Leu Pro Ala Asn Leu Leu Lys Glu Ile Ile Ala Glu His Pro Glu
    50                  55                  60

Phe Arg Val Ala Phe Ser Ile Ser Gly Thr Ala Leu Glu Gln Leu Glu
65                  70                  75                  80

Ser Tyr Ser Pro Glu Ala Leu Asp Thr Phe Arg Asp Leu Ala Glu Thr
                85                  90                  95

Gly Cys Val Glu Phe Leu Ala Glu Thr Tyr Ala His Ser Leu Ser Ser
            100                 105                 110

Leu Tyr Asp Pro Glu Glu Phe Tyr Asn Gln Thr Met Ile His Ser Arg
        115                 120                 125

Arg Met Glu Glu Leu Phe Gly Val Lys Pro Arg Val Leu Arg Asn Thr
    130                 135                 140

Glu Leu Ile Phe Ser Asp Asn Ile Ala Thr Gln Val Ala Glu Met Gly
145                 150                 155                 160

Phe Gln Gly Met Leu Thr Glu Gly Ala Lys His Ile Leu Gly Trp Lys
                165                 170                 175
```

```
Ser Pro Asn Tyr Leu Tyr Lys Ala Gly Ser Ala Pro Glu Leu Ser Leu
            180                 185                 190

Leu Leu Arg Asn Pro Arg Leu Ser Asp Ala Ile Ser Ala Met Phe Thr
        195                 200                 205

Arg Tyr Asp Trp Asn Glu Tyr Pro Leu Thr Ala Asp Lys Met Ile Arg
    210                 215                 220

Trp Ile Glu Glu Thr Pro Glu Glu Gln Ile Phe Asn Leu Phe Met
225                 230                 235                 240

Asn Tyr Glu Val Leu Gly Ser Leu His Pro Gln Glu Ser Gly Ile Phe
                245                 250                 255

Asp Phe Phe Arg Ala Leu Pro Ser Leu Ala Lys Lys Ser Glu Gly Val
            260                 265                 270

Lys Phe Ala Thr Pro Ser Glu Leu Ile Glu Ser Ser Pro Val Ala
        275                 280                 285

Lys Phe Ser Ser Ile Tyr Pro Ile Ser Trp Val Gly Glu Lys Asp
    290                 295                 300

Thr Gly Thr Trp Leu Gly Asn Val Leu Gln Gln Gly Ala Cys Asp Lys
305                 310                 315                 320

Leu Glu Gln Trp Gly Glu Arg Val Arg Met Ile Asp Asp Gln Arg Met
                325                 330                 335

Leu Gln Asp Trp Leu Tyr Leu Gln Ser Ala Asp His Phe Tyr Tyr Met
            340                 345                 350

Lys Thr Arg Gly Gly Asp Ala Gly Asn Phe Ser Pro Tyr Glu Thr Pro
        355                 360                 365

Tyr Asp Ala Phe Asn Asn Tyr Met Asn Val Leu Ser Asp Phe Leu Leu
    370                 375                 380

Arg Val Glu Ala Arg Tyr Pro Ser Thr Ile Glu Asn Glu Glu Leu Lys
385                 390                 395                 400

Ala Leu Leu Thr Thr Ile Arg Asn Gln Asp Lys Gln Ile Lys Lys Leu
                405                 410                 415

Glu Glu Thr Ile Lys Arg Gln Lys Thr Lys Thr Thr
            420                 425

<210> SEQ ID NO 11
<211> LENGTH: 544
<212> TYPE: PRT
<213> ORGANISM: Porphyromonas gingivalis

<400> SEQUENCE: 11

Met Ala Lys Glu Ile Lys Phe Asp Met Glu Ser Arg Asp Leu Leu Lys
1               5                   10                  15

Lys Gly Val Asp Ala Leu Ala Asn Ala Val Lys Val Thr Leu Gly Pro
            20                  25                  30

Lys Gly Arg Asn Val Ile Leu Ser Lys Thr Tyr Gly Ala Pro His Ile
        35                  40                  45

Thr Lys Asp Gly Val Ser Val Ala Lys Glu Ile Glu Leu Glu Cys Pro
    50                  55                  60

Phe Glu Asn Met Gly Ala Gln Leu Val Lys Glu Val Ala Ser Lys Thr
65                  70                  75                  80

Asn Asp Asp Ala Gly Asp Gly Thr Thr Thr Ala Thr Ile Leu Ala Gln
                85                  90                  95

Ser Ile Ile Gly Val Gly Leu Lys Asn Val Thr Ala Gly Ala Asn Pro
            100                 105                 110

Met Asp Leu Lys Arg Gly Ile Asp Lys Ala Val Lys Ala Val Val Thr
```

-continued

```
            115                 120                 125
His Ile Ala Gly Met Ala Lys Glu Val Gly Asp Phe Gln Lys Ile
            130                 135                 140
Glu His Val Ala Lys Ile Ser Ala Asn Gly Asp Glu Asn Ile Gly Ser
145                 150                 155                 160
Leu Ile Ala Glu Ala Met Arg Lys Val Lys Lys Glu Gly Val Ile Thr
                165                 170                 175
Val Glu Glu Ala Lys Gly Thr Asp Thr Thr Val Glu Val Val Glu Gly
                180                 185                 190
Met Gln Phe Asp Arg Gly Tyr Ile Ser Pro Tyr Phe Val Thr Asn Thr
                195                 200                 205
Asp Lys Met Glu Val Gln Met Glu Asn Pro Phe Ile Leu Ile Tyr Asp
            210                 215                 220
Lys Lys Ile Ser Val Leu Lys Glu Met Leu Pro Ile Leu Glu Gln Thr
225                 230                 235                 240
Val Gln Thr Gly Lys Pro Leu Leu Ile Ile Ala Glu Asp Ile Asp Ser
                245                 250                 255
Glu Ala Leu Ala Thr Leu Val Val Asn Arg Leu Arg Gly Ser Leu Lys
            260                 265                 270
Ile Cys Ala Val Lys Ala Pro Gly Phe Gly Asp Arg Arg Lys Ala Met
            275                 280                 285
Leu Glu Asp Ile Ala Ile Leu Thr Gly Gly Thr Val Ile Ser Glu Glu
            290                 295                 300
Thr Gly Leu Lys Leu Glu Asn Ala Thr Met Asp Met Leu Gly Thr Ala
305                 310                 315                 320
Glu Lys Val Thr Val Asp Lys Asp Asn Thr Thr Ile Val Asn Gly Ala
                325                 330                 335
Gly Asn Lys Glu Gly Ile Ala Ser Arg Ile Thr Gln Ile Lys Ala Gln
            340                 345                 350
Ile Glu Asn Thr Thr Ser Asp Tyr Asp Arg Glu Lys Leu Gln Glu Arg
            355                 360                 365
Leu Ala Lys Leu Ala Gly Gly Val Ala Val Leu Tyr Val Gly Ala Ala
            370                 375                 380
Ser Glu Val Glu Met Lys Glu Lys Lys Asp Arg Val Glu Asp Ala Leu
385                 390                 395                 400
Ser Ala Thr Arg Ala Ala Ile Glu Glu Gly Thr Val Pro Gly Gly Gly
                405                 410                 415
Thr Ala Tyr Ile Arg Ala Ile Ala Ala Leu Glu Gly Leu Lys Gly Glu
                420                 425                 430
Asn Glu Asp Glu Thr Thr Gly Ile Glu Ile Val Lys Arg Ala Ile Glu
            435                 440                 445
Glu Pro Leu Arg Gln Ile Val Ala Asn Ala Gly Lys Glu Gly Ala Val
            450                 455                 460
Val Val Gln Lys Val Lys Glu Gly Lys Asp Asp Phe Gly Tyr Asn Ala
465                 470                 475                 480
Arg Thr Asp Val Phe Glu Asn Leu Tyr Thr Thr Gly Val Ile Asp Pro
                485                 490                 495
Ala Lys Val Thr Arg Val Ala Leu Glu Asn Ala Ala Ser Ile Ala Gly
                500                 505                 510
Met Phe Leu Thr Thr Glu Cys Val Ile Ala Asp Lys Lys Glu Asp Asn
            515                 520                 525
Pro Ala Ala Pro Ala Met Pro Gly Gly Met Gly Gly Met Gly Gly Met
            530                 535                 540
```

<210> SEQ ID NO 12
<211> LENGTH: 515
<212> TYPE: PRT
<213> ORGANISM: Porphyromonas gingivalis

<400> SEQUENCE: 12

```
Met Leu Asp Lys Asp Thr Leu Ala Gln Val Gly Ser Tyr Phe Ala Gln
1               5                   10                  15

Leu Lys Lys Ser Tyr Thr Leu Arg Leu Asn Ala His Thr Ser His Pro
            20                  25                  30

Ser Tyr Asn Glu Ala Lys Glu Met Leu Asp Gly Leu Ala Ser Val Ser
        35                  40                  45

Asp His Val Arg Ala Glu Tyr Asn Ala Ala Asp Phe Arg Ile Asp
    50                  55                  60

Leu Leu Val Asp Gly Ala Asp Ser Gly Ile Gly Phe Arg Gly Ile Pro
65                  70                  75                  80

Gly Gly His Glu Phe Ser Ser Leu Leu Leu Ala Ile Leu Asn Asn Asp
                85                  90                  95

Gly Ile Gly Arg Asn Ile Pro Asp Glu Gly Val Gln Asp Arg Ile Arg
            100                 105                 110

Arg Ile Asn Gly Pro Ile Glu Leu Lys Thr Tyr Val Ser Leu Ser Cys
        115                 120                 125

Thr Asn Cys Pro Asp Val Val Gln Thr Leu Asn Met Ile Ala Ile Leu
    130                 135                 140

Asn Pro Thr Ile Asn His Thr Met Val Asp Gly Ser Phe Phe Pro Asp
145                 150                 155                 160

Glu Val Glu Ser Leu Gly Ile Ala Ser Val Pro Thr Val Met Ala Gly
                165                 170                 175

Asp Glu Val Ile His Val Gly Arg Gly Asp Met Ala Ala Leu Leu Asn
            180                 185                 190

Lys Ile Glu Ala Lys Tyr Gly Ser Val Pro Ala Glu Ser Ala Asp Lys
        195                 200                 205

Thr Leu Arg Pro Phe Asp Leu Leu Val Val Gly Gly Pro Ala Gly
    210                 215                 220

Ser Ala Ala Ile Tyr Ser Ala Arg Lys Gly Leu Lys Val Ala Ile
225                 230                 235                 240

Val Ala Glu Arg Val Gly Gly Gln Val Asn Glu Thr Val Gly Ile Glu
                245                 250                 255

Asn Leu Ile Ser Val Pro Tyr Thr Thr Gly Ser Glu Leu Ala Ser Asn
            260                 265                 270

Leu Asn Ser His Ile Lys Ala Asn Thr Ile Ser Leu Phe Glu Ala Arg
        275                 280                 285

Thr Val Ser Ser Ile Thr Gln Gln Glu Gly Ile Ser Arg Val Glu Val
    290                 295                 300

Thr Ser Gly Glu Val Phe Thr Ala Pro Ala Leu Ile Met Ala Thr Gly
305                 310                 315                 320

Ala Ser Trp Arg Lys Leu Gly Val Pro Gly Lys Glu Tyr Thr Gly
                325                 330                 335

Asn Gly Val Ala Tyr Cys Ala His Cys Asp Gly Pro Phe Phe Lys Gly
            340                 345                 350

Lys Arg Val Ala Val Val Gly Gly Asn Ser Gly Leu Glu Ala Ala
        355                 360                 365

Ile Asp Leu Ala Gly Ile Cys Glu His Val Thr Val Val Glu Phe Leu
```

-continued

```
                370                 375                 380
Asp Val Leu Arg Ala Asp Glu Val Leu Gln Lys Ala Arg Glu Thr
385                 390                 395                 400

Ala Asn Ile Asp Ile Leu Leu Ser Thr Ala Thr Lys Glu Ile Met Gly
                405                 410                 415

Asn Gly Gln Lys Val Glu Gly Ile Leu Leu Thr Asp Arg Asn Thr Gly
                420                 425                 430

Glu Glu Lys Gln Ile Ala Leu Ser Gly Val Phe Val Gln Ile Gly Leu
                435                 440                 445

Ala Ala Asn Thr Ser Leu Val Lys Asp Leu Val Glu Thr Asn Ser Arg
                450                 455                 460

Gly Glu Val Leu Ile Asp Thr Ser Cys Arg Thr Asn Thr Pro Gly Ile
465                 470                 475                 480

Tyr Ala Ala Gly Asp Cys Thr Thr Val Pro Tyr Lys Gln Ile Val Ile
                485                 490                 495

Ala Met Gly Glu Gly Ala Lys Ala Leu Ser Ala Phe Glu Asp Arg
                500                 505                 510

Ile Arg Gly
        515

<210> SEQ ID NO 13
<211> LENGTH: 515
<212> TYPE: PRT
<213> ORGANISM: Porphyromonas gingivalis

<400> SEQUENCE: 13

Met Leu Asp Lys Asp Thr Leu Ala Gln Val Gly Ser Tyr Phe Ala Gln
1               5                   10                  15

Leu Lys Lys Ser Tyr Thr Leu Arg Leu Asn Ala His Thr Ser His Pro
                20                  25                  30

Ser Tyr Asn Glu Ala Lys Glu Met Leu Asp Gly Leu Ala Ser Val Ser
                35                  40                  45

Asp His Val Arg Ala Glu Tyr Asn Ala Ala Asp Asp Phe Arg Ile Asp
                50                  55                  60

Leu Leu Val Asp Gly Ala Asp Ser Gly Ile Gly Phe Arg Gly Ile Pro
65                  70                  75                  80

Gly Gly His Glu Phe Ser Ser Leu Leu Leu Ala Ile Leu Asn Asn Asp
                85                  90                  95

Gly Ile Gly Arg Asn Ile Pro Asp Glu Gly Val Gln Asp Arg Ile Arg
                100                 105                 110

Arg Ile Asn Gly Pro Ile Glu Leu Lys Thr Tyr Val Ser Leu Ser Cys
                115                 120                 125

Thr Asn Cys Pro Asp Val Val Gln Thr Leu Asn Met Ile Ala Ile Leu
                130                 135                 140

Asn Pro Thr Ile Asn His Thr Met Val Asp Gly Ser Phe Phe Pro Asp
145                 150                 155                 160

Glu Val Glu Ser Leu Gly Ile Ala Ser Val Pro Thr Val Met Ala Gly
                165                 170                 175

Asp Glu Val Ile His Val Gly Arg Gly Asp Met Ala Ala Leu Leu Asn
                180                 185                 190

Lys Ile Glu Ala Lys Tyr Gly Ser Val Pro Ala Glu Ser Ala Asp Lys
                195                 200                 205

Thr Leu Arg Pro Phe Asp Leu Leu Val Val Gly Gly Gly Pro Ala Gly
                210                 215                 220
```

```
Ser Ala Ala Ala Ile Tyr Ser Ala Arg Lys Gly Leu Lys Val Ala Ile
225                 230                 235                 240

Val Ala Glu Arg Val Gly Gly Gln Val Asn Glu Thr Val Gly Ile Glu
            245                 250                 255

Asn Leu Ile Ser Val Pro Tyr Thr Thr Gly Ser Glu Leu Ala Ser Asn
                260                 265                 270

Leu Asn Ser His Ile Lys Ala Asn Thr Ile Ser Leu Phe Glu Ala Arg
            275                 280                 285

Thr Val Ser Ser Ile Thr Gln Gln Glu Gly Ile Ser Arg Val Glu Val
        290                 295                 300

Thr Ser Gly Glu Val Phe Thr Ala Pro Ala Leu Ile Met Ala Thr Gly
305                 310                 315                 320

Ala Ser Trp Arg Lys Leu Gly Val Pro Gly Lys Glu Tyr Thr Gly
                325                 330                 335

Asn Gly Val Ala Tyr Cys Ala His Cys Asp Gly Pro Phe Phe Lys Gly
                340                 345                 350

Lys Arg Val Ala Val Val Gly Gly Asn Ser Gly Leu Glu Ala Ala
            355                 360                 365

Ile Asp Leu Ala Gly Ile Cys Glu His Val Thr Val Val Glu Phe Leu
        370                 375                 380

Asp Val Leu Arg Ala Asp Glu Val Leu Gln Lys Lys Ala Arg Glu Thr
385                 390                 395                 400

Ala Asn Ile Asp Ile Leu Leu Ser Thr Ala Thr Lys Glu Ile Met Gly
                405                 410                 415

Asn Gly Gln Lys Val Glu Gly Ile Leu Leu Thr Asp Arg Asn Thr Gly
            420                 425                 430

Glu Glu Lys Gln Ile Ala Leu Ser Gly Val Phe Val Gln Ile Gly Leu
        435                 440                 445

Ala Ala Asn Thr Ser Leu Val Lys Asp Leu Val Glu Thr Asn Ser Arg
450                 455                 460

Gly Glu Val Leu Ile Asp Thr Ser Cys Arg Thr Asn Thr Pro Gly Ile
465                 470                 475                 480

Tyr Ala Ala Gly Asp Cys Thr Thr Val Pro Tyr Lys Gln Ile Val Ile
                485                 490                 495

Ala Met Gly Glu Gly Ala Lys Ala Ala Leu Ser Ala Phe Glu Asp Arg
            500                 505                 510

Ile Arg Gly
        515

<210> SEQ ID NO 14
<211> LENGTH: 863
<212> TYPE: PRT
<213> ORGANISM: Porphyromonas gingivalis

<400> SEQUENCE: 14

Met Asn Ile Asn Asn Tyr Thr Ile Lys Ser Gln Glu Ala Leu Gln Gln
1               5                   10                  15

Ala Val Glu Leu Thr Arg Arg His Gly Gln Gln Ala Ile Glu Pro Gln
            20                  25                  30

His Leu Leu Lys Ala Val Met Asp Gln Gly Glu Ser Leu Thr Asp Phe
        35                  40                  45

Leu Phe Ala Lys Met Gly Leu Asn Lys Gly Ser Ile Ala Thr Ala Val
    50                  55                  60

Asp Lys Leu Ile Glu Lys Leu Pro His Val Ser Gly Gly Glu Pro Tyr
65                  70                  75                  80
```

-continued

```
Leu Ser His Glu Thr Asn Gln Val Leu Gln Ala Ala Glu Asp Ala Ala
                 85                  90                  95
His Arg Met Lys Asp Lys Tyr Val Ser Leu Glu His Ile Val Leu Ala
            100                 105                 110
Ile Leu Thr Thr Arg Cys Glu Ala Ser Thr Leu Leu Lys Asp Ala Gly
        115                 120                 125
Ala Thr Glu Gln Leu Leu Gln Ser Ala Ile Glu Leu Arg Lys Gly
    130                 135                 140
Arg Asn Val Thr Ser Gln Ser Ala Glu Glu Tyr Asn Ala Leu Glu
145                 150                 155                 160
Lys Tyr Ala Val Asn Leu Cys Gln Arg Ala Arg Asp Gly Lys Leu Asp
                165                 170                 175
Pro Val Ile Gly Arg Asp Glu Ile Arg Arg Val Leu Gln Ile Leu
            180                 185                 190
Ser Arg Arg Thr Lys Asn Asn Pro Ile Leu Ile Gly Glu Pro Gly Val
        195                 200                 205
Gly Lys Thr Ala Ile Ala Glu Gly Leu Ala Tyr Arg Ile Val Arg Gly
    210                 215                 220
Asp Val Pro Glu Asn Leu Arg Asn Lys Gln Ile Phe Ser Leu Asp Met
225                 230                 235                 240
Gly Ala Leu Ile Ala Gly Ala Lys Tyr Lys Gly Glu Phe Glu Glu Arg
                245                 250                 255
Leu Lys Ala Val Val Asn Glu Val Thr Gly Ala Glu Gly Glu Ile Ile
            260                 265                 270
Leu Phe Ile Asp Glu Ile His Thr Leu Val Gly Ala Gly Lys Ser Glu
        275                 280                 285
Gly Ala Met Asp Ala Ala Asn Ile Leu Lys Pro Ala Leu Ala Arg Gly
    290                 295                 300
Glu Leu Arg Ala Ile Gly Ala Thr Thr Leu Asp Glu Tyr Arg Lys Tyr
305                 310                 315                 320
Phe Glu Lys Asp Lys Ala Leu Glu Arg Arg Phe Gln Met Val Met Val
                325                 330                 335
Asp Glu Pro Asp Glu Leu Ser Ser Ile Ser Ile Leu Arg Gly Leu Lys
            340                 345                 350
Glu Lys Tyr Glu Asn His His Lys Val Arg Ile Lys Asp Asp Ala Ile
        355                 360                 365
Ile Ala Ala Val Lys Leu Ser His Arg Tyr Ile Thr Glu Arg Phe Leu
    370                 375                 380
Pro Asp Lys Ala Ile Asp Leu Met Asp Glu Ala Ala Ala Arg Leu Arg
385                 390                 395                 400
Met Glu Val Asp Ser Leu Pro Glu Glu Leu Asp Glu Ile Ser Arg Arg
                405                 410                 415
Ile Lys Gln Leu Glu Ile Glu Arg Glu Ala Ile Lys Arg Glu Asn Asp
            420                 425                 430
Glu Glu Lys Val Gln Phe Leu Asp Arg Glu Ile Ala Glu Leu Lys Glu
        435                 440                 445
Lys Glu Ala Ser Glu Lys Ala Gln Trp Gln Asn Glu Lys Asp Arg Ile
    450                 455                 460
Asn Gln Ile Gln Gln Leu Lys Ile Asp Ile Glu Leu Lys Phe Gln
465                 470                 475                 480
Ala Asp Arg Ala Glu Arg Glu Gly Asp Tyr Gly Arg Val Ala Glu Ile
                485                 490                 495
```

```
Arg Tyr Gly Leu Ile Lys Gln Lys Glu Thr Glu Ile Asp Thr Ile Gln
            500                 505                 510

Gln Gln Leu His Glu Leu Gln Arg Gly Gly Ser Met Ile Lys Glu Glu
        515                 520                 525

Val Glu Ala Asp Asp Ile Ala Asp Ile Val Ser Arg Trp Thr Gly Ile
    530                 535                 540

Pro Val Ser Arg Met Leu Gln Ser Glu Arg Asp Lys Leu Leu His Leu
545                 550                 555                 560

Glu Asp Glu Leu His Lys Arg Val Ile Gly Gln Asp Glu Ala Ile Arg
                565                 570                 575

Ala Val Ala Asp Ala Val Arg Arg Ser Arg Ala Gly Leu Gln Asp Pro
            580                 585                 590

Lys Arg Pro Ile Gly Ser Phe Ile Phe Leu Gly Thr Thr Gly Val Gly
        595                 600                 605

Lys Thr Glu Leu Ala Arg Ala Leu Ala Glu Leu Leu Phe Asp Asp Glu
    610                 615                 620

Ser Met Leu Thr Arg Ile Asp Met Ser Glu Tyr Gln Glu Lys Phe Ser
625                 630                 635                 640

Ala Thr Arg Leu Ile Gly Ala Pro Pro Gly Tyr Val Gly Tyr Asp Glu
                645                 650                 655

Gly Gly Gln Leu Thr Glu Ala Ile Arg Arg Lys Pro Tyr Ser Val Val
            660                 665                 670

Leu Phe Asp Glu Ile Glu Lys Ala His Pro Asp Val Phe Asn Val Leu
        675                 680                 685

Leu Gln Val Leu Asp Asp Gly Arg Leu Thr Asp Asn Lys Gly His Val
    690                 695                 700

Val Asn Phe Lys Asn Thr Leu Ile Ile Met Thr Ser Asn Leu Gly Ser
705                 710                 715                 720

Asp Ile Ile Arg Glu Arg Met Gln Asn Leu Thr Ala Glu Asn Arg Arg
                725                 730                 735

Ser Leu Thr Ala Arg Thr Ala Asp Glu Val Met Gln Leu Leu Lys His
            740                 745                 750

Thr Ile Arg Pro Glu Phe Leu Asn Arg Ile Asp Glu Thr Ile Val Phe
        755                 760                 765

Thr Pro Leu Thr Glu Lys Glu Ile Tyr Glu Ile Val Arg Leu Gln Leu
    770                 775                 780

Asp Gly Ile Val Arg Gln Leu Ala Asp Asn Asp Val Leu His Tyr
785                 790                 795                 800

Thr Glu Ala Val Val Thr Phe Ala Ala Arg Glu Gly Tyr Asp Pro Gln
                805                 810                 815

Phe Gly Ala Arg Pro Val Lys Arg Val Leu Gln Arg Phe Val Leu Asn
            820                 825                 830

Glu Leu Ser Lys Ala Leu Leu Ala Asp Thr Val Asp Ser Thr Arg Pro
        835                 840                 845

Val Leu Ile Asp Cys Ile Asp Gly Ser Ile Val Phe Arg Asn Glu
    850                 855                 860

<210> SEQ ID NO 15
<211> LENGTH: 640
<212> TYPE: PRT
<213> ORGANISM: Porphyromonas gingivalis

<400> SEQUENCE: 15

Met Gly Lys Ile Ile Gly Ile Asp Leu Gly Thr Thr Asn Ser Cys Val
1               5                   10                  15
```

```
Ser Val Leu Glu Gly Asn Glu Pro Ile Val Ile Thr Asn Ser Glu Gly
         20                  25                  30

Lys Arg Thr Thr Pro Ser Val Val Ala Phe Val Asp Gly Gly Glu Arg
         35                  40                  45

Lys Val Gly Asp Pro Ala Lys Arg Gln Ala Ile Thr Asn Pro Thr Lys
 50                  55                  60

Thr Ile Tyr Ser Ile Lys Arg Phe Met Gly Thr Tyr Asp Gln Val
 65                  70                  75                  80

Ser Arg Glu Val Glu Arg Val Pro Phe Lys Val Val Arg Gly Asp Asn
                     85                  90                  95

Asn Thr Pro Arg Val Asp Ile Asp Gly Arg Leu Tyr Thr Pro Gln Glu
                100                 105                 110

Ile Ser Ala Met Ile Leu Gln Lys Met Lys Thr Ala Glu Asp Tyr
                115                 120                 125

Leu Gly Gln Glu Val Thr Glu Ala Val Ile Thr Val Pro Ala Tyr Phe
130                 135                 140

Asn Asp Ala Gln Arg Gln Ala Thr Lys Glu Ala Gly Glu Ile Ala Gly
145                 150                 155                 160

Leu Lys Val Arg Arg Ile Val Asn Glu Pro Thr Ala Ala Ser Leu Ala
                165                 170                 175

Tyr Gly Leu Asp Lys Ser Asn Lys Asp Met Lys Ile Ala Val Phe Asp
                180                 185                 190

Leu Gly Gly Gly Thr Phe Asp Ile Ser Ile Leu Glu Leu Gly Asp Gly
                195                 200                 205

Val Phe Glu Val Lys Ser Thr Asn Gly Asp Thr His Leu Gly Gly Asp
210                 215                 220

Asp Phe Asp His Val Ile Ile Asp Trp Leu Ala Glu Glu Phe Lys Ser
225                 230                 235                 240

Gln Glu Gly Val Asp Leu Arg Gln Asp Pro Met Ala Met Gln Arg Leu
                245                 250                 255

Lys Glu Ala Ala Glu Lys Ala Lys Ile Glu Leu Ser Ser Thr Ser Ser
                260                 265                 270

Thr Glu Ile Asn Leu Pro Tyr Ile Met Pro Val Asn Gly Ile Pro Lys
                275                 280                 285

His Leu Val Met Thr Leu Thr Arg Ala Lys Phe Glu Gln Leu Ala Asp
                290                 295                 300

Arg Leu Ile Gln Ala Cys Val Ala Pro Cys Glu Thr Ala Leu Lys Asp
305                 310                 315                 320

Ala Gly Met Ser Arg Gly Asp Ile Asp Glu Val Ile Leu Val Gly Gly
                325                 330                 335

Ser Thr Arg Ile Pro Ala Ile Gln Glu Ile Val Glu Lys Ile Phe Gly
                340                 345                 350

Lys Ala Pro Ser Lys Gly Val Asn Pro Asp Glu Val Val Ala Val Gly
                355                 360                 365

Ala Ala Ile Gln Gly Gly Val Leu Thr Gly Glu Val Lys Asp Val Leu
370                 375                 380

Leu Leu Asp Val Thr Pro Leu Ser Leu Gly Ile Glu Thr Met Gly Gly
385                 390                 395                 400

Val Met Thr Arg Leu Ile Asp Ala Asn Thr Thr Ile Pro Thr Lys Lys
                405                 410                 415

Ser Glu Ile Phe Thr Thr Ala Val Asp Asn Gln Pro Ser Val Glu Ile
                420                 425                 430
```

```
His Val Leu Gln Gly Glu Arg Ser Leu Ala Lys Asp Asn Lys Ser Ile
            435                 440                 445

Gly Arg Phe Asn Leu Asp Gly Ile Ala Pro Ala Pro Arg Gln Thr Pro
        450                 455                 460

Gln Ile Glu Val Thr Phe Asp Ile Asp Ala Asn Gly Ile Leu Asn Val
465                 470                 475                 480

Thr Ala His Asp Lys Ala Thr Gly Lys Lys Gln Asn Ile Arg Ile Glu
                485                 490                 495

Ala Ser Ser Gly Leu Ser Asp Asp Glu Ile Lys Arg Met Lys Glu Glu
            500                 505                 510

Ala Gln Ala Asn Ala Glu Ala Asp Lys Lys Glu Lys Glu Arg Ile Asp
        515                 520                 525

Lys Ile Asn Gln Ala Asp Ser Met Ile Phe Gln Thr Glu Lys Gln Leu
530                 535                 540

Lys Glu Leu Gly Asp Lys Phe Pro Ala Asp Lys Lys Ala Pro Ile Asp
545                 550                 555                 560

Thr Ala Leu Asp Lys Leu Lys Glu Ala His Lys Ala Gln Asp Val Ala
                565                 570                 575

Ala Ile Asp Thr Ala Met Ala Glu Leu Gln Thr Ala Leu Ser Ala Ala
            580                 585                 590

Gly Glu Glu Leu Tyr Lys Asn Ala Gly Ala Ala Gln Gly Gly Ala Gln
        595                 600                 605

Pro Gly Pro Asp Phe Gly Gly Ala Gln Gly Pro Ser Ala Gly Asp Gln
610                 615                 620

Pro Ser Asp Asp Lys Asn Val Thr Asp Val Asp Phe Glu Glu Val Lys
625                 630                 635                 640

<210> SEQ ID NO 16
<211> LENGTH: 168
<212> TYPE: PRT
<213> ORGANISM: Porphyromonas gingivalis

<400> SEQUENCE: 16

Met Asn Thr Ile Ala Phe Lys Glu Ile Phe Leu Pro Ile Arg Pro Ser
1               5                   10                  15

Ile Arg Ala Val Cys His Ala Phe Leu Arg Asp Asp Glu Glu Ala Glu
            20                  25                  30

Asp Ala Thr Gln Glu Val Tyr Leu Arg Leu Trp Glu Ala Arg Met Arg
        35                  40                  45

Leu Asp Gly Leu Asp Asn Pro Arg Ala Tyr Ala Ile Arg Ile Ala Arg
    50                  55                  60

Asn Tyr Cys Leu Asn Leu Ile Arg Lys Ala Ser Asn Ser Pro Tyr Pro
65                  70                  75                  80

Thr Ser Leu Glu Ala Ala Glu Val Gln Glu Val Ser Glu Thr His Gly
                85                  90                  95

Gly Glu Ala Asp Leu Leu Leu Ser Glu Gln Ile Gly Arg Leu Arg Gln
            100                 105                 110

Trp Leu Arg Gly Val Ser Glu Leu Tyr Arg Thr Val Phe Ala Met Ser
        115                 120                 125

His Phe Arg Arg Leu Ser Asn Gly Glu Ile Ala Glu Arg Leu Gly Leu
    130                 135                 140

Thr Glu Gly Asn Val Arg Val Ile Leu Cys Arg Leu Arg Arg Glu Ala
145                 150                 155                 160

Lys Glu Val Met Lys Asp Asp Ala
                165
```

<210> SEQ ID NO 17
<211> LENGTH: 405
<212> TYPE: PRT
<213> ORGANISM: Porphyromonas gingivalis

<400> SEQUENCE: 17

```
Met Lys Lys Thr Thr Ile Ile Ser Leu Ile Val Phe Gly Ala Phe Phe
1               5                   10                  15

Ala Ala Val Gly Gln Thr Lys Asp Asn Ser Ser Tyr Lys Pro Phe Ser
            20                  25                  30

Lys Glu Asp Ile Ala Gly Gly Val Tyr Ser Leu Pro Thr Gln Asn Arg
        35                  40                  45

Ala Gln Lys Asp Asn Ala Glu Trp Leu Leu Thr Ala Thr Val Ser Thr
    50                  55                  60

Asn Gln Ser Ala Asp Thr His Phe Ile Phe Asp Glu Asn Asn Arg Tyr
65                  70                  75                  80

Ile Ala Arg Asp Ile Lys Ala Asn Gly Val Arg Lys Ser Thr Asp Ser
                85                  90                  95

Ile Tyr Tyr Asp Ala Asn Gly Arg Ile Ser His Val Asp Leu Tyr Ile
            100                 105                 110

Ser Phe Ser Gly Gly Glu Pro Ala Leu Asp Thr Arg Phe Lys Tyr Thr
        115                 120                 125

Tyr Asp Asp Glu Gly Lys Met Thr Val Arg Glu Val Phe Met Leu Val
    130                 135                 140

Met Asp Pro Asn Thr Pro Ile Ser Arg Leu Glu Tyr His Tyr Asp Ala
145                 150                 155                 160

Gln Gly Arg Leu Thr His Trp Ile Ser Phe Ala Phe Gly Ala Glu Ser
                165                 170                 175

Gln Lys Asn Thr Tyr His Tyr Asn Glu Lys Gly Leu Leu Val Ser Glu
            180                 185                 190

Val Leu Ser Asn Ala Met Gly Thr Thr Tyr Ser Asp Thr Gly Lys Thr
        195                 200                 205

Glu Tyr Ser Tyr Asp Asp Ala Asp Asn Met Val Lys Ala Glu Tyr Phe
    210                 215                 220

Val Val Gln Gln Gly Lys Ala Trp Gln Val Leu Lys Arg Glu Glu Tyr
225                 230                 235                 240

Thr Tyr Glu Asp Asn Ile Cys Ile Gln Tyr Leu Ala Ile Asn Gly Thr
                245                 250                 255

Asp Thr Lys Val Tyr Lys Arg Asp Ile Glu Ser Asp Lys Ser Ile Ser
            260                 265                 270

Ala Asn Val Ile Asp Ile Pro Ser Met Pro Glu Gln Thr Trp Pro Asn
        275                 280                 285

Met Tyr Gly Phe Asn Ala Lys Arg Leu Lys Glu Thr Tyr Ser Ser Tyr
    290                 295                 300

Glu Gly Asp Val Ala Thr Pro Ile Phe Asp Tyr Ile Tyr Thr Tyr Lys
305                 310                 315                 320

Ala Leu Thr Ser Met Ala Thr Pro Ser Thr Glu Ala Gln Val Ala Val
                325                 330                 335

Tyr Leu Asn Pro Ser Thr Asp Arg Leu Val Ile Leu Ala Asn Gly Ile
            340                 345                 350

Thr His Leu Ser Met Tyr Asp Leu Gln Gly Lys Leu Ile Arg Asp Cys
        355                 360                 365

Ala Leu Ser Gly Asp Lys Val Glu Met Gly Val Gly Ser Leu Thr Lys
```

```
                370             375             380
Gly Thr Tyr Leu Leu Lys Val Asn Thr Asp Gln Gly Ala Phe Val Arg
385                 390                 395                 400

Lys Val Val Ile Arg
            405

<210> SEQ ID NO 18
<211> LENGTH: 462
<212> TYPE: PRT
<213> ORGANISM: Porphyromonas gingivalis

<400> SEQUENCE: 18

Met Asn Arg Phe Ser Asn His Trp Pro Cys Ile Leu Val Gly Phe Val
1               5                   10                  15

Leu Trp Phe Val Ser Ala Ser Arg Thr Val Ala Gln Asn Ala Ser Glu
                20                  25                  30

Thr Thr Val Ser Tyr Asp Thr Asp Thr Ala Val Leu Ser Glu Ala Asp
            35                  40                  45

Val Leu Arg Ile Ala Leu Ser Glu Asn Ala Thr Val Lys Val Ala Asp
        50                  55                  60

Met Asp Val Arg Lys Gln Glu Tyr Ala Arg Ala Ala Arg Ala Asp
65                  70                  75                  80

Leu Phe Pro Lys Val Asp Leu Asn Gly Val Tyr Ser His Thr Leu Lys
                85                  90                  95

Lys Gln Val Leu Tyr Ile Asp Met Pro Gly Phe Ser Ser Glu Gly
            100                 105                 110

Ile Glu Met Gly Arg Thr His Asn Thr Gln Gly Gly Val Asn Val Ser
        115                 120                 125

Met Pro Leu Val Ser Ala Gln Leu Trp Lys Ser Ile Ala Met Thr Gly
130                 135                 140

Glu Gln Leu Asp Leu Ala Leu Glu Lys Ala Arg Ser Ser Arg Ile Asp
145                 150                 155                 160

Leu Val Ala Glu Val Lys Lys Ala Tyr Leu Ser Val Leu Leu Ala Glu
                165                 170                 175

Asp Ser Tyr Gly Val Phe Lys Arg Ser Tyr Asp Asn Ala Leu Ala Asn
            180                 185                 190

Tyr Lys Asn Ile Ser Asp Lys Phe Asp Arg Gly Leu Val Ala Glu Tyr
        195                 200                 205

Asp Lys Ile Arg Ala Asn Val Gln Val Arg Asn Ile Glu Pro Asn Leu
210                 215                 220

Leu Gln Ala Gln Asn Ser Val Ala Leu Ala Leu Trp Gln Leu Lys Val
225                 230                 235                 240

Leu Met Ser Met Glu Val Glu Thr Pro Ile Arg Leu Ser Gly Ser Leu
                245                 250                 255

Ser Asp Tyr Lys Glu Gln Val Thr Gly Tyr Phe Ala Ala Asp Thr
            260                 265                 270

Leu Ile Ser Asn Asn Ser Ser Leu Arg Gln Leu Asp Ile Gln Arg Arg
        275                 280                 285

Leu Ala Val Ser Ala Asp Lys Leu Asn Lys Tyr Ser Phe Leu Pro Thr
290                 295                 300

Leu Asn Leu Gly Gly Gln Tyr Thr Tyr Ser Leu Asn Ser Asn Asp Ile
305                 310                 315                 320

Lys Phe Trp Gly Glu Gly Gln Arg Trp Thr Pro Phe Ser Thr Ile Ser
                325                 330                 335
```

```
Leu Ser Leu Tyr Ile Pro Ile Phe Asn Gly Lys Arg Leu Tyr Asn
            340                 345                 350

Val Lys Gln Ser Ala Leu Ser Ile Arg Gln Ile Asp Leu Gln Arg Arg
            355                 360                 365

His Ile Glu Gln Ser Ile Arg Met Gly Ile Lys Asn Gln Asn Asp Arg
        370                 375                 380

Leu Arg Thr Cys Met Gln Arg Phe Val Ala Ser Glu Glu Ala Val Arg
385                 390                 395                 400

Ser Ala Glu Lys Gly Tyr Gln Ile Ala Glu Lys Arg Tyr Gln Thr Gly
                405                 410                 415

Glu Gly Thr Leu Val Glu Leu Asn Asp Ala Asp Val Ala Leu Leu Gln
                420                 425                 430

Ala Arg Leu Asn Tyr Asn Gln Ala Ile Phe Asp Phe Met Thr Ala Lys
            435                 440                 445

Ala Glu Leu Asp Lys Met Asn Gly Met Gly Ile Pro Glu Gln
        450                 455                 460

<210> SEQ ID NO 19
<211> LENGTH: 316
<212> TYPE: PRT
<213> ORGANISM: Porphyromonas gingivalis

<400> SEQUENCE: 19

Met Lys Thr Asn Ile Lys Met Arg Lys Thr Ile Ile Phe Cys Leu Leu
1               5                   10                  15

Leu Ala Leu Phe Gly Cys Ser Trp Ala Gln Glu Arg Val Asp Glu Lys
            20                  25                  30

Val Phe Ser Ala Gly Thr Ser Ile Phe Arg Gly Ile Leu Glu Lys Val
        35                  40                  45

Lys Ala Pro Leu Met Tyr Gly Asp Arg Glu Val Trp Gly Met Ala Arg
    50                  55                  60

Ala Ser Glu Asp Phe Phe Ile Leu Pro Val Thr Asp Asp Leu Thr
65                  70                  75                  80

Pro Val Leu Phe Tyr Asn Arg Leu Thr Asn Glu Pro Cys Phe Val Ser
                85                  90                  95

Asp Gln Gly Ile Thr Glu Tyr Phe Lys Phe Ala Gln Glu Gly Asp Tyr
            100                 105                 110

Ile Glu Val Glu Gly Ser Ser Val Phe Met Ala Asn Leu Leu Tyr Tyr
        115                 120                 125

Arg Phe Phe Pro Thr Arg Ile Ser Tyr Asn Ala Pro Ile Glu Gly
    130                 135                 140

Val Val Ser Lys Thr Gly Asn Pro Ala Phe Thr Ile Pro Met Leu Pro
145                 150                 155                 160

Gly Val Ser Asp Cys Ile Glu Ile Ser Asn Asn Arg Lys Val Phe Leu
                165                 170                 175

Thr Asn Gln Leu Gly Val Val Asn Ile Thr Asp Gly Met Glu Pro Pro
            180                 185                 190

Ile Ile Ala Gly Val Ser Ala Ser Tyr Gly Ser Ser Val Arg Val Tyr
        195                 200                 205

Gly His Val Ser Gln Arg Trp Asp Ile Ile Gly His Cys Tyr Leu Asp
    210                 215                 220

Ile Tyr Pro Thr Asn Cys Tyr Pro Leu Ser Thr Lys Pro Val Ala Gly
225                 230                 235                 240

Asp Asp Glu Val Phe Val Lys Gln Gln Gly Arg Gln Ile Glu Ile Asp
                245                 250                 255
```

```
Ser Asn Ser Pro Ile Val Gln Val Val Tyr Asp Leu Glu Gly Lys
            260                 265                 270

Ser Val Phe Arg Lys Arg Met Thr Glu Asn Ala Tyr Thr Leu Ser Phe
        275                 280                 285

Arg Ala Pro Met Leu Gly Phe Met Thr Ile Met Ile Glu Thr Gln Asn
    290                 295                 300

Ser Ile Ile Asn Lys Lys Leu Asn Val Thr Gln Leu
305                 310                 315

<210> SEQ ID NO 20
<211> LENGTH: 326
<212> TYPE: PRT
<213> ORGANISM: Porphyromonas gingivalis

<400> SEQUENCE: 20

Met Pro Lys Gln Tyr His Asn Lys Asn Glu His Lys Met Lys Gln Thr
1               5                   10                  15

Ile Leu Gly Ile Gln Leu Ser Gln Trp Thr Lys Cys Phe Leu Ser Phe
            20                  25                  30

Phe Leu Ile Ala Gly Cys Thr Gly Ala Leu Ser Gly Gln Ser Pro Ser
        35                  40                  45

Gln Ser Arg Gly Tyr Ala Thr Thr Gly Ile Leu Glu Pro Val Met Leu
    50                  55                  60

Pro Asp Thr Val Pro Val Asp Tyr His Ser Ala Trp Gly Met Val Cys
65                  70                  75                  80

Asp Ala Gln Leu Asn Ala Phe Asp Lys Pro Ile Ala Phe Arg Ala Pro
                85                  90                  95

Phe Ser Tyr Gln Gly Lys Gly Tyr Tyr Pro Thr Ala Tyr Tyr Gly
            100                 105                 110

Gly Leu Arg Glu Phe Cys Pro Tyr Ala Lys Leu Gly Asp Met Leu Ile
        115                 120                 125

Thr Glu Gly Arg Phe His Glu Phe Asp Ala Tyr Tyr Glu Leu Met Cys
    130                 135                 140

Thr Arg Ile Thr Leu Pro Asn Arg Thr Phe Glu Gly Val Val Thr Glu
145                 150                 155                 160

Ile Pro Met Pro Gln Phe Thr Tyr Pro Glu Val Thr Ala Thr Ile Val
                165                 170                 175

Cys Val Lys Asp Asp Ser Gly Phe Glu Ile Ala Ile Lys Asp Asp Glu
            180                 185                 190

Gly Asn Phe Ile Ser Ser Glu Asn Gly Glu Val Met Ile Ala Gly Asn
        195                 200                 205

Ser Tyr Pro Leu Gln Thr Arg Val Arg Val Glu Gly Asp Ile Val Gln
    210                 215                 220

Asp Tyr Gln Leu Lys Tyr Pro Ile Ile Phe Tyr Ser Thr Val Ala Lys
225                 230                 235                 240

Ser Cys His Thr Thr Asp Ser Gln Thr Val Val Pro Ser Ser Asn Asp
                245                 250                 255

Ile Asn Val Tyr Ile Gln Gly Thr Thr Ile Gly Ile Lys Ala Glu Lys
            260                 265                 270

Leu Ile Lys Ser Val Tyr Ile Tyr Asp Met Ala Gly Arg Met Leu Phe
        275                 280                 285

Ala Thr Ser Gln Thr Gln Gly Arg Glu Phe Cys Ile Asp Leu Lys Thr
    290                 295                 300

Lys Gly His Ile Leu Val Thr Val Leu Phe Ala Asp Asn Thr Gln Thr
```

-continued

```
                305                 310                 315                 320
Ser Lys Asn Ile Ile Leu
                325

<210> SEQ ID NO 21
<211> LENGTH: 273
<212> TYPE: PRT
<213> ORGANISM: Porphyromonas gingivalis

<400> SEQUENCE: 21

Met Lys Lys Ala Leu Leu Ile Gly Ala Leu Leu Gly Ala Val Ser
1               5                   10                  15

Phe Ala Ser Ala Gln Ser Leu Ser Thr Ile Lys Val Gln Asn Asn Ser
                20                  25                  30

Val Gln Gln Pro Arg Glu Glu Ala Thr Ile Gln Val Cys Gly Glu Leu
            35                  40                  45

Ala Glu Gln Val Asp Cys Ile Gly Thr Gly Asn Ser Ala Ile Ile Ala
        50                  55                  60

Ala Ala Lys Phe Glu Ser Asp Asp Leu Glu Ser Tyr Val Gly Trp
65                  70                  75                  80

Glu Ile Met Ser Val Asp Phe Phe Pro Gly Tyr Lys Ala Cys Lys Tyr
                85                  90                  95

Thr Ser Ala Val Trp Ala Asp Asp Met Thr Ile Leu Gly Gln Ser Glu
            100                 105                 110

Asp Ser Asp Pro Glu Met Gln Thr Ile Asn Asn Leu Ala Leu Lys Thr
        115                 120                 125

Ser Val Lys Ile Glu Ala Gly Lys Asn Tyr Ile Val Gly Tyr Ile Ala
    130                 135                 140

Asn Thr Ala Gly Gly His Pro Ile Gly Cys Asp Gln Gly Pro Ala Val
145                 150                 155                 160

Asp Gly Tyr Gly Asp Leu Val Ser Ile Ser Glu Asp Gly Gly Ala Thr
                165                 170                 175

Phe Pro Pro Phe Glu Ser Leu His Gln Ala Val Pro Thr Leu Asn Tyr
            180                 185                 190

Asn Ile Tyr Val Val His Leu Lys Lys Gly Glu Gly Val Glu Ala
        195                 200                 205

Val Leu Thr Asn Asp Lys Ala Asn Ala Tyr Val Gln Asn Gly Val Ile
    210                 215                 220

Tyr Val Ala Gly Ala Asn Gly Arg Gln Val Ser Leu Phe Asp Met Asn
225                 230                 235                 240

Gly Lys Val Val Tyr Thr Gly Val Ser Glu Thr Ile Ala Ala Pro Gln
                245                 250                 255

Lys Gly Met Tyr Ile Leu Arg Val Gly Ala Lys Ser Ile Lys Leu Ala
            260                 265                 270

Ile

<210> SEQ ID NO 22
<211> LENGTH: 925
<212> TYPE: PRT
<213> ORGANISM: Porphyromonas gingivalis

<400> SEQUENCE: 22

Met Gly Tyr Asp Pro His Val Arg Glu Trp Lys Leu Pro Leu Asn Gly
1               5                   10                  15

Lys Ala Arg Gly Lys Ser Ile Glu Val Ser Phe Pro Tyr Phe Tyr Arg
                20                  25                  30
```

```
Ala Asp Gln Ser Leu Lys Arg Arg Ile Pro Met Pro His His Leu
         35                  40                  45

Leu Ser Leu Thr Ser Leu Leu Arg Cys Arg Leu His His Phe Phe Leu
     50                  55                  60

Tyr Ile Ile Ile Ile Val Ser Ala Gly Tyr Ser Ala Thr Ala Gln Thr
 65                  70                  75                  80

Val Ile Lys Gly Leu Val Leu Ala Ala Asp Asn Glu Ala Pro Val Ser
                 85                  90                  95

Tyr Ala Ser Ile Tyr Val Ala Glu Thr Lys Ser Gly Val Val Ala Asp
             100                 105                 110

Glu Ser Gly Arg Phe Ile Leu Arg Leu His Pro Gly Arg Tyr Arg Leu
         115                 120                 125

Ala Ile Arg Ser Met Gly Tyr Thr Pro Leu Glu Thr Glu Leu Leu Val
     130                 135                 140

Gly Glu Lys Ser Glu Lys Thr Phe Arg Leu Ser Ser Val Ile Tyr
145                 150                 155                 160

Asp Leu Lys Glu Val Glu Val Ile Gly Lys Arg Pro Lys Glu Asp Pro
                 165                 170                 175

Ala Tyr Pro Ile Met Arg Glu Leu Ile Ala Arg Thr Pro Val Tyr Glu
             180                 185                 190

His Met Val Lys Ser Tyr Gln Ala Lys Val Tyr Thr Lys Gly Ser Met
         195                 200                 205

Arg Leu Asp Lys Leu Pro Phe Trp Leu Arg Tyr Lys Lys Ala Asp Gly
     210                 215                 220

Ile Ser Ala Lys Asp Leu Glu Lys Lys Arg Phe Val Ile Glu Ser Gln
225                 230                 235                 240

Ala Ser Leu Glu Phe Arg His Pro Asn Lys Tyr Asn Lys Gln Val Arg
             245                 250                 255

Ala Met Arg Ser Ser Ile Pro Asp Asp Leu Lys Ser Asp Thr Thr Asp
         260                 265                 270

Tyr Met Gln Ile Ile Ser Thr Asn Ile Tyr Ala Lys Glu Phe Ser Leu
     275                 280                 285

Asp Gly Ile Val Asn Met Ala Ser Pro Ile Arg Thr Gly Val Leu Glu
290                 295                 300

Ser Tyr Thr Tyr Lys Leu Glu Gly Thr Ser Arg Glu Lys Glu Arg Lys
305                 310                 315                 320

Val Tyr His Ile Ser Phe Lys Gly Arg Arg Asp Ala Met Arg Gly Glu
             325                 330                 335

Leu Trp Val Ile Asp Ser Ile Trp Cys Leu Gln Ala Leu Lys Leu Glu
         340                 345                 350

Ile Lys Ala Tyr Asp Met Ile Arg Tyr Lys Val Asp Ile Ser Leu Asn
     355                 360                 365

Pro Leu Glu Lys Asp Val Tyr Leu Pro Thr Thr Tyr Ala Ile Gly Met
370                 375                 380

Glu Met Gln Ser Met Gly Leu Lys Leu Glu Tyr Gln Tyr Phe Ser Ser
385                 390                 395                 400

Leu Val Tyr Asp Ser Leu Glu Ile Asp Arg Lys Leu Leu Ser Thr Ala
             405                 410                 415

Arg Arg Ala Glu Gly Leu Arg Phe Arg Thr Asn Arg Glu Val Asn Arg
         420                 425                 430

His Leu Arg Met Leu Glu Ser Arg Leu Asp Thr Leu Gly Tyr His Leu
     435                 440                 445
```

-continued

```
Pro Asp Lys Tyr Met Leu Pro Asp Thr Glu Leu Gln Ala Lys Val Arg
450                 455                 460

Phe Asp Ser Leu Ala Phe Asp Arg Asp Ser Ser Tyr Trp Asp Ala Val
465                 470                 475                 480

Val Thr Ala Pro Leu Thr Asp Glu Glu Ala Gln Ser Tyr Ala Asn Arg
                485                 490                 495

Asp Ser Leu Met Gln Ala Phe Glu Lys Lys Arg Arg Phe Gly Gly Gly
                500                 505                 510

Arg Glu Gly Glu Arg Thr Gly Arg Thr Ser Ile Leu Gly Ala Ile Leu
            515                 520                 525

Gly Gly His Asp Tyr Lys Met Gly Glu Gly Thr Thr Leu Gly Phe Asn
        530                 535                 540

Gly Leu Ile Arg Gly Ser Leu Tyr Asp Tyr Arg Tyr Thr Asp Gly Phe
545                 550                 555                 560

Trp Leu Gly Gln Ser Phe Phe Arg Gln Lys Phe Ser Lys Gly Val
                565                 570                 575

Asp Leu Thr Leu Arg Pro Ile Leu Tyr Tyr Thr Thr His Arg Arg Lys
            580                 585                 590

Leu Tyr Trp Asp Val Arg Ala Asp Phe Arg Tyr Ala Pro Leu Ser Gly
        595                 600                 605

Gly Leu Leu Ser Leu Ser Ala Gly Arg Gln Ser Ala Asp Leu Thr Gly
610                 615                 620

Pro Phe Ala Asn Thr Asp Trp Arg Ile Gln Thr Phe Leu Thr Thr Leu
625                 630                 635                 640

Val Asp Gly Arg Gly His Leu Met Leu Tyr Asp Lys Lys Tyr Leu Arg
                645                 650                 655

Leu Ser Asn Gln Ile Asp Leu Leu Pro Gly Leu Gln Leu Phe Leu Phe
                660                 665                 670

Ala Glu Gly Arg His Ser Ser Pro Leu Ala Glu Asn Arg Val Trp Gly
            675                 680                 685

Ile Phe Lys Lys Pro Ile Lys Asn Lys Leu Ile Gly Gly Ile Ala Ser
        690                 695                 700

Ser Pro Asp Ser Leu Leu Tyr Ser Met Pro Asp His Arg Ser Leu Thr
705                 710                 715                 720

Val Gly Gly Ser Ile Arg Tyr Asn Pro Ala Pro Tyr Tyr Arg Leu Asp
                725                 730                 735

Lys Asp Gly Arg Lys Arg Tyr Asp Gly Val Gly Thr Arg Ala Pro Leu
                740                 745                 750

Phe Gly Leu Thr Tyr Arg Gln Ala Ile Pro Leu Gly Arg Glu His Asp
        755                 760                 765

Ser Asp Tyr Ile Tyr Leu Ser Gly Ser Val Arg Gln Asn Leu Arg Leu
770                 775                 780

Asn Pro Leu His Ser Leu Tyr Tyr His Phe Thr Val Gly Ser Tyr Phe
785                 790                 795                 800

Arg Arg His Thr Val His Leu Asp Glu Gln Arg Tyr Leu Lys Ala Asp
                805                 810                 815

Asn Ala Leu Phe Gln Ile Gly Gly Thr Leu His Asp Ser Phe Gln Thr
                820                 825                 830

Leu Pro Pro Tyr Ser Tyr Thr Asp Gln Asn Phe Leu Ile Leu Gln Thr
            835                 840                 845

Arg Trp Ser Phe Pro Ser Leu Ile Thr Asn Pro Leu Gly Ile Leu Phe
        850                 855                 860

Ala Ser Phe Gln Ser Asn Leu His Leu Asn Thr Tyr Trp Gly Cys His
```

```
                865                 870                 875                 880
Lys Asp Arg Met Pro Phe Phe Glu Ile Gly Tyr Ser Arg Gly Thr Ile
                    885                 890                 895

Ala Gln Ile Gly Ile Phe Cys Gly Ala Tyr Asn Phe His Lys Asp Tyr
            900                 905                 910

Gly Leu Met Leu Arg Tyr Thr Ile Asn Phe Pro Thr Leu
        915                 920                 925

<210> SEQ ID NO 23
<211> LENGTH: 89
<212> TYPE: PRT
<213> ORGANISM: Porphyromonas gingivalis

<400> SEQUENCE: 23

Met Ser Glu Leu Arg Leu Ala Ile Met Ser Val Leu Met Ser Val Glu
1               5                   10                  15

Glu Ala Asp Phe Leu Tyr Leu Lys Glu Val Thr Gly Ala Thr Ser Gly
            20                  25                  30

Asn Ile Ser Val Gln Leu Asp Lys Leu Ser Thr Ala Gly Tyr Ile Glu
        35                  40                  45

Ile Glu Lys Gly Tyr Asn Gly Lys Arg Pro Arg Thr Thr Cys Arg Ala
    50                  55                  60

Thr Asp Ala Gly Arg Glu Ala Phe Ser Ala His Phe Glu Ala Leu Lys
65                  70                  75                  80

Ser Tyr Leu Pro Thr Asp Ser Thr His
                85

<210> SEQ ID NO 24
<211> LENGTH: 424
<212> TYPE: PRT
<213> ORGANISM: Porphyromonas gingivalis

<400> SEQUENCE: 24

Met Phe Asp Leu Asp Asn Leu His Glu Leu Gly Ala Thr Leu Arg Lys
1               5                   10                  15

Asn Met Leu Arg Thr Ala Leu Thr Gly Phe Ala Val Ala Trp Gly Val
            20                  25                  30

Leu Leu Leu Ile Leu Leu Leu Ser Ala Gly Arg Gly Phe Gln His Gly
        35                  40                  45

Ile Arg His Asn Val Glu Gln Phe Gly Met Gly Thr Ser Ala Ile Ser
    50                  55                  60

Phe Ser Thr Trp Arg Thr Ser Lys Glu Tyr Gly Tyr Pro Lys Asp
65                  70                  75                  80

Arg Tyr Ile Glu Leu Thr Pro Ala Asp Cys Asp Tyr Leu Val Lys Leu
                85                  90                  95

Asn Pro Asp Leu Ile Lys Gly Ala Ala Tyr Tyr Thr Asn Gln Trp Ser
            100                 105                 110

Tyr Asp Val Gln Tyr Glu Asp Arg Thr His Ser Thr Pro Thr Lys Ala
        115                 120                 125

Val Ser Gly Glu Tyr Gly Asn Met Val Lys Thr His Leu Ile Glu Gly
    130                 135                 140

Arg Phe Leu Ser Thr Ser Asp Asp Ala Met Lys Arg Lys Val Ile Val
145                 150                 155                 160

Leu Cys Glu Gln Thr Ala Asp Val Leu Phe Gly Glu Ser Ile Ser Pro
                165                 170                 175

Ile Gly Lys Tyr Val Asn Leu Ser Gln Ile Pro Phe Leu Val Val Gly
```

```
                180              185              190
Val Cys Lys Gly Glu Gln Gly Gln Phe Ser Pro Asn Tyr Ile Pro Phe
            195                  200                  205

Ala Thr Tyr Ser Gly Ile Phe Ala Lys Gly Phe Ser Leu Asp Cys Thr
            210                  215                  220

Leu Phe Met Asn Cys Pro Ser Val Arg Thr Glu Glu Asn Val Glu Arg
225                  230                  235                  240

Leu Lys Val Leu Leu Asn Arg Gln Leu Ala Phe Arg Lys Gly Tyr Asp
                245                  250                  255

Pro Thr Asp Met Glu Val Pro Tyr Val Asp Ala Pro Val Thr Asp Ile
                260                  265                  270

Lys Met Met Asp Lys Ile Phe Asn Gly Met Asp Val Phe Leu Trp Ile
                275                  280                  285

Ile Gly Leu Ser Thr Leu Val Ile Gly Ile Ile Gly Val Ala Asn Ile
            290                  295                  300

Met Gln Val Thr Val Asn Glu Arg Gln Arg Ile Gly Ile Arg Lys
305                  310                  315                  320

Ala Leu Gly Ala Lys Pro Arg Ala Ile Ile Asn Met Ile Leu Thr Glu
                325                  330                  335

Ala Val Val Val Thr Leu Phe Ser Gly Leu Ile Gly Leu Val Ala Gly
                340                  345                  350

Val Gly Leu Met Glu Phe Val Ser His Trp Val Gln Thr Thr Gly Val
            355                  360                  365

Gly Ser Arg Gln Val Glu Gly Ile Thr Leu Thr Leu Phe Arg Asp Pro
            370                  375                  380

Ser Ile Asp Leu Ser Thr Ala Leu Leu Ala Leu Ile Val Met Val Val
385                  390                  395                  400

Ser Gly Ala Ile Ala Gly Tyr Gln Pro Ala Arg Lys Ala Val Arg Ile
                405                  410                  415

Pro Ala Val Glu Ala Met Arg Asn
            420

<210> SEQ ID NO 25
<211> LENGTH: 185
<212> TYPE: PRT
<213> ORGANISM: Porphyromonas gingivalis

<400> SEQUENCE: 25

Met Ile Glu Lys Met Leu Glu Gln Thr Arg Lys Arg Leu Ile Arg Gly
1               5                   10                  15

Ala Gly Ile Pro Ser Leu Ile Trp Gly Tyr Val Thr Phe Ala Thr Ser
            20                  25                  30

Leu Leu Ile Leu Phe Val Tyr Pro His Ile Gly Tyr Arg Ala Asn Tyr
            35                  40                  45

Leu Trp Met Leu Ile Pro Ile Val Gly Gly Leu Thr Ile Ile Cys
        50                  55                  60

Asn Arg Lys Arg Gln Lys Glu Ala His Ala Arg Thr Gln Ile Asp Arg
65                  70                  75                  80

Phe Ile Asp Thr Thr Trp Ile Thr Ile Gly Leu Asn Val Thr Ala Leu
                85                  90                  95

Ser Ile Leu Ala Tyr Arg Phe Pro Leu Ala Ile Leu Pro Leu Val Leu
                100                 105                 110

Ile Leu Ile Gly Ile Ala Thr Ala Ile Thr Gly Phe Ser His Lys Val
            115                 120                 125
```

```
Thr Leu Leu Lys Tyr Ser Ser Ile Phe Gly Ile Leu Val Gly Tyr Met
            130                 135                 140

Leu Leu Val Val Pro Met Ser Gly Lys Leu Met Val Leu Ile Phe Gly
145                 150                 155                 160

Leu Thr Phe Phe Leu Met His Cys Val Pro Gly His Tyr Leu Cys Tyr
                165                 170                 175

Leu Glu Arg Lys Ile Leu Arg Asp Ala
            180                 185

<210> SEQ ID NO 26
<211> LENGTH: 341
<212> TYPE: PRT
<213> ORGANISM: Porphyromonas gingivalis

<400> SEQUENCE: 26

Met Lys Lys Asp Ile Ile Ile Leu Gly Ile Glu Ser Ser Cys Asp Asp
1               5                   10                  15

Thr Ser Ala Ala Val Val Arg Asn Glu Thr Met Leu Ser Asn Val Ile
            20                  25                  30

Ala Gly Gln Ala Val His Lys Ala Tyr Gly Gly Val Val Pro Glu Leu
        35                  40                  45

Ala Ser Arg Ala His Gln Gln Asn Ile Val Pro Val Ser Glu Ala
    50                  55                  60

Ile Lys Arg Ala Gly Ile Arg Lys Glu Glu Ile Asp Ala Ile Ala Phe
65                  70                  75                  80

Thr Arg Gly Pro Gly Leu Leu Gly Ser Leu Leu Val Gly Thr Ser Phe
                85                  90                  95

Ala Lys Gly Leu Ser Leu Ser Leu Gly Ile Pro Met Leu Glu Val Asn
            100                 105                 110

His Leu His Ala His Val Leu Ala Asn Phe Leu Arg Glu Pro Gly Glu
        115                 120                 125

Glu Ser Gln His Pro Ser Phe Pro Phe Leu Cys Leu Leu Val Ser Gly
    130                 135                 140

Gly Asn Ser Gln Ile Ile Leu Val Arg Ser Pro Tyr Asp Met Glu Val
145                 150                 155                 160

Ile Gly Gln Thr Ile Asp Asp Ala Ala Gly Glu Ala Phe Asp Lys Cys
                165                 170                 175

Ala Lys Val Met Gly Leu Gly Tyr Pro Gly Gly Pro Ile Val Asn Lys
            180                 185                 190

Leu Ala Ser Glu Gly Asn Pro Asp Ala Phe Arg Phe Ala Arg Pro His
        195                 200                 205

Val Ser Gly Tyr Asp Tyr Ser Phe Ser Gly Leu Lys Thr Ser Phe Leu
    210                 215                 220

Tyr Thr Leu Arg Asp Lys Leu Ala Glu Asp Pro Asp Phe Ile Glu Lys
225                 230                 235                 240

Asn Lys Ala Asp Leu Cys Ala Ser Leu Gln His Thr Val Ile Asp Ile
                245                 250                 255

Leu Met Lys Lys Leu Arg Gln Ala Ala Lys Asp His Ser Ile Lys Gln
            260                 265                 270

Val Ala Leu Ala Gly Gly Val Ser Ala Asn Thr Gly Leu Arg Asp Ala
        275                 280                 285

Phe His Asp His Ala Arg Arg Tyr Gly Trp Thr Val Phe Ile Pro Lys
    290                 295                 300

Phe Ala Tyr Thr Thr Asp Asn Ala Ala Met Val Ala Ile Ser Gly Tyr
305                 310                 315                 320
```

```
Tyr Lys Tyr Leu Gln Gly Asp Phe Cys Pro Ile Asp Ala Val Pro Phe
                325                 330                 335

Ser Arg Ile Thr Val
            340

<210> SEQ ID NO 27
<211> LENGTH: 527
<212> TYPE: PRT
<213> ORGANISM: Porphyromonas gingivalis

<400> SEQUENCE: 27

Met Asn Leu Asp Ala Leu Val Ser Trp Ser Arg Ala Gln Phe Ala Leu
1               5                   10                  15

Thr Ala Met Tyr His Trp Leu Phe Val Pro Leu Thr Leu Gly Leu Gly
            20                  25                  30

Val Ile Met Ala Ile Val Glu Thr Ile Tyr Tyr Arg Asn Gly Lys Pro
        35                  40                  45

Glu Trp Lys Arg Tyr Ala Gln Phe Trp Gln Lys Leu Phe Gly Ile Asn
    50                  55                  60

Phe Ala Ile Gly Val Ala Thr Gly Ile Ile Leu Glu Phe Glu Phe Gly
65                  70                  75                  80

Thr Asn Trp Ser Asn Tyr Ser Leu Phe Val Gly Asp Ile Phe Gly Ala
                85                  90                  95

Pro Leu Ala Ile Glu Gly Ile Leu Ala Phe Phe Met Glu Ala Thr Phe
            100                 105                 110

Ile Ala Val Met Phe Phe Gly Trp Asn Lys Val Ser Lys Gly Phe His
        115                 120                 125

Leu Ser Ala Thr Trp Leu Thr Ile Ile Gly Ala Ser Leu Ser Ala Val
    130                 135                 140

Trp Ile Leu Ile Ala Asn Ala Trp Met Gln Glu Pro Val Gly Met Thr
145                 150                 155                 160

Phe Asn Pro Asp Thr Met Arg Asn Glu Met Thr Asp Phe Trp Ala Leu
                165                 170                 175

Val Phe Ser Ser Thr Ala Ile Asn Lys Phe Trp His Thr Ile Ser Ser
            180                 185                 190

Cys Trp Thr Leu Gly Ser Val Phe Ala Leu Gly Val Cys Gly Ile Tyr
        195                 200                 205

Leu Leu Arg Lys Asp Asp Lys His Lys Asp Phe Ala Leu Lys Asn Ile
    210                 215                 220

Lys Ile Ile Ala Pro Phe Gly Leu Ala Ala Ser Leu Ile Thr Ala Phe
225                 230                 235                 240

Thr Gly Asp Thr Ser Ala Tyr Asn Val Ala Gln Lys Gln Pro Met Lys
                245                 250                 255

Leu Ala Ala Met Glu Ala Leu Tyr Asp Ser Gly Gln Thr Asp Lys Asp
            260                 265                 270

Gly Leu Thr Ala Asp Gly Lys Gly Leu Pro Leu Ser Leu Phe Gly Ile
        275                 280                 285

Leu Asn Pro Ala Lys Glu Thr Pro Gln Asp Lys Glu Ala Phe Leu
    290                 295                 300

Phe Asn Val Ser Val Pro Arg Val Leu Ser Val Leu Gly Thr Arg Asn
305                 310                 315                 320

Pro Ser Gly Tyr Val Pro Gly Ile Asn Asn Ile Leu Glu Gly Gly Tyr
                325                 330                 335

Val Lys Ala Asp Gly Thr Thr Ala Ile Pro Val Asp Ser Met Met Gln
```

```
                    340                 345                 350
Arg Gly Arg Arg Ala Ile Met Ala Leu Asn Asp Tyr Ser Lys Ala Lys
                355                 360                 365
Gln Ala Gly Asp Met Glu Ala Ala Leu Gln His Lys Ser Val Ile Asp
            370                 375                 380
Glu Asn Phe Pro Tyr Phe Gly Tyr Ser Tyr Ile Gln His Lys Asn Asp
385                 390                 395                 400
Ile Val Pro Pro Val Gly Leu Thr Tyr Tyr Ser Phe Arg Ile Met Val
                405                 410                 415
Gly Leu Gly Met Leu Phe Ile Leu Leu Phe Leu Met Ala Trp Leu Leu
                420                 425                 430
Ser Phe Lys Pro Glu Lys Phe Ser Lys Met Arg Trp Phe His Met Ile
                435                 440                 445
Ala Ile Val Cys Met Pro Leu Ala Trp Val Ala Ser Gln Ser Gly Trp
                450                 455                 460
Ile Val Ala Glu Val Gly Arg Gln Pro Trp Thr Ile Gln Asp Leu Leu
465                 470                 475                 480
Pro Val Gln Ala Ala Val Ser Lys Leu Glu Ala Gly Ser Val Ile Ile
                485                 490                 495
Thr Phe Phe Val Phe Leu Val Leu Phe Ser Ala Leu Leu Val Ala Glu
                500                 505                 510
Leu Asn Ile Met Arg Lys Ala Ile Lys Lys Gly Pro Glu Thr Glu
                515                 520                 525

<210> SEQ ID NO 28
<211> LENGTH: 306
<212> TYPE: PRT
<213> ORGANISM: Porphyromonas gingivalis

<400> SEQUENCE: 28

Met Thr Lys Val Leu Val Ala Thr Glu Lys Pro Phe Ala Lys Val Ala
1               5                   10                  15
Val Asp Gly Ile Lys Arg Ile Ile Glu Glu Ala Gly Leu Glu Phe Ala
                20                  25                  30
Leu Leu Glu Lys Tyr Thr Asp Lys Lys Gln Leu Leu Asp Ala Val Lys
            35                  40                  45
Asp Ala Asn Ala Ile Ile Ile Arg Ser Asp Gln Ile Asp Ala Glu Val
        50                  55                  60
Leu Asp Ala Ala Lys Glu Leu Lys Ile Val Val Arg Ala Gly Ala Gly
65                  70                  75                  80
Tyr Asp Asn Val Asp Leu Ala Ala Ala Thr Ala His Asn Val Cys Val
                85                  90                  95
Met Asn Thr Pro Gly Gln Asn Ser Asn Ala Val Ala Glu Leu Val Met
                100                 105                 110
Gly Met Leu Val Phe Met Tyr Arg Asn Leu Phe Asn Gly Ala Ser Gly
                115                 120                 125
Ser Glu Leu Met Gly Lys Lys Leu Gly Ile Leu Ala Tyr Gly Asn Val
                130                 135                 140
Gly Arg Asn Val Ala Arg Ile Ala Lys Gly Phe Gly Met Glu Ile Tyr
145                 150                 155                 160
Ala Tyr Asp Gln Phe Val Ser Ala Ala Asp Ile Glu Lys Glu Gly Val
                165                 170                 175
Lys Ala Val Ala Ser Arg Asp Ala Leu Phe Glu Thr Cys Asp Ile Val
                180                 185                 190
```

```
Ser Leu His Ile Pro Lys Thr Pro Glu Thr Val Lys Ser Ile Asn Ala
        195                 200                 205

Glu Leu Leu Ser Lys Met Pro Lys Gly Ala Cys Leu Ile Asn Thr Ala
    210                 215                 220

Arg Gln Glu Val Ile Asp Glu Gly Ile Cys Lys Phe Met Ala Glu
225                 230                 235                 240

Arg Thr Asp Phe Lys Tyr Ala Thr Asp Ile Lys Pro Thr Asn Asp Ala
                245                 250                 255

Glu Met Ala Lys Phe Glu Gly Arg Tyr Phe Thr Thr Pro Lys Lys Met
                260                 265                 270

Gly Ala Gln Thr Ala Glu Ala Asn Ile Asn Ala Gly Leu Ala Ala Ala
                275                 280                 285

Arg Gln Ile Val Asp Phe Ile Lys Asn Gly Asn Glu Lys Phe Arg Val
            290                 295                 300

Asn Lys
305

<210> SEQ ID NO 29
<211> LENGTH: 415
<212> TYPE: PRT
<213> ORGANISM: Porphyromonas gingivalis

<400> SEQUENCE: 29

Met Ala Ile Ile Lys Pro Phe Lys Gly Val Arg Pro Lys Glu Leu
1               5                   10                  15

Val Glu Gln Val Ala Ser Arg Pro Tyr Asp Val Leu Asn Ser Glu Glu
            20                  25                  30

Ala Arg Lys Glu Ala Lys Gly Asn Glu Lys Ser Leu Tyr His Ile Ile
        35                  40                  45

Arg Pro Glu Ile Asp Phe Pro Val Gly Lys Asp Glu His Asp Ala Asp
    50                  55                  60

Val Tyr Glu Lys Ala Ala Glu Asn Phe Arg Met Phe Gln Glu Lys Gly
65                  70                  75                  80

Trp Leu Val Gln Asp Thr Lys Glu Asn Tyr Tyr Val Tyr Ala Gln Thr
                85                  90                  95

Met Asn Gly Lys Thr Gln Tyr Gly Leu Val Val Gly Ala Tyr Val Glu
                100                 105                 110

Asp Tyr Met Asn Gly Val Ile Lys Lys His Glu Leu Thr Arg Arg Asp
            115                 120                 125

Lys Glu Glu Asp Arg Met Lys His Val Arg Val Asn Asp Ala Asn Ile
    130                 135                 140

Glu Pro Val Phe Phe Ala Tyr Pro Glu Asn Lys Glu Leu Asp Ala Ile
145                 150                 155                 160

Val Lys Lys Tyr Ala Ala Arg Pro Ala Glu Tyr Asp Phe Val Ala Glu
                165                 170                 175

Phe Asp Gly Phe Gly His His Phe Trp Val Ile Asp Glu Glu Ala Asp
                180                 185                 190

Ile Lys Arg Ile Thr Glu Leu Phe Ala Ala Met Pro Ala Leu Tyr Ile
            195                 200                 205

Ala Asp Gly His His Arg Ser Ala Ala Ala Leu Val Gly Ala Glu
        210                 215                 220

Lys Ala Lys Asn Asn Pro Asn His Arg Gly Asp Glu Glu Tyr Asn Tyr
225                 230                 235                 240

Phe Met Ala Val Cys Phe Pro Ala Asp Gln Leu Thr Ile Ile Asp Tyr
                245                 250                 255
```

```
Asn Arg Val Val Lys Asp Leu Asn Gly Leu Ser Asp Glu Glu Phe Leu
            260                 265                 270

Gln Lys Leu Ser Arg His Phe Glu Val Glu Cys Lys Gly Thr Glu Glu
        275                 280                 285

Tyr Arg Pro Ser Lys Leu His Asn Phe Ser Leu Tyr Leu Gly Gly Lys
    290                 295                 300

Trp Tyr Ser Leu Thr Ala Lys Ala Gly Thr Tyr Asp Asp Asn Asp Pro
305                 310                 315                 320

Ile Gly Val Leu Asp Val Thr Ile Ser Ser Asn Leu Ile Leu Asp Glu
                325                 330                 335

Ile Leu Gly Ile Lys Asp Leu Arg Ser Asp Lys Arg Ile Asp Phe Val
            340                 345                 350

Gly Gly Ile Arg Gly Leu Gly Glu Leu Lys Lys Arg Val Asp Ser Gly
        355                 360                 365

Glu Met Arg Val Ala Leu Ala Leu Tyr Pro Val Ser Met Lys Gln Leu
    370                 375                 380

Met Asp Ile Ala Asp Ser Gly Asn Ile Met Pro Pro Lys Thr Thr Trp
385                 390                 395                 400

Phe Glu Pro Lys Leu Arg Ser Gly Leu Ile Ile His Lys Leu Ser
                405                 410                 415

<210> SEQ ID NO 30
<211> LENGTH: 1161
<212> TYPE: DNA
<213> ORGANISM: Porphyromonas gingivalis

<400> SEQUENCE: 30
atgaaaaaag tgatgttggt cttcgggacg agacccgaag cgatcaagat ggctccgctg      60
gtgaaggaat tcaagcgag agcaagtgag tttgatacca ttgtctgtgt gacgggtcag      120
catagagaga tgctcaagca agtgctggag ctatttgata tcaagcccga ttatgacttg      180
gagatcatga aggaggggca ggatctctat gacgtaacta cacgtgtgct gttgggtatg      240
cgtgaagtac tcaagaagac aaagcccgat gtagtactcg tacacggcga tacgactaca      300
agtactgccg ctgcattggc tgctttctat caacagattc cggtaggaca tgtggaggca      360
gggcttcgca cgcacaacat ttacagccca tggccggaag agatgaaccg tcagctcacc      420
ggtaggatgg ctacctatca ctttgctcct acggaattga gtcgggacaa tttacttgca      480
gaagggattg ctacagatcg tatatttatt acaggaaata cagtaatcga tgctctacaa      540
caagtcgtta cacgagttaa gggtaatgcc gatttgcgaa atcaagtgtc tcgaaagcta      600
cttcaatttg gatatgatgt gaatcgttta gaggctgggc gtagacttgt tcttatcaca      660
gggcatcgca gagaaaactt tggcgaagga ttccttaata tctgccgtgc tattcaaact      720
cttagcaagc gtttcccgga ggtagacttt gtttatccca tgcaccttaa ccccaatgtg      780
cgtaagccta ttcgcgagat cttcggcgat aaccttggag gcttggataa tctctttttt      840
attgagccgc tggagtattt gcagtttgtt acgctcatgg atcgttcgtc cattgttctg      900
actgatagtg gaggtattca ggaagaagct ccagggttag gcaaacctgt attggtaatg      960
cgagatacta cggagcgtcc cgaagcggtg aaagcaggaa ccgtgaaact tgtagggaca     1020
gattataatc aaatcgtcga caatgtcgaa aaactactga cagacaacgc cgcatatgcc     1080
gaaatgagca gagccaataa tccgtacggt gacggaaaag catgctcata tagcggat      1140 gctcttactc gatgcattta g                                              1161
```

<210> SEQ ID NO 31
<211> LENGTH: 386
<212> TYPE: PRT
<213> ORGANISM: Porphyromonas gingivalis

<400> SEQUENCE: 31

```
Met Lys Lys Val Met Leu Val Phe Gly Thr Arg Pro Glu Ala Ile Lys
1               5                   10                  15

Met Ala Pro Leu Val Lys Glu Phe Gln Ala Arg Ala Ser Glu Phe Asp
            20                  25                  30

Thr Ile Val Cys Val Thr Gly Gln His Arg Glu Met Leu Lys Gln Val
        35                  40                  45

Leu Glu Leu Phe Asp Ile Lys Pro Asp Tyr Asp Leu Glu Ile Met Lys
    50                  55                  60

Glu Gly Gln Asp Leu Tyr Asp Val Thr Thr Arg Val Leu Leu Gly Met
65                  70                  75                  80

Arg Glu Val Leu Lys Lys Thr Lys Pro Asp Val Val Leu Val His Gly
                85                  90                  95

Asp Thr Thr Thr Ser Thr Ala Ala Ala Leu Ala Ala Phe Tyr Gln Gln
            100                 105                 110

Ile Pro Val Gly His Val Glu Ala Gly Leu Arg Thr His Asn Ile Tyr
        115                 120                 125

Ser Pro Trp Pro Glu Glu Met Asn Arg Gln Leu Thr Gly Arg Met Ala
    130                 135                 140

Thr Tyr His Phe Ala Pro Thr Glu Leu Ser Arg Asp Asn Leu Leu Ala
145                 150                 155                 160

Glu Gly Ile Ala Thr Asp Arg Ile Phe Ile Thr Gly Asn Thr Val Ile
                165                 170                 175

Asp Ala Leu Gln Gln Val Val Thr Arg Val Lys Gly Asn Ala Asp Leu
            180                 185                 190

Arg Asn Gln Val Ser Arg Lys Leu Leu Gln Phe Gly Tyr Asp Val Asn
        195                 200                 205

Arg Leu Glu Ala Gly Arg Arg Leu Val Leu Ile Thr Gly His Arg Arg
    210                 215                 220

Glu Asn Phe Gly Glu Gly Phe Leu Asn Ile Cys Arg Ala Ile Gln Thr
225                 230                 235                 240

Leu Ser Lys Arg Phe Pro Glu Val Asp Phe Val Tyr Pro Met His Leu
                245                 250                 255

Asn Pro Asn Val Arg Lys Pro Ile Arg Glu Ile Phe Gly Asp Asn Leu
            260                 265                 270

Gly Gly Leu Asp Asn Leu Phe Phe Ile Glu Pro Leu Glu Tyr Leu Gln
        275                 280                 285

Phe Val Thr Leu Met Asp Arg Ser Ser Ile Val Leu Thr Asp Ser Gly
    290                 295                 300

Gly Ile Gln Glu Glu Ala Pro Gly Leu Gly Lys Pro Val Leu Val Met
305                 310                 315                 320

Arg Asp Thr Thr Glu Arg Pro Glu Ala Val Lys Ala Gly Thr Val Lys
                325                 330                 335

Leu Val Gly Thr Asp Tyr Asn Gln Ile Val Asp Asn Val Glu Lys Leu
            340                 345                 350

Leu Thr Asp Asn Ala Ala Tyr Ala Glu Met Ser Arg Ala Asn Asn Pro
        355                 360                 365

Tyr Gly Asp Gly Lys Ala Cys Ser Tyr Ile Ala Asp Ala Leu Thr Arg
    370                 375                 380
```

Cys Ile
385

<210> SEQ ID NO 32
<211> LENGTH: 1506
<212> TYPE: DNA
<213> ORGANISM: Porphyromonas gingivalis

<400> SEQUENCE: 32

| | |
|---|---:|
| atgaaaaaaa taatttattg ggttgcgaca gttttcttag cagcgagcgt atcctcttgc | 60 |
| gagcttgacc gcgaccccga aggaaaagat ttccaacagc catatacttc tttcgtgcag | 120 |
| acgaaacaaa acagagatgg tctttacgca cttttgcgta atactgaaaa tccacgaatg | 180 |
| cattttatc aggaacttca atccgatatg tattgcacta ccattactga tggtaactcc | 240 |
| ttagctccgt tcgtgaattg ggatttaggc atacttaacg accatggacg tgctgatgag | 300 |
| gacgaagtct ccggtatagc tggctactat ttcgtataca atcgactaaa tcagcaagcg | 360 |
| aatgcttttg ttaacaatac ggaagctgcg ttgcagaatc aagtgtataa aaattccacc | 420 |
| gagatcgcca atgctaagag cttttttggcg gaaggaaaag ttttacaagc attggctatt | 480 |
| tggcgactga tggatcgttt tagcttccat gaaagcgtga cagaagttaa ttccggtgcg | 540 |
| aaagatcttg gcgttattct gttgaaagaa tataatcctg ttatatcgg tccccgtgca | 600 |
| acgaaggcac aatgttatga ttacattttg tcacgtttgt ctgaggctat gaagttttg | 660 |
| cccgaaaaca gggaaagcgt tctttatgtg agccgtgatt acgcctatgc cctccgagca | 720 |
| agaatttacc tcgcgttggg tgaatatgga aaagctgcag cagatgctaa gatggttgtt | 780 |
| gataagtatc ctttgattgg tgcagcagat gcttctgagt ttgagaatat ttatcgatca | 840 |
| gatgctaata atcccgaaat tatttttcgt ggttttgctt ctgcgactct tggctcgttt | 900 |
| actgctacga cactaaatgg tgctgcgcca gcaggtaagg atataaaata taatccgagc | 960 |
| gcagtcccctt tccaatgggt agtggatctt tatgaaaacg aagatttccg caaatccgta | 1020 |
| tatatcgcga aagttgtgaa aaaggataag gggtatttag taaataaatt ccttgaggac | 1080 |
| aaggcttatc gtgatgttca ggataagcca aaccttaaag tcggagctcg ttattttagc | 1140 |
| gttgctgagg tctacttaat tttggtagag tctgctcttc agactggaga taccccaaca | 1200 |
| gccgaaaaat atctcaaggc tttgagtaaa gctcgtggag cagaagtttc agtcgttaat | 1260 |
| atggaagcac tgcaagcaga gcgtacgcgt gagcttatag gtgagggtag tcgtttgcgt | 1320 |
| gatatggtcc gctggagtat ccctaataat catgatgctt tgagactca gcctggttta | 1380 |
| gaaggttttg caaatactac tcctttgaaa gctcaagctc ctgtaggctt ttatgcatat | 1440 |
| acttgggagt tccacagcg agatcgacaa actaatccgc agttaataaa gaactggccg | 1500 |
| atataa | 1506 |

<210> SEQ ID NO 33
<211> LENGTH: 501
<212> TYPE: PRT
<213> ORGANISM: Porphyromonas gingivalis

<400> SEQUENCE: 33

Met Lys Lys Ile Ile Tyr Trp Val Ala Thr Val Phe Leu Ala Ala Ser
1               5                   10                  15

Val Ser Ser Cys Glu Leu Asp Arg Asp Pro Glu Gly Lys Asp Phe Gln
                20                  25                  30

Gln Pro Tyr Thr Ser Phe Val Gln Thr Lys Gln Asn Arg Asp Gly Leu

```
                35                  40                  45
Tyr Ala Leu Leu Arg Asn Thr Glu Asn Pro Arg Met His Phe Tyr Gln
 50                  55                  60

Glu Leu Gln Ser Asp Met Tyr Cys Thr Thr Ile Thr Asp Gly Asn Ser
 65                  70                  75                  80

Leu Ala Pro Phe Val Asn Trp Asp Leu Gly Ile Leu Asn Asp His Gly
                 85                  90                  95

Arg Ala Asp Glu Asp Glu Val Ser Gly Ile Ala Gly Tyr Tyr Phe Val
                100                 105                 110

Tyr Asn Arg Leu Asn Gln Gln Ala Asn Ala Phe Val Asn Asn Thr Glu
                115                 120                 125

Ala Ala Leu Gln Asn Gln Val Tyr Lys Asn Ser Thr Glu Ile Ala Asn
130                 135                 140

Ala Lys Ser Phe Leu Ala Glu Gly Lys Val Leu Gln Ala Leu Ala Ile
145                 150                 155                 160

Trp Arg Leu Met Asp Arg Phe Ser Phe His Glu Ser Val Thr Glu Val
                165                 170                 175

Asn Ser Gly Ala Lys Asp Leu Gly Val Ile Leu Leu Lys Glu Tyr Asn
                180                 185                 190

Pro Gly Tyr Ile Gly Pro Arg Ala Thr Lys Ala Gln Cys Tyr Asp Tyr
                195                 200                 205

Ile Leu Ser Arg Leu Ser Glu Ala Ile Glu Val Leu Pro Glu Asn Arg
210                 215                 220

Glu Ser Val Leu Tyr Val Ser Arg Asp Tyr Ala Tyr Ala Leu Arg Ala
225                 230                 235                 240

Arg Ile Tyr Leu Ala Leu Gly Glu Tyr Gly Lys Ala Ala Ala Asp Ala
                245                 250                 255

Lys Met Val Val Asp Lys Tyr Pro Leu Ile Gly Ala Ala Asp Ala Ser
                260                 265                 270

Glu Phe Glu Asn Ile Tyr Arg Ser Asp Ala Asn Asn Pro Glu Ile Ile
                275                 280                 285

Phe Arg Gly Phe Ala Ser Ala Thr Leu Gly Ser Phe Thr Ala Thr Thr
290                 295                 300

Leu Asn Gly Ala Ala Pro Ala Gly Lys Asp Ile Lys Tyr Asn Pro Ser
305                 310                 315                 320

Ala Val Pro Phe Gln Trp Val Val Asp Leu Tyr Glu Asn Glu Asp Phe
                325                 330                 335

Arg Lys Ser Val Tyr Ile Ala Lys Val Val Lys Asp Lys Gly Tyr
                340                 345                 350

Leu Val Asn Lys Phe Leu Glu Asp Lys Ala Tyr Arg Asp Val Gln Asp
                355                 360                 365

Lys Pro Asn Leu Lys Val Gly Ala Arg Tyr Phe Ser Val Ala Glu Val
                370                 375                 380

Tyr Leu Ile Leu Val Glu Ser Ala Leu Gln Thr Gly Asp Thr Pro Thr
385                 390                 395                 400

Ala Glu Lys Tyr Leu Lys Ala Leu Ser Lys Ala Arg Gly Ala Glu Val
                405                 410                 415

Ser Val Val Asn Met Glu Ala Leu Gln Ala Glu Arg Thr Arg Glu Leu
                420                 425                 430

Ile Gly Glu Gly Ser Arg Leu Arg Asp Met Val Arg Trp Ser Ile Pro
                435                 440                 445

Asn Asn His Asp Ala Phe Glu Thr Gln Pro Gly Leu Glu Gly Phe Ala
450                 455                 460
```

Asn Thr Thr Pro Leu Lys Ala Gln Ala Pro Val Gly Phe Tyr Ala Tyr
465                 470                 475                 480

Thr Trp Glu Phe Pro Gln Arg Asp Arg Gln Thr Asn Pro Gln Leu Ile
            485                 490                 495

Lys Asn Trp Pro Ile
            500

<210> SEQ ID NO 34
<211> LENGTH: 1329
<212> TYPE: DNA
<213> ORGANISM: Porphyromonas gingivalis

<400> SEQUENCE: 34

| | | |
|---|---|---|
| atgctacatc atattatcaa gatcatccgc gccgaacgtc gtgccaacct ctggatatgg | 60 |
| ctggagatgc tcgtcgtatg tggcctgctt tggttcgtca cggactatgc cgtgacagct | 120 |
| ctgcgtgctt ggacacgccc attgaactac gatatagaac acgtgtaccg catcacgctg | 180 |
| gcaaccgtac aaaaagataa ggatggaaaa tggaagagaa ggtctgcgga tcagggaaaa | 240 |
| accatgatgc aaaccctcga tctgatcgct gcatatcccg agtggaagc ggcttgtctc | 300 |
| caacagtggg gcggtcatta ttcctcttcg tcaagtaaca gtagctttca actggacacc | 360 |
| gtatcactca taaacgttga ggatcgaatg gtttcgccgg attatttccg tgtatttcgt | 420 |
| gtctatggag ccgatggttc ttcgccggaa gagatggcgg aacgattcgg caaacttcac | 480 |
| atgaacgatc tccaacggga ctactatctc tcgcgcaatg ccctcgacta tgtgagaaa | 540 |
| gtcaatggcg aaggacgaga aagcgaccgc cgctacatag gcatgtcgga tagcatcaac | 600 |
| tacaatatgg tatccgttgt cgatggcgtc caaagcgaaa agagtatccg atacaatcag | 660 |
| acactgcgag gactcatacc ggatcagccc aaaaacgaag ccgaaagtac cggctatatc | 720 |
| agcctaaagc ccatcaccga ggagtacatt tcgcaaaacg aactcatatc ttactccgtc | 780 |
| tatctgcgtg tctctcccga gcggatacg ccggacttca agagcagtt cgtgaaaagg | 840 |
| atgaaagccg tgaccaagga cgatacctat cctgtactga cgatgaatgc cgtcagtgaa | 900 |
| gaccgggcag ggatattggc cgatcctgtc cggcagatca ataatcatct ggccatcggt | 960 |
| ttcttccttc tgctcaatat attcctcggg atcgtcggca ccttctgggt gcgaaccgag | 1020 |
| cagcgacgcg ccgaagtagg aatccgccgt gtagtgggat ccacgaacag gagcgtattc | 1080 |
| tcgctcatgt tcggcgaggg gattatactg atgacactgg ctttcctgcc tgcggccgta | 1140 |
| gccgcatggt acgtcatgtt ccataccgat ctttgcgaca tcaaggtgtt tcctctcggc | 1200 |
| cggggacgtc ttttgctcgg attggggtgt acttatttgc agatgctgct gatggttttt | 1260 |
| ctcggtactt tcattcccgt actgcgtgct ttgcgtgtgc ctccgaccga agctatccgc | 1320 |
| agcgagtag | 1329 |

<210> SEQ ID NO 35
<211> LENGTH: 442
<212> TYPE: PRT
<213> ORGANISM: Porphyromonas gingivalis

<400> SEQUENCE: 35

Met Leu His His Ile Ile Lys Ile Ile Arg Ala Glu Arg Arg Ala Asn
1               5                   10                  15

Leu Trp Ile Trp Leu Glu Met Leu Val Val Cys Gly Leu Leu Trp Phe
            20                  25                  30

Val Thr Asp Tyr Ala Val Thr Ala Leu Arg Ala Trp Thr Arg Pro Leu

-continued

```
                35                  40                  45
Asn Tyr Asp Ile Glu His Val Tyr Arg Ile Thr Leu Ala Thr Val Gln
 50                  55                  60

Lys Asp Lys Asp Gly Lys Trp Lys Glu Arg Ser Ala Asp Gln Gly Lys
 65                  70                  75                  80

Thr Met Met Gln Thr Leu Asp Leu Ile Ala Ala Tyr Pro Gly Val Glu
                 85                  90                  95

Ala Ala Cys Leu Gln Gln Trp Gly His Tyr Ser Ser Ser Ser Ser Ser
                100                 105                 110

Asn Ser Ser Phe Gln Leu Asp Thr Val Ser Leu Ile Asn Val Glu Asp
                115                 120                 125

Arg Met Val Ser Pro Asp Tyr Phe Arg Val Phe Arg Val Tyr Gly Ala
130                 135                 140

Asp Gly Ser Ser Pro Glu Glu Met Ala Glu Arg Phe Gly Lys Leu His
145                 150                 155                 160

Met Asn Asp Leu Gln Arg Asp Tyr Tyr Leu Ser Arg Asn Ala Leu Asp
                165                 170                 175

Tyr Val Glu Lys Val Asn Gly Glu Gly Arg Glu Ser Asp Arg Arg Tyr
                180                 185                 190

Ile Gly Met Ser Asp Ser Ile Asn Tyr Asn Met Val Ser Val Val Asp
                195                 200                 205

Gly Val Gln Ser Glu Lys Ser Ile Arg Tyr Asn Gln Thr Leu Arg Gly
                210                 215                 220

Leu Ile Pro Asp Gln Pro Lys Asn Glu Ala Glu Ser Thr Gly Tyr Ile
225                 230                 235                 240

Ser Leu Lys Pro Ile Thr Glu Glu Tyr Ile Ser Gln Asn Glu Leu Ile
                245                 250                 255

Ser Tyr Ser Val Tyr Leu Arg Val Ser Pro Glu Ala Asp Thr Pro Asp
                260                 265                 270

Phe Lys Glu Gln Phe Val Lys Arg Met Lys Ala Val Thr Lys Asp Asp
                275                 280                 285

Thr Tyr Pro Val Leu Thr Met Asn Ala Val Ser Glu Asp Arg Ala Gly
                290                 295                 300

Ile Leu Ala Asp Pro Val Arg Gln Ile Asn Asn His Leu Ala Ile Gly
305                 310                 315                 320

Phe Phe Leu Leu Leu Asn Ile Phe Leu Gly Ile Val Gly Thr Phe Trp
                325                 330                 335

Val Arg Thr Glu Gln Arg Ala Glu Val Gly Ile Arg Arg Val Val
                340                 345                 350

Gly Ser Thr Asn Arg Ser Val Phe Ser Leu Met Phe Gly Glu Gly Ile
                355                 360                 365

Ile Leu Met Thr Leu Ala Phe Leu Pro Ala Ala Val Ala Ala Trp Tyr
                370                 375                 380

Val Met Phe His Thr Asp Leu Cys Asp Ile Lys Val Phe Pro Leu Gly
385                 390                 395                 400

Arg Gly Arg Leu Leu Leu Gly Leu Gly Cys Thr Tyr Leu Gln Met Leu
                405                 410                 415

Leu Met Val Phe Leu Gly Thr Phe Ile Pro Val Leu Arg Ala Leu Arg
                420                 425                 430

Val Pro Pro Thr Glu Ala Ile Arg Ser Glu
                435                 440
```

<210> SEQ ID NO 36

```
<211> LENGTH: 1659
<212> TYPE: DNA
<213> ORGANISM: Porphyromonas gingivalis

<400> SEQUENCE: 36
atgaaatcgg acattcagat tgcacgtgac atcgaactgc aaagaatcga acagatagca      60
gagtcaatcg acttgcctgt cgaacaatta gaaccatacg gaatacacgg ccaaagtgcc     120
gctaagctgt atcgacgaag agaaagtaaa aagggaaat ctgattctgg tgacagccat      180
tacgccgaac aaggccggtg tgggaaaaac cactgtctcc atcggattgg ctctgggact     240
caaccatatc gggaagtcgt agccttgcgc gaaccttcgc tcggaccttg cttcggtatg     300
aaagggggg ctgccggagg tggctatgca caggtactgc ccatggagaa catcaacctc      360
cacttcaccg gtgatttcca tgctgtcact tcggctcaca acatgattac ggctcttttg     420
gagaactata tttatcagaa ccgcaatact tgcgacggcc tctccgaaat actttggaag     480
cgtgtactgg acgttaacga ccgctctttg cgcaatgccg ttacggggtt gggtaccatc     540
tcggacggaa tacctcgcca gaccggtttt gacattacgc cggcttccga gatcatggct     600
atcctctgtc tggccaaaga ctttgaagac ctccgcagcc gtcttgaaaa tattcttctc     660
ggctatacca agaaggtgc tcccctttacg gtcaaagacc tcggcatagc aggatccatt    720
gccgtcttgc tcaaagatgc cataaagcct aatctggtac agaccacaga gcacactccg     780
gcatttgtac atggaggccc cttttgccaat atcgcacatg gctgtaactc catcttggcc     840
acaaagatgg ctctctcttt cggcgaatat gccgtcaccg aggccggttt cggtgcagat     900
ctgggtgcag aaaaattcct tgacatcaaa tgtcgggaaa tgggtgtcgc acccaagctt     960
accgtcctcg tggccacgct gcgcgcgctc aaattgcatg gcggcgttgc cgaaacggaa    1020
atcaaggcac ccaatgccga agctctcaga agaggtttgt ccaatctgga tcgccacata   1080
tacaatctga aaaaattcgg tcagcaagta atcgttgcat caaccgcttt cgacaccgac    1140
gaagaagaag agatcagcat cgttcgtgag cattgtatcg ggcaaaatgt cggcttcgct    1200
gtgaacaacg cctttgcaga aggcggaaaa ggtgcggaag aactggcaaa acttgttgtg    1260
gaaatggtag agaataaacc ctcccagcct ctgaaatatg cctatgagcc ggagaatccc    1320
gtgaaaatga gatcgagaa gatcgccaag gaaatataca gcgcagggag tgtagtgtat    1380
agctccaaag cagacggcaa gctcaaaaag attgccatgc aatcgctgga tcatctcccc   1440
gtttgtattg ccaagacgca gtactctttc tcatccgacc ccaaagccaa gggagatgtc    1500
agagggtttg agctcaaagt atccgacatc atcatcaacc gtggagcagg catgctggtc    1560
gttatcatcg agagatcat gcgtatgccc ggactcccca agaaccgca agctgtacat     1620
atagatatag tagacggttt catcgaaggc cttagctga                           1659

<210> SEQ ID NO 37
<211> LENGTH: 555
<212> TYPE: PRT
<213> ORGANISM: Porphyromonas gingivalis

<400> SEQUENCE: 37

Met Lys Ser Asp Ile Gln Ile Ala Arg Asp Ile Glu Leu Gln Arg Ile
1               5                   10                  15

Glu Gln Ile Ala Glu Ser Ile Asp Leu Pro Val Glu Gln Leu Glu Pro
            20                  25                  30

Tyr Gly Arg Tyr Thr Ala Lys Val Pro Leu Ser Cys Ile Asp Glu Glu
        35                  40                  45
```

```
Lys Val Lys Lys Gly Asn Leu Ile Leu Val Thr Ala Ile Thr Pro Asn
 50                  55                  60
Lys Ala Gly Val Gly Lys Thr Thr Val Ser Ile Gly Leu Ala Leu Gly
 65                  70                  75                  80
Leu Asn His Ile Gly Lys Lys Ala Ile Val Ala Leu Arg Glu Pro Ser
                 85                  90                  95
Leu Gly Pro Cys Phe Gly Met Lys Gly Ala Ala Gly Gly Gly Tyr
            100                 105                 110
Ala Gln Val Leu Pro Met Glu Asn Ile Asn Leu His Phe Thr Gly Asp
        115                 120                 125
Phe His Ala Val Thr Ser Ala His Asn Met Ile Thr Ala Leu Leu Glu
    130                 135                 140
Asn Tyr Ile Tyr Gln Asn Arg Asn Thr Cys Asp Gly Leu Ser Glu Ile
145                 150                 155                 160
Leu Trp Lys Arg Val Leu Asp Val Asn Asp Arg Ser Leu Arg Asn Ala
                165                 170                 175
Val Thr Gly Leu Gly Thr Ile Ser Asp Gly Ile Pro Arg Gln Thr Gly
            180                 185                 190
Phe Asp Ile Thr Pro Ala Ser Glu Ile Met Ala Ile Leu Cys Leu Ala
        195                 200                 205
Lys Asp Phe Glu Asp Leu Arg Ser Arg Leu Glu Asn Ile Leu Leu Gly
    210                 215                 220
Tyr Thr Lys Glu Gly Ala Pro Phe Thr Val Lys Asp Leu Gly Ile Ala
225                 230                 235                 240
Gly Ser Ile Ala Val Leu Leu Lys Asp Ala Ile Lys Pro Asn Leu Val
                245                 250                 255
Gln Thr Thr Glu His Thr Pro Ala Phe Val His Gly Gly Pro Phe Ala
            260                 265                 270
Asn Ile Ala His Gly Cys Asn Ser Ile Leu Ala Thr Lys Met Ala Leu
        275                 280                 285
Ser Phe Gly Glu Tyr Ala Val Thr Glu Ala Gly Phe Gly Ala Asp Leu
    290                 295                 300
Gly Ala Glu Lys Phe Leu Asp Ile Lys Cys Arg Glu Met Gly Val Ala
305                 310                 315                 320
Pro Lys Leu Thr Val Leu Val Ala Thr Leu Arg Ala Leu Lys Leu His
                325                 330                 335
Gly Gly Val Ala Glu Thr Glu Ile Lys Ala Pro Asn Ala Glu Ala Leu
            340                 345                 350
Arg Arg Gly Leu Ser Asn Leu Asp Arg His Ile Tyr Asn Leu Lys Lys
        355                 360                 365
Phe Gly Gln Gln Val Ile Val Ala Phe Asn Arg Phe Asp Thr Asp Glu
    370                 375                 380
Glu Glu Glu Ile Ser Ile Val Arg Glu His Cys Ile Gly Gln Asn Val
385                 390                 395                 400
Gly Phe Ala Val Asn Asn Ala Phe Ala Glu Gly Gly Lys Gly Ala Glu
                405                 410                 415
Glu Leu Ala Lys Leu Val Val Glu Met Val Glu Asn Lys Pro Ser Gln
            420                 425                 430
Pro Leu Lys Tyr Ala Tyr Glu Pro Glu Asn Pro Val Lys Met Lys Ile
        435                 440                 445
Glu Lys Ile Ala Lys Glu Ile Tyr Ser Ala Gly Ser Val Val Tyr Ser
    450                 455                 460
Ser Lys Ala Asp Gly Lys Leu Lys Lys Ile Ala Met Gln Ser Leu Asp
```

-continued

```
            465                 470                 475                 480
His Leu Pro Val Cys Ile Ala Lys Thr Gln Tyr Ser Phe Ser Ser Asp
                485                 490                 495

Pro Lys Ala Lys Gly Asp Val Arg Gly Phe Glu Leu Lys Val Ser Asp
                500                 505                 510

Ile Ile Ile Asn Arg Gly Ala Gly Met Leu Val Val Ile Ile Gly Glu
                515                 520                 525

Ile Met Arg Met Pro Gly Leu Pro Lys Glu Pro Gln Ala Val His Ile
            530                 535                 540

Asp Ile Val Asp Gly Phe Ile Glu Gly Leu Ser
545                 550                 555
```